US011819667B2

(12) United States Patent
Livingston et al.

(10) Patent No.: US 11,819,667 B2
(45) Date of Patent: Nov. 21, 2023

(54) LIQUID DELIVERY CAP DEVICES, SYSTEMS, AND METHODS

(71) Applicant: PATIENTS PENDING LTD., London (GB)

(72) Inventors: Adam Joseph Livingston, Oceanside, CA (US); John Christian Love, San Diego, CA (US); George Crothall, Oceanside, CA (US); Anthony David Barghini, Encinitas, CA (US); Jeffrey Michael Johnson, San Diego, CA (US); Tinh Thanh Tran, San Diego, CA (US)

(73) Assignee: PATIENTS PENDING LTD., London (GB)

( * ) Notice: Subject to any disclaimer, the term of this patent is extended or adjusted under 35 U.S.C. 154(b) by 638 days.

(21) Appl. No.: 17/041,616

(22) PCT Filed: Dec. 18, 2018

(86) PCT No.: PCT/IB2018/060267
§ 371 (c)(1),
(2) Date: Sep. 25, 2020

(87) PCT Pub. No.: WO2019/186261
PCT Pub. Date: Oct. 3, 2019

(65) Prior Publication Data
US 2021/0023306 A1 Jan. 28, 2021

Related U.S. Application Data

(60) Provisional application No. 62/648,046, filed on Mar. 26, 2018.

(51) Int. Cl.
*A61M 5/315* (2006.01)
*A61M 5/31* (2006.01)

(52) U.S. Cl.
CPC .... *A61M 5/31525* (2013.01); *A61M 5/31568* (2013.01); *A61M 2005/3126* (2013.01);
(Continued)

(58) Field of Classification Search
CPC .......... A61M 5/31525; A61M 5/31568; A61M 2005/3126; A61M 2205/3306; A61M 2205/3327
See application file for complete search history.

(56) References Cited

U.S. PATENT DOCUMENTS 8,556,866 B2 * 10/2013 Krulevitch ........ A61M 5/31525
604/246
9,642,968 B2 * 5/2017 Whalley ................ G16H 20/30
(Continued)

FOREIGN PATENT DOCUMENTS

EP 2182456 5/2010
EP 2763722 8/2014
(Continued)

OTHER PUBLICATIONS

Office Action issued for Japanese Patent Application No. 2020-551834, dated Dec. 13, 2022, 7 pages including machine translation.
(Continued)

*Primary Examiner* — Dung T Ulsh
(74) *Attorney, Agent, or Firm* — Hamre, Schumann, Mueller & Larson, P.C.

(57) ABSTRACT

A liquid delivery system cap device is provided. In some embodiments, an example cap device includes a body defining a cavity configured to receive at least a portion of a liquid delivery device, a first sensor configured to output a first sensor signal indicative of a plunger of the liquid delivery device, and a processor configured to detect a plunger of the liquid delivery device based on a variation in the sensor signal of the first sensor.

22 Claims, 23 Drawing Sheets

(52) U.S. Cl.
CPC ............... *A61M 2205/3306* (2013.01); *A61M 2205/3327* (2013.01)

(56) References Cited

U.S. PATENT DOCUMENTS

| | | | |
|---|---|---|---|
| 9,858,887 B2* | 1/2018 | Cowe | B41J 3/4076 |
| 11,439,762 B2* | 9/2022 | Toporek | A61M 5/31551 |
| 2006/0224123 A1* | 10/2006 | Friedli | A61M 5/31525 |
| | | | 604/207 |

FOREIGN PATENT DOCUMENTS

| | | |
|---|---|---|
| EP | 2814543 | 12/2014 |
| EP | 2945673 | 11/2015 |
| EP | 2879740 | 3/2017 |
| EP | 3175876 | 6/2017 |
| JP | 2009-279438 A | 12/2009 |
| JP | 2012-519026 A | 8/2012 |
| JP | 2013-530004 A | 7/2013 |
| JP | 2017-531454 A | 10/2017 |
| JP | 2017-531459 A | 10/2017 |
| WO | 2010/098928 | 9/2010 |
| WO | 2014/111341 | 7/2014 |
| WO | 2014/161953 | 10/2014 |
| WO | 2016/019375 | 2/2016 |
| WO | 2017/009724 | 1/2017 |
| WO | 2017/050781 | 3/2017 |

OTHER PUBLICATIONS

International Search Report and Written Opinion issued for PCT/IB2018/060267, dated Apr. 29, 2019, 12 pages.

Office Action issued for Indian Patent Application No. 202047041587, dated Aug. 5, 2022, 6 pages.

* cited by examiner

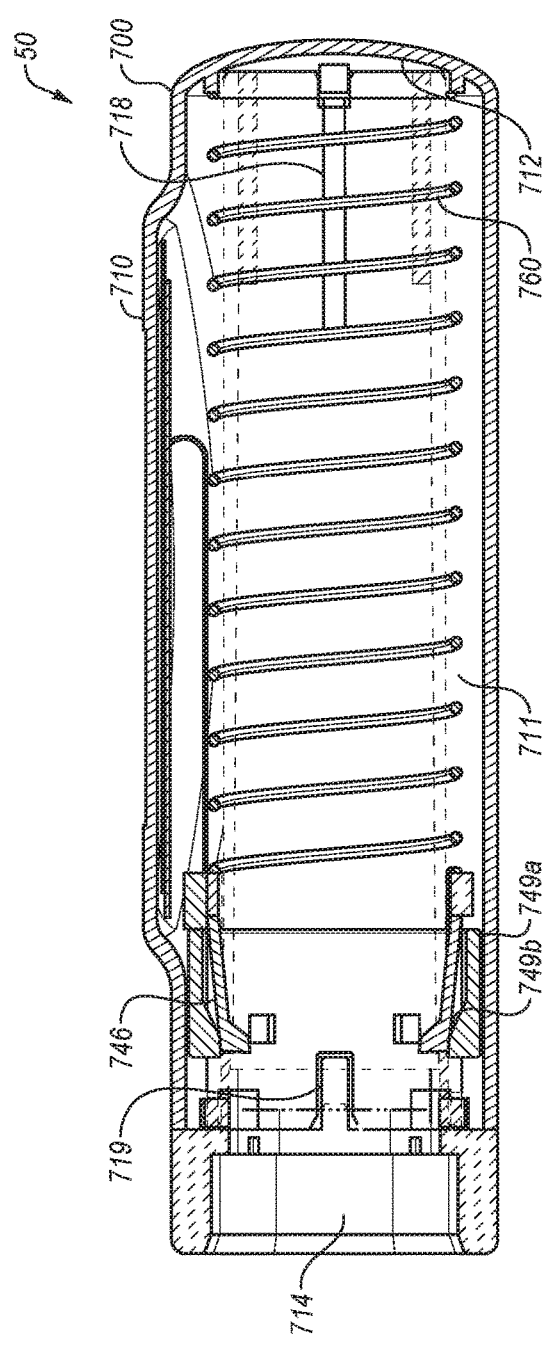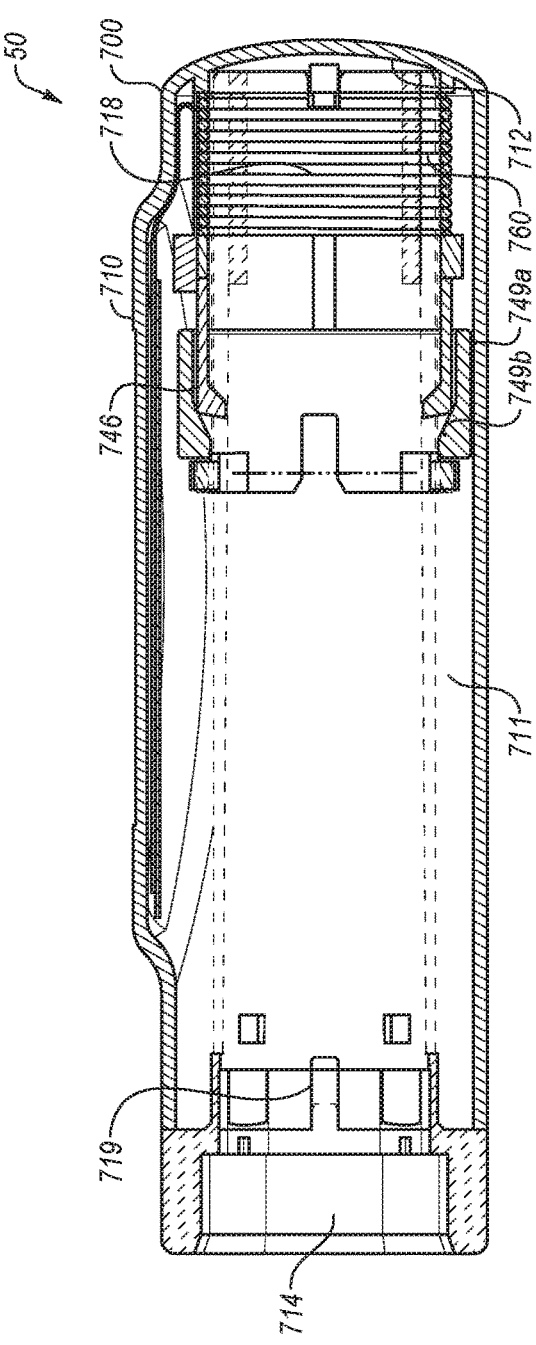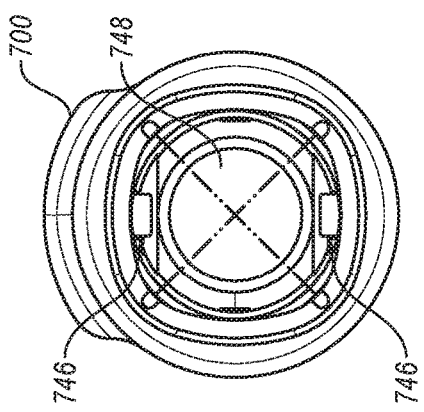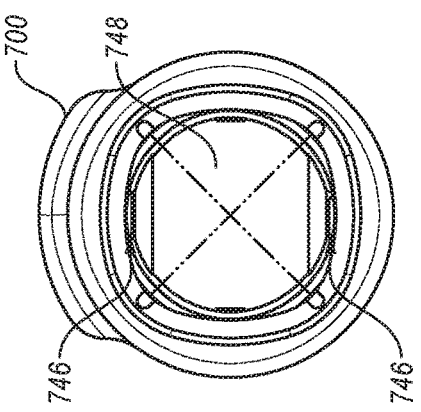

LIQUID DELIVERY CAP DEVICES, SYSTEMS, AND METHODS

CROSS-REFERENCE TO RELATED APPLICATIONS

This application claims priority to U.S. Application Ser. No. 62/648,046, filed on Mar. 26, 2018. The disclosure of the prior application is considered part of the disclosure of this application, and is incorporated in its entirety into this application.

TECHNICAL FIELD

This document describes devices, systems, and methods related to cap devices of a liquid delivery device, for example, cap devices configured to detect a plunger of the liquid delivery device.

BACKGROUND

Liquid delivery systems are commonly used to deliver a measured quantity of a drug to a patient. For example, pen-injector delivery devices have been used to deliver a measured quantity of a drug, and include a delivery end that is capped for storage between uses and a plunger movable within a reservoir to dispense a measured dose. A cap device may protect the delivery end from damage during storage and may be used to display information to a user, such as a duration since the cap was last removed during a previous use of the injection device or information about the contents of the delivery device.

SUMMARY

Some embodiments described herein include cap devices, systems, and methods configured to detect a condition of a liquid delivery device and output dosage information based on the detected condition. For example, a liquid delivery system may include a liquid delivery device having a reservoir and a movable plunger to force liquid from the reservoir, and a cap device configured to cover at least a delivery end of the liquid delivery device. The cap device includes one or more sensors configured to detect a condition of the liquid delivery device, such as a position of the plunger. The plunger position can be used to determine the liquid volume within the reservoir, dosage information (e.g. the volume of a previously delivered dose), and/or other information related to the liquid delivery device and its operation.

Some example cap devices optionally include a body and a sensor carriage movably located within the body. The sensor carriage may include one or more sensors that output sensor signals. The sensor signals may vary based on a feature of the liquid delivery sensor encountered by the one or more sensors, such as a plunger or liquid within the reservoir. In some embodiments, the sensor carriage may be movable between first and second positions without user operation, or movable by positioning the cap device on the liquid delivery device without additional user operation.

Some example cap devices may facilitate accurate and repeatable detection of the plunger position of the liquid delivery device, and in turn, the volume of a previously delivered dose or the volume remaining in the reservoir, for example. Alternatively or additionally, some embodiments facilitate accurate and repeatable measurement by reducing manual manipulation during detection. For example, the sensor carriage may move between first and second positions while the liquid delivery device is in a fixed position relative to a body of the cap device, and without additional manual operation by a user beyond the operation of engaging the liquid delivery device with the cap device.

In some embodiments, the sensor carriage may be pushed inward into a cavity of the cap device by engagement of the liquid delivery device with the cap device. The sensor carriage may optionally be movable with the liquid delivery device until the cap device is retained on the liquid delivery device, at which point the sensor carriage may subsequently be released. One or more sensors of the sensor carriage may be configured to scan the liquid delivery device while the sensor carriage travels from a first position to a second position. Subsequent disengagement or removal of the liquid delivery device from the cap device may reset the cap device to allow subsequent engagement with the liquid delivery device. Accordingly, in some example embodiments, the cap device may be configured to repeatedly and reliably scan a liquid delivery to detect its plunger, and/or to evaluate characteristics of the liquid delivery device and its use.

In some optional embodiments, the cap device includes one or more sensors configured to output sensor signals indicative of a feature of the liquid delivery device, and one or more positions sensors configured to output sensor signals related to position. For example, the cap device may include first and second optical sensors configured to output sensor signals indicative of a plunger of the liquid delivery device, and a linear potentiometer configured to output sensor signals that can be used to determine a corresponding position of the plunger. In various example embodiments, the cap device may optionally include one or more color sensors, infrared sensors, image sensors, etc., and/or one or more of a rotary encoder, linear encoder, membrane potentiometer, magnet potentiometer, etc.

Particular embodiments described herein include a liquid delivery system cap device, the cap device comprising a body defining a cavity configured to receive at least a portion of a liquid delivery device, and a sensor carriage movable within the cavity and including a first sensor. The sensor carriage may be movable between a first position and a second position relative to the cavity while the liquid delivery device is in a fixed positon relative to the cavity.

In some implementations, the system can optionally include one or more of the following features. The cavity may be defined by a front wall and one or more side walls of the body, and the body may define an opening to the cavity. In the first position the sensor carriage may be located proximate the front wall. In the second position the sensor carriage may be located proximate the opening. The device may further comprise a spring, the spring biased to move the sensor carriage from the first position to the second position. The first sensor may be configured to output a sensor signal indicative of a physical feature of the liquid delivery device. The first sensor may be configured to output a sensor signal indicative of a plunger of the liquid delivery device while the sensor carriage moves between the first position and the second position. The sensor carriage may comprise a first transmissive sensor. The sensor carriage may comprise a first reflective sensor. The sensor carriage may comprise an optical sensor having a first optical emitter aligned with a first optical receiver. The first sensor may comprise an optical path between the first optical emitter and the first optical receiver, and the optical path may be perpendicular to a longitudinal axis of the cavity of the cap device. The optical path may not intersect a central longitudinal axis of the cavity of the cap device. The sensor carriage may comprise a second optical sensor having a second optical emitter aligned with a second optical receiver. The first optical emitter may not be aligned with the second optical receiver, and the second optical emitter may not be aligned with the first optical receiver. The device may further comprise a position sensor. The device may further comprise a processor configured to detect a plunger of the liquid delivery device based on a variation in the sensor signal of the first sensor, and to determine a corresponding position based on a sensor signal output by the position sensor. The position sensor may comprise a linear potentiometer, the linear potentiometer may include a resistive element and a wiper movable along the resistive element. The wiper may be located on the sensor carriage. An output of the linear potentiometer may be indicative of a position of the sensor carriage. The position sensor may comprise a linear encoder, the linear encoder may include a codestrip and an encoder movable along the codestrip. The position sensor may comprise a rotary encoder, the rotary encoder may include a codewheel and an encoder.

Particular embodiments described herein include a liquid delivery system, comprising a liquid delivery device including a reservoir, a liquid within the reservoir, and a plunger movable within the reservoir to dispense liquid from the reservoir; and a cap device including a body defining a cavity configured to receive at least a portion of a liquid delivery device, a sensor carriage movable within the cavity and including one or more sensors configured to output a sensor signal indicative of a physical feature of the liquid delivery device, and a position sensor. The sensor carriage may be movable between a first position and a second position relative to the cavity while the liquid delivery device is in a fixed positon relative to the cavity.

In some implementations, the system can optionally include one or more of the following features. The cap device may comprise a processor configured to detect a plunger of the liquid delivery device based on a variation in the sensor signal of the first sensor, and to determine a corresponding position based on a sensor signal of the position sensor. The processor may be located in the cap device. The one or more sensors may be located on the sensor carriage may comprise first and second optical sensors, the first optical sensor having a first optical emitter aligned with a first optical receiver, and the second optical sensor having a second optical emitter aligned with a second optical receiver. The first optical sensor may comprise an optical path between the first optical emitter and the first optical receiver, and the optical path may be perpendicular to a central longitudinal axis of the cavity of the cap device. The first optical path may not intersect a central longitudinal axis of the cavity of the cap device.

Particular embodiments described herein include a method of evaluating the condition of a liquid delivery device, comprising receiving at least a portion of a liquid delivery device within a cavity of a cap device; releasing a sensor carriage including one or more sensors to move the sensor carriage from a first position to a second position while the liquid delivery device remains in a fixed position within the cavity; evaluating an output of the one or more sensors indicative of the presence of a feature of the liquid delivery device.

In some implementations, the system can optionally include one or more of the following features. The method may further comprise evaluating by a processor within the cap device an output of a position sensor to evaluate a position of the feature of the liquid delivery device. The feature of the liquid delivery device may be a plunger. The one or more sensors may comprise first and second optical sensors, and the position sensor may comprises a linear potentiometer including a resistive element and a wiper. The wiper may be located on the sensor carriage.

Particular embodiments described herein include a liquid delivery system cap device, comprising a body defining a cavity configured to receive a liquid delivery device; and means for moving one or more plunger sensors with the cavity of the body.

In some implementations, the system can optionally include one or more of the following features. The cap device may further comprise means for detecting a position of the one or more plunger sensors.

Particular embodiments described herein include a liquid delivery system cap device, the cap device comprising a body defining a cavity configured to receive at least a portion of a liquid delivery device; a first sensor configured to output a first sensor signal indicative of a plunger of the liquid delivery device; a second sensor configured to output a second sensor signal indicative of a position; and a processor configured to detect a plunger of the liquid delivery device based on a variation in the sensor signal of the first sensor, and to determine a corresponding position based on a sensor signal output by the second sensor. The second sensor may comprise a linear encoder including a code strip and an encoder.

In some implementations, the system can optionally include one or more of the following features. The linear encoder may be a reflective linear encoder. The linear encoder may be a transmissive linear encoder. The encoder may be located on a sensor carriage movable within the cavity of the body between a first position and a second position. The first sensor may be fixed relative to the body. The first sensor may be located on the sensor carriage and movable between the first position and the second position. The cap device may include a first spring biased to move the sensor carriage between the first position and the second position. The sensor carriage may comprise a second spring in frictional engagement with the body while the sensor carriage moves between the first position and the second position. The encoder may be separated from the code strip by a space when the sensor carriage is movable between the first position and the second position.

Particular embodiments described herein include a liquid delivery system cap device, the cap device comprising a body defining a cavity configured to receive at least a portion of a liquid delivery device; a first sensor configured to output a first sensor signal indicative of a plunger of the liquid delivery device; a second sensor configured to output a second sensor signal indicative of a position; and a processor configured to detect a plunger of the liquid delivery device based on a variation in the sensor signal of the first sensor, and to determine a corresponding position based on a sensor signal output by the second sensor. The second sensor may comprise a rotary encoder including a codewheel and an encoder.

In some implementations, the system can optionally include one or more of the following features. The cap device may comprise a track and a carriage movable between a first position and a second position along the track, and the carriage may be configured to receive a delivery end of a liquid delivery device. The track may include a helical slot, and the track may be rotatable by movement of the carriage between the first position and a second position along the helical slot. Rotation of the track may cause rotation of the codewheel. The cap device may comprise a gear train, and rotation of the track may be translated to the codewheel via the gear train. The carriage may not include a sensor or sensor component. The first sensor may be fixedly positioned relative to the body of the cap device. The first sensor may be located on the carriage movable between a first position and a second position.

Particular embodiments described herein include a method of evaluating the condition of a liquid delivery device, comprising receiving at least a portion of a liquid delivery device within a cavity of a cap device; generating by a first sensor a first sensor signal indicative of a feature of a liquid delivery device; generating by a second sensor a second sensor signal output indicative of a position associated with the first sensor signal output; evaluating the first sensor signal output and the sensor signal output to determine a position of the feature of the liquid delivery device.

In some implementations, the system can optionally include one or more of the following features. The second sensor may comprise a linear encoder including a code strip and an encoder, and generating the second sensor signal output comprises moving the encoder along the code strip. The second sensor may comprise a rotary encoder including a code wheel and an encoder, and generating the second sensor signal output comprises relative rotation between the codewheel and the encoder. The feature may be a plunger of the liquid delivery device. The method may further comprise displaying an output related to the position of the plunger. The output may be the volume of a previous dose delivered from the liquid delivery device.

Particular embodiments described herein include a liquid delivery system cap device, the cap device including a body defining a cavity configured to receive at least a portion of a liquid delivery device, a sensor carriage movable within the cavity and including a first sensor, and a motor configured to move the sensor carriage. The sensor carriage is movable between a first position and a second position while the liquid delivery device is in a fixed position relative to the cavity.

In some implementations, the device can optionally include one or more of the following features. The electric motor may be configured to drive the sensor carriage along a portion of the liquid delivery device. The cavity may be defined by a front wall and one or more side walls of the body, and the body may define an opening to the cavity. The first sensor may be configured to output a sensor signal indicative of a physical feature of the liquid delivery device. The first sensor may be configured to output a sensor signal indicative of a plunger of the liquid delivery device while the sensor carriage moves between the first position and the second position. The device may further include a sleeve configured to receive at least a portion of the liquid delivery device. The sensor carriage may be configured to move along an outside of the sleeve. The first sensor may include an optical path between the first optical emitter and the first optical receiver, and the optical path may be perpendicular to a longitudinal axis of the cavity of the cap device. The optical path may pass through a material thickness of the sleeve. The sensor carriage may include a second optical sensor having a second optical emitter aligned with a second optical receiver. The first optical emitter may not be aligned with the second optical receiver, and the second optical emitter may not be aligned with the first optical receiver. The device may include a position sensor. The device may include a processor configured to detect a plunger of the liquid delivery device based on a variation in the sensor signal of the first sensor, and to determine a corresponding position based on a sensor signal output by the position sensor. The position sensor may include a linear encoder, and the linear encoder may include a codestrip and an encoder movable along the codestrip.

Particular embodiments described herein include a liquid delivery system, including a liquid delivery device including a reservoir, a liquid within the reservoir, and a plunger movable within the reservoir to dispense liquid from the reservoir. The system further includes a cap device including a body defining a cavity configured to receive at least a portion of a liquid delivery device, a sensor carriage movable within the cavity and including one or more sensors configured to output a sensor signal indicative of a physical feature of the liquid delivery device, a motor configured to move the sensor carriage, and a position sensor. The sensor carriage is movable between a first position and a second position relative to the cavity while the liquid delivery device is in a fixed positon relative to the cavity.

In some implementations, the device can optionally include one or more of the following features. The system may include a processor configured to detect a plunger of the liquid delivery device based on a variation in the sensor signal of the first sensor, and to determine a corresponding position based on a sensor signal of the position sensor. The processor may be located in the cap device. The one or more sensors located on the sensor carriage may include first and second optical sensors, and the first optical sensor may include a first optical emitter aligned with a first optical receiver, and the second optical sensor may include a second optical emitter aligned with a second optical receiver.

Particular embodiments described herein include a method of evaluating the condition of a liquid delivery device, including receiving at least a portion of a liquid delivery device within a cavity of a cap device, driving a sensor carriage including one or more sensors from a first position to a second position while the liquid delivery device remains in a fixed position within the cavity, and evaluating an output of the one or more sensors indicative of the presence of a feature of the liquid delivery device.

In some implementations, the device can optionally include one or more of the following features. Driving the sensor carriage may include driving the sensor carriage by an electric motor. The method may include evaluating by a processor within the cap device an output of a position sensor to evaluate a position of the feature of the liquid delivery device. The feature of the liquid delivery device may be a plunger.

Particular embodiments described herein include a liquid delivery system cap device, including a body defining a cavity configured to receive a liquid delivery device, and means for moving one or more plunger sensors with the cavity of the body.

In some implementations, the device can optionally include one or more of the following features. The means for moving may include an electric motor.

Particular embodiments described herein include a liquid delivery system cap device, including a movable sensor means and a motor configured to move the movable sensor means.

The devices, system, and techniques described herein may provide one or more of the following advantages. First, some embodiments describe herein include a cap device that can facilitate accurate and repeatable measurements related to a liquid delivery device. For example, a sensor carriage carrying a sensor component (and/or that is movable with limited or no manual user operation) can promote a consistent travel velocity and/or acceleration that facilitates consistent and predictable sensor signals. User influence on the dynamics of the sensor carriage may be reduced, and manufacturing design tolerances that may result in clearance play or other inadvertent movement of the sensor carriage during operation of the sensor carriage can be reduced.

Second, some embodiments described herein may facilitate accurate and repeatable measurements related to the liquid delivery device by using a combination of sensor types. In some embodiments, the cap device includes one or more optical sensors together with a position sensor, such as a linear potentiometer, optical encoder, rotary encoder, magnetic potentiometer, membrane potentiometer, load cell, etc., for example. The combination of such sensor types facilitates accurate evaluation of relative positions of various features of the liquid delivery device and/or a change in position of various features during subsequent scans of the liquid delivery device.

Third, the cap device may promote efficient and cost-effective manufacturing and assembly processes by including relatively few sensors. In some embodiments, the cap device includes one or two liquid delivery device sensors (e.g. plunger sensors), such as one or two optical sensors, and a position sensor, such as a linear potentiometer, optical encoder, rotary encoder, magnetic potentiometer, membrane potentiometer, etc. Such configurations thus include relatively few sensors, and reduce the number of assembly and/or calibration steps that otherwise may be appropriate to assemble many sensors into the cap device.

Fourth, various embodiments described herein may include a cap device compatible with a variety of liquid delivery device types. For example, the cap device may facilitate accurate and repeatable measurements even when used with distinct liquid delivery device types that may have varying shapes, sizes, and features that interact differently with the sensors and other features of the cap device. One or more optical sensors of the sensor carriage may be oriented to obtain predetermined lines of sight that promote reliable plunger detection for a variety of different liquid delivery device types. For example, optical sensors may be arranged so that at least one optical sensor is positioned to detect the plunger, even if another optical sensor is obstructed by a feature of the liquid delivery device at a particular instance.

Fifth, some cap devices described herein improve the user experience of a liquid delivery system by automating some actions related to dose measurement and management. For example, the cap device may deliver output that informs a user of a previously delivered dose of the liquid, a duration since the previous dose, a number of doses remaining, a volume of liquid remaining, an expected life remaining of the liquid delivery device.

Sixth, in some optional embodiments, cap devices described herein may improve the user experience of a liquid delivery system by facilitating semi-automatic or automatic operation. For example, little or no manual operation may be required beyond engaging the cap device with the liquid delivery device. In some optional embodiments including a movable sensor carriage, the sensor carriage may be brought into a first position by engagement of the cap device onto the liquid delivery device, and the sensor carriage may be automatically released such that the sensor carriage can move from the first position to the second position while operating to scan the liquid delivery device.

Seventh, some embodiments described herein facilitate a durable cap device that can operate over an extended period of time and/or that may be used with many liquid delivery devices. For example, a single cap device may be reusable with many disposable liquid delivery devices. The sensors of the cap device, such as one or more plunger sensors and position sensors, such as one or more optical sensors, load sensors, linear potentiometers, optical encoders, rotary encoders, magnetic potentiometers, membrane potentiometers etc., may be configured to have consistent and/or predictable output over the operational life of the cap device.

Eighth, some embodiments described herein provide controlled sensor movement that may provide reliable and repeatable detection. For example, a motorized drive system may drive a sensor carriage substantially independent of manual input or movement. In some embodiments, a motorized drive system may drive a sensor carriage at a varied speeds, in multiple directions, etc. to improve detection. Alternatively or additionally, movement of the sensor carriage may be delayed a predetermined period of time after engagement between the cap device and liquid delivery device to facilitate measurement while the system is subject to little or no movement or external forces.

The details of one or more implementations are set forth in the accompanying drawings and the description below. Other features and advantages will be apparent from the description and drawings, and from the claims.

DESCRIPTION OF DRAWINGS

FIGS. 10A and 10B show an example sensor carriage including arms in an extended or engaged configuration.

FIGS. 10C and 10D show an example sensor carriage including arms in a retracted or disengaged configuration.

DETAILED DESCRIPTION OF ILLUSTRATIVE EMBODIMENTS

Figure 1:
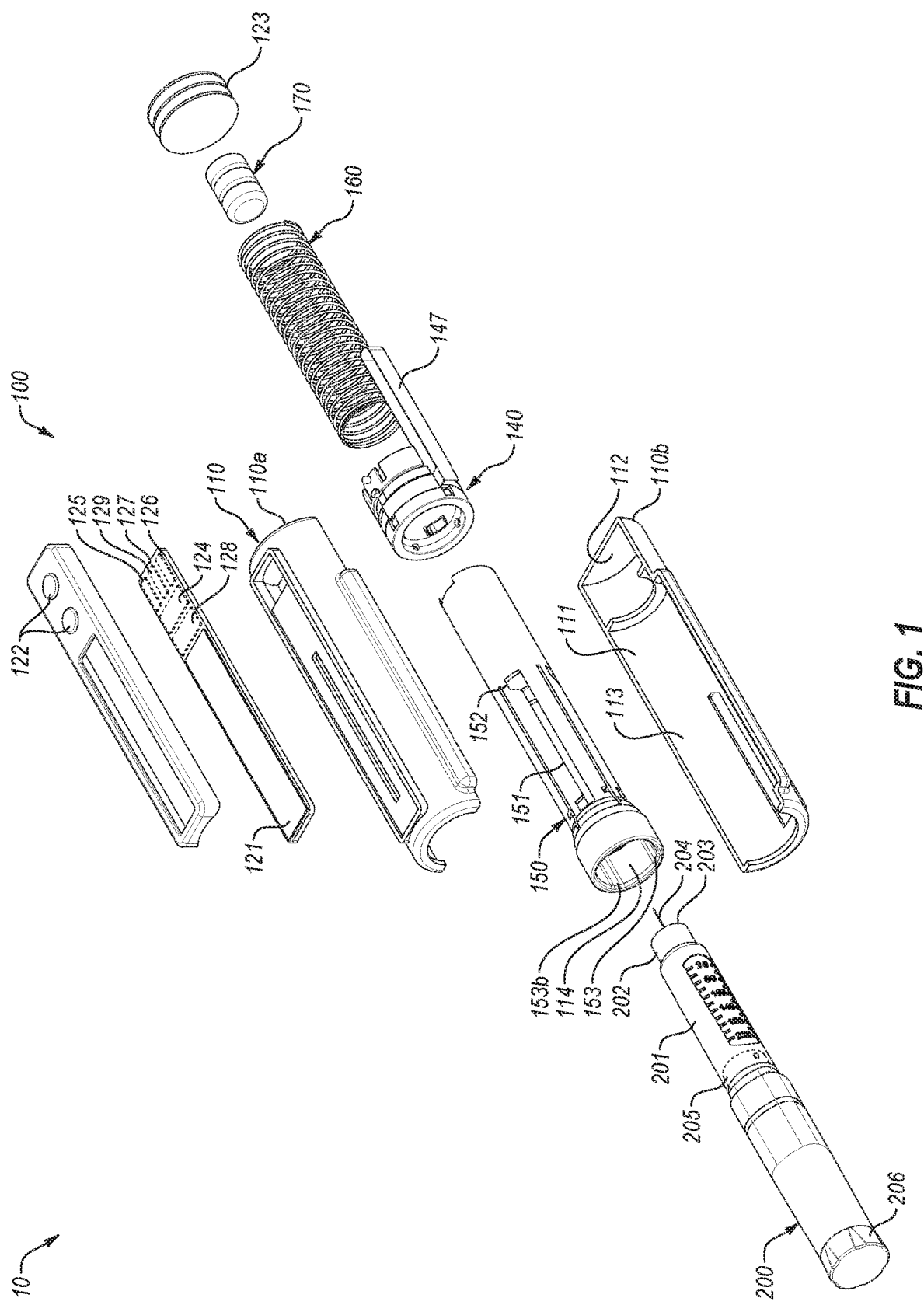
FIG. 1 is an exploded perspective view of an example liquid delivery system including a cap device.
Figure 2:
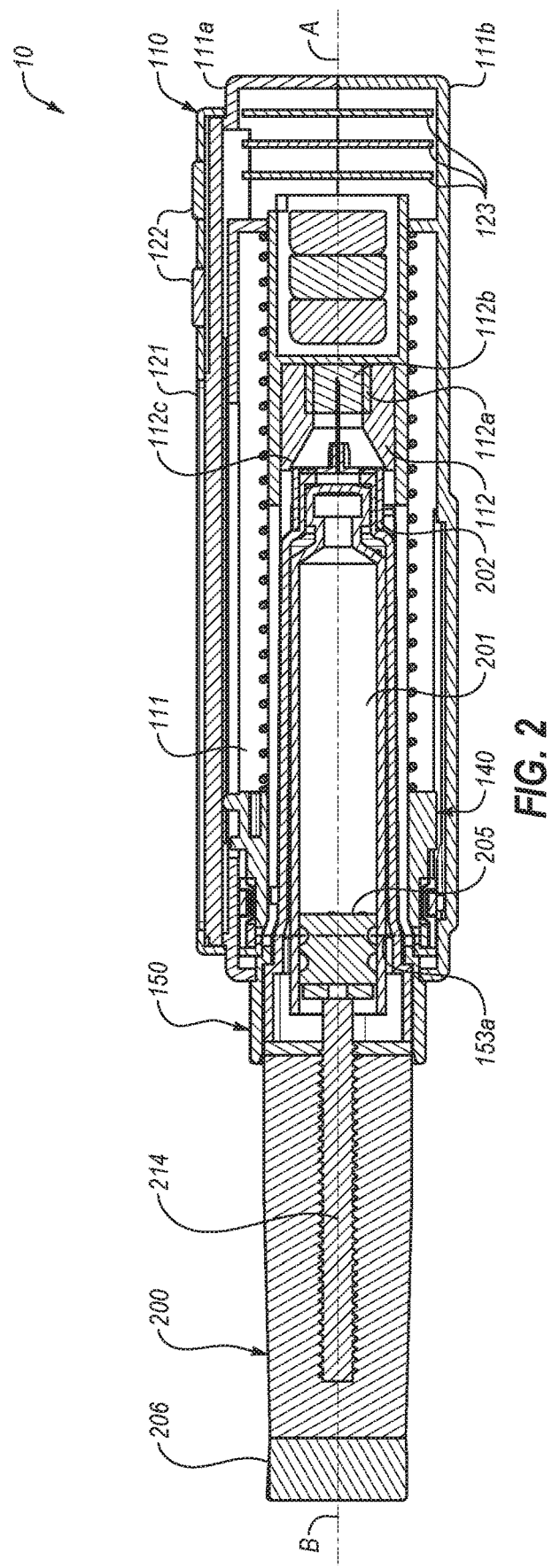
FIG. 2 is a cross-sectional view of the example liquid delivery system of FIG. 1.

Referring to FIGS. 1 and 2, an example liquid delivery system 10 is shown that can be used to store and deliver a liquid, and output dosage information to a user. Liquid delivery system 10 includes cap device 100 and liquid delivery device 200. Liquid delivery device 200 includes a reservoir 201, delivery end 202, and a plunger 205 that can be operated to deliver a dose of the liquid within reservoir 201 through delivery end 202. Cap device 100 is positionable over delivery end 202 of liquid delivery device 200 for storage of liquid delivery device 200 between uses. In an example embodiment, cap device 100 includes one or more sensors configured to detect a condition of liquid delivery device 200, such as a position of its plunger, and one or more output devices, such as a display, communication system, etc., configured to output information related to the condition of liquid delivery device 200.

Liquid delivery device 200 may be configured to deliver a measured dose of a liquid to a subject for the treatment of a medical condition. For example, liquid delivery device 200 may be a pen injector for delivering a liquid, such as insulin, to manage diabetes. In an example embodiment, delivery end 202 of liquid delivery device 200 includes a septum 203 and an injection needle 204. A desired dosage may be measured by operation of dial 206 (e.g. by manually rotating dial 206), and delivered by advancing plunger 205. Advancement of plunger 205 via rod 214 pushes the measured dosage of liquid from reservoir 201, through delivery end 202, and into the subject. In an example embodiment, advancement of plunger 205 a particular distance causes a corresponding volume of liquid to be dispensed from liquid delivery device 200.

Cap device 100 includes a body 110 that defines a cavity 111 configured to receive at least a portion of liquid delivery device 200, such as at least a portion of delivery end 202 and/or reservoir 201. Cap device 100 is positionable over delivery end 202 and may retain liquid delivery device 200 (e.g. between periods of use). Cap device 100 may protect delivery end 202 from damage or contaminants of the external environment, and contain injection needle 204. Liquid delivery device 200 may be removed from cavity 111 of cap device 100 before each use, and subsequently engaged with cap device 100 after a dose has been delivered. Cap device 100 may thus be removed from and replaced onto liquid delivery device 200 over multiple uses. After the contents of a particular liquid delivery device 200 has been exhausted, the liquid delivery device 200 may be discarded, and cap device 100 used with a new liquid delivery device. In some example embodiments, liquid delivery device 200 is disposable when its usable contents are exhausted, and cap device 100 may be reusable with multiple liquid delivery devices 200. In other example embodiments, cap device 100 may be associated with a particular liquid delivery device 200, and both the cap device 100 and the liquid delivery device 200 may be disposed when the contents of reservoir 201 are exhausted.

Cap device 100 may include one or more sensors configured to detect a condition of liquid delivery device 200. In an example embodiment, cap device 100 includes sensors that output sensor signals that may be evaluated to detect plunger 205, a position of plunger 205, a change in position of plunger 205 between successive engagements with cap device 100 (e.g. a change in position after delivery of a dose), and/or other conditions of liquid delivery device 200. The position of plunger 205, and/or the change in the position of plunger 205, may be used to monitor a volume of a dose delivered by liquid delivery device 200, a remaining total volume of liquid within reservoir 201, a remaining number of doses within reservoir 201, a remaining duration until reservoir 201 is emptied, and/or other information related to liquid delivery device 200.

Cap device 100 may include various components that facilitate calculation, display, storage, and/or communication of sensor signals that may be output by the one or more sensors. In an example embodiment, cap device 100 includes a display 121, user inputs 122, communication device 123, memory 124, processor 125, speaker 126, and circuit board 127. One or more components may be in electrical communication with one or more other components via circuit board 127, and processor 125 may be configured with logic to control operation of one or more of display 121, user inputs 122, communication device 123, memory 124, and speaker 126, and to process sensor signals received from one or more sensors of cap device 100.

Display 121 provides a visual output to a user related to a condition of cap device 100 and/or liquid delivery device 200. Display 121 may be an LED or LCD display, for example. In some embodiments, display 121 may provide a visual indication related to a volume of a dose delivered by liquid delivery device 200, a remaining total volume of liquid within reservoir 201, a remaining number of doses within reservoir 201, a remaining duration until reservoir 201 is emptied, a time of the previous dose (e.g. a time the cap device 100 was replaced on liquid delivery device 200), an elapsed time since the last dose (e.g. an elapsed time since cap device 100 was replaced on liquid delivery device 200), and/or other information related to liquid delivery device 200.

Alternatively or additionally, cap device 100 may include audio and/or vibratory alerts related to a condition of cap device 100 and/or liquid delivery device 200. Processor 125 may control audio output of speaker 126 to output an audible alert, or vibrator 128 to output a vibratory alert, which may be perceived as an indication of a volume of a dose delivered by liquid delivery device 200, a remaining total volume of liquid within reservoir 201, a remaining number of doses within reservoir 201, a remaining duration until reservoir 201 is emptied, a time of the previous dose (e.g. a time the cap device 100 was replaced onto liquid delivery device 200), an elapsed time since the last dose (e.g. an elapsed time since cap device 100 was replaced onto liquid delivery device 200), and/or other information related to liquid delivery device 200. Alternatively or additionally, vibrator 128 may deliver vibrations to liquid delivery device 200. Vibrator 128 may be activated to facilitate mixing of the contents of liquid delivery device 200 and/or to reduce the formation or buildup of precipitates (e.g. on the leading surface of plunger and/or surfaces of reservoir 201).

Cap device 100 optionally includes one or more user inputs 122 that facilitate user interaction with cap device 100. In an example embodiment, user inputs 122 include first and second buttons that may be operated to control cap device 100. For example, user inputs 122 may be operated by a user to activate cap device 100 and/or select information to be displayed by display 121. Alternatively or additionally, user inputs 122 may be operated to reset settings and/or memory 124 of cap device 100, such as when cap device 100 is engaged with a new liquid delivery device 200. In some example embodiments, cap device 100 does not include user inputs 122, such as buttons. Cap device 100 that does not include buttons or other user inputs may promote the perception of a fully automated cap device 100 and/or improve user operability.

Cap device 100 may communicate with one or more other components of a liquid delivery system to deliver and/or receive information related to a condition of cap device 100 and/or liquid delivery device 200. For example, cap device 100 includes a communication device 123 configured to communicate with one or more components remote from cap device 100. Communication device 123 may include a wireless communication printed circuit assembly configured for wireless communication, such as via short-wavelength UHF radio frequency, RF communication, WI-FI, BLUETOOTH, ZIGBEE, etc. Alternatively or additionally, communication device 123 may include an electrical port for wired communication with another electronic device. In various example embodiments, communication device 123 is configured for two-way communication, such as two-way communication with a mobile device having software configured to deliver and receive communications with cap device 100. Alternatively, cap device 100 may be configured for one-way communication, such as only to upload information to the mobile device, or only to receive information from the mobile device.

Communication device 123 may be configured to communicate with an electronic device configured with diabetes management software. For example, communication device 123 may transmit information related to liquid delivery device 200 that may be further processed by the electronic device. In this way, cap device 100 may facilitate review of information collected by its sensors by a remote user or healthcare provider, provide alerts related to liquid delivery system 200 by the electronic device (e.g. related to a scheduled time for an injection, a nearly empty liquid delivery device, etc.), and/or facilitate additional processing and analysis of the information collected by cap device 100.

Cap device 100 includes a power source 170. In an example embodiment, power source 170 comprises one or more batteries, such as alkaline batteries, nickel cadmium batteries, lithium ion batteries, etc. Power source 170 may be associated with a micro-switch configured to switch cap device between an inactive or low power state to an active or operational state in which sensors of cap device 100 are active. Alternatively or additionally, a sensor signal from one or more sensors of cap device 100, such as one or more position sensors, may provide an alert to processor 125 to switch cap device to the active or operational state.

Still referring to FIG. 1, body 110 of cap device 100 defines cavity 111 configured to receive at least a portion of liquid delivery device 200. Body 110 may be configured to house various components of cap device 100, such as display 121, user inputs 122, communication device 123, memory 124, processor 125, speaker 126, and circuit board 127. In various example embodiments, body 110 is a molded body, such as a molded plastic. Body 110 may include multiple body portions that are assembled to from body 110, such as a first body portion 110a and a second body portion 110b that may be joined to define cavity 111 and/or other spaces to accommodate components of cap device 100. A body 110 that includes first and second body portions 110a, 110b may facilitate efficient manufacturing of body 110 and/or efficient assembly with other components of cap device 100. In other example embodiments, the portion of body 110 that defines cavity 111 may be integrally formed as a unitary component (e.g. such that multiple components do not need to be joined in order to define cavity 111).

Body 110 includes a front wall 112, side walls 113, and an opening 114 to cavity 111. Cavity 111 is at least partially defined by front wall 112 and side walls 113. Front wall 112 includes a feature configured to receive delivery end 202 and/or injection needle 204 of liquid delivery device 200, such as a receptacle 112a including plug 112b (FIG. 2) that at least partially surrounds injection needle 204. Alternatively or additionally, front wall 112 may include one or more retention features that engage with liquid delivery device 200 and limit relative movement between liquid delivery device 200 and body 110 of cap device 100.

In some optional embodiments, cap device 100 includes sensor carriage 140 that is movable within body 110 (e.g. movable within cavity 111). Sensor carriage 140 is configured to travel along at least a portion of liquid delivery device 200 within cavity 111, and cavity 111 is sized to accommodate the dimensions of liquid delivery device 200 and a path for sensor carriage 140. Sensor carriage 140 facilitates detection of characteristics of liquid delivery device 200 by carrying one or more sensors along liquid delivery device between a first position and a second position. In an example embodiment, sensor carriage 140 is movable between the first position and the second position relative to the cavity while liquid delivery device 200 remains in a fixed position relative to the cavity (e.g. the sensor carriage 140 is movable while the liquid delivery device 200 is fixedly engaged with cap device 100).

Cap device 100 may include a track 150. Sensor carriage 140 may travel along track 150, and track 150 may include one or more features that guide and/or limit the movement of sensor carriage 140. In an example embodiment, track 150 includes one or more slots 151 that interact with a complementary feature of sensor carriage 140. Slots 151 define a path that sensor carriage 140 travels along, such as in a longitudinal direction between a first position proximate front wall 112 and a second position closer to opening 114. In some embodiments, slots 151 include keyed end regions 152 that allow movement of sensor carriage 140 or a component of sensor carriage 140 in one or more additional directions, such as rotation of sensor carriage 140, or a component of sensor carriage 140 (e.g. such that a sensor carried by carriage 140 does not rotated), about the central longitudinal axis (A) of cavity 111.

In some embodiments, track 150 includes one more features configured to interact with features of liquid delivery device 200. For example, interior surfaces 153 of track 150 may include features that orient and/or retain liquid delivery device 200 within cap device 100. Track 150 may at least partially surround reservoir 201 of liquid delivery device, and sensor carriage 140 may be movable between track 150 and side walls 113 that define cavity 111 of cap device 110. Thus, in an example embodiment, track 150 is positioned between liquid delivery device 200 and sensor carriage 140 during operation of sensor carriage 140.

In some embodiments, track 150 may be integrally formed with body 110 of cap device 100. For example, track 150 may be integrally formed with body 110 as a unitary component. Alternatively, track 150 may be formed as a component separate from other components of body 110 and subsequently assembled with the other components of body 110. A separately formed track 150 may facilitate manufacture of track 150 (e.g. which may optionally have tighter manufacturing tolerances and/or include features otherwise difficult to form within cavity 111 of body 110).

Sensor carriage 140 is movable along a longitudinal axis of cap device 100 (e.g. a longitudinal axis extending centrally through front wall 112 and opening 114) and/or may be rotatable (e.g. a component of sensor carriage 140 may be rotatable) about the longitudinal axis at particular locations. When cap device 100 engaged with liquid delivery device 200, sensor carriage 140 may travel along at least a portion of liquid delivery device 200, such as between delivery end 202 to a position beyond plunger 205, for example. In an example embodiment, cap device 100 includes a spring 160 configured to move sensor carriage 140 from a first position to a second position. For example, spring 160 may be manually compressed as sensor carriage 140 is moved into a first position proximate the front wall 112 of body 111. The sensor carriage 140 may be moved into the first position when liquid delivery device 200 is inserted into cavity 111 (e.g. liquid delivery device 200 may push sensor carriage into the first position), and sensor carriage 140 may be subsequently released to move to a second position proximate opening 114 of body 111 when released (e.g. independent of liquid delivery device 200). In various example embodiments, spring 160 is a coil spring. Alternatively or additionally, spring 160 may be an elastic band, wire, elastic component, or other component configured to bias sensor carriage 140 towards a particular position.

In various example embodiments, liquid delivery device 200 remains in a fixed position relative to cavity 111 and body 110 of cap device 100 while sensor carriage 140 travels along liquid delivery device 200. Liquid delivery device 200 is constrained against twisting or rotation about longitudinal axis A of cavity 111, and/or may be constrained from longitudinal movement along longitudinal axis A. Limited or no relative movement between liquid delivery device 200 and body 110 facilitates accurate and repeatable detection of plunger 205 by sensors of sensor carriage 140, and provides a predictable line of sight for the sensors of sensor carriage 140.

In some example embodiments, sensor carriage 140 includes one or more sensor components configured to detect a condition of liquid delivery device 200 (e.g. as the sensor carriage moves between the first position and the second position). Sensor carriage 140 may include components of a plunger detection sensor, such as a reflective optical sensor or a transmissive optical sensor, and/or a position sensor, such as a load sensor, linear potentiometer, linear encoder, rotary encoder, magnetic potentiometer, or membrane potentiometer, for example, configured to detect information that can be used to evaluate a condition of liquid delivery device 200.

Referring now to FIG. 2, a cross-sectional view of liquid delivery system 10 is shown, including cap device 100 retained on liquid delivery device 200. Delivery end 202 and at least a portion of reservoir 201 of liquid delivery device 200 are positioned within cavity 111 of cap device 110. Front wall 112 includes engagement features configured to align and/or engage delivery end 202. For example, front wall 112 includes a tapered or chamfered wall portion 112c that may direct delivery end 202 towards a centered location within cavity 111. Alternatively or additionally, engagement features 112c interact with a complementary surface of delivery end 202 to frictionally retain delivery end 202. For example, wall portion 112c may include one or more ribs, detents, etc. to retain liquid delivery device 200 in a fixed position within cavity 111.

Body 110 may include one or more features that orient and align liquid delivery device 200 relative to body 110 (e.g. as the liquid delivery device 200 is inserted into cavity 111). For example, interior surfaces 153 of track 150 and/or side walls 113 may include a tapered portion 153a proximate opening 114 such that a leading portion of track 150 is wider than an interior portion of track 150. Tapered portion 153a may facilitate manual insertion of liquid delivery device 200 into cavity 111 by directing liquid delivery device 200 towards a central location within body 110. In some embodiments, tapered portion 153a may guide central longitudinal axis B of liquid delivery device 200 into alignment with central longitudinal axis A of cavity 111. Alternatively or additionally, track 150 and/or side walls 113 may include one or more rotational alignment features 153b (FIG. 1) that guide liquid delivery device 200 into one or more predetermined angular orientations. In this way, features of liquid delivery device 200 may be guided towards a predetermined angular position relative to cap device 100 and its sensors, such as sensors located on sensor carriage 140.

Figure 3:
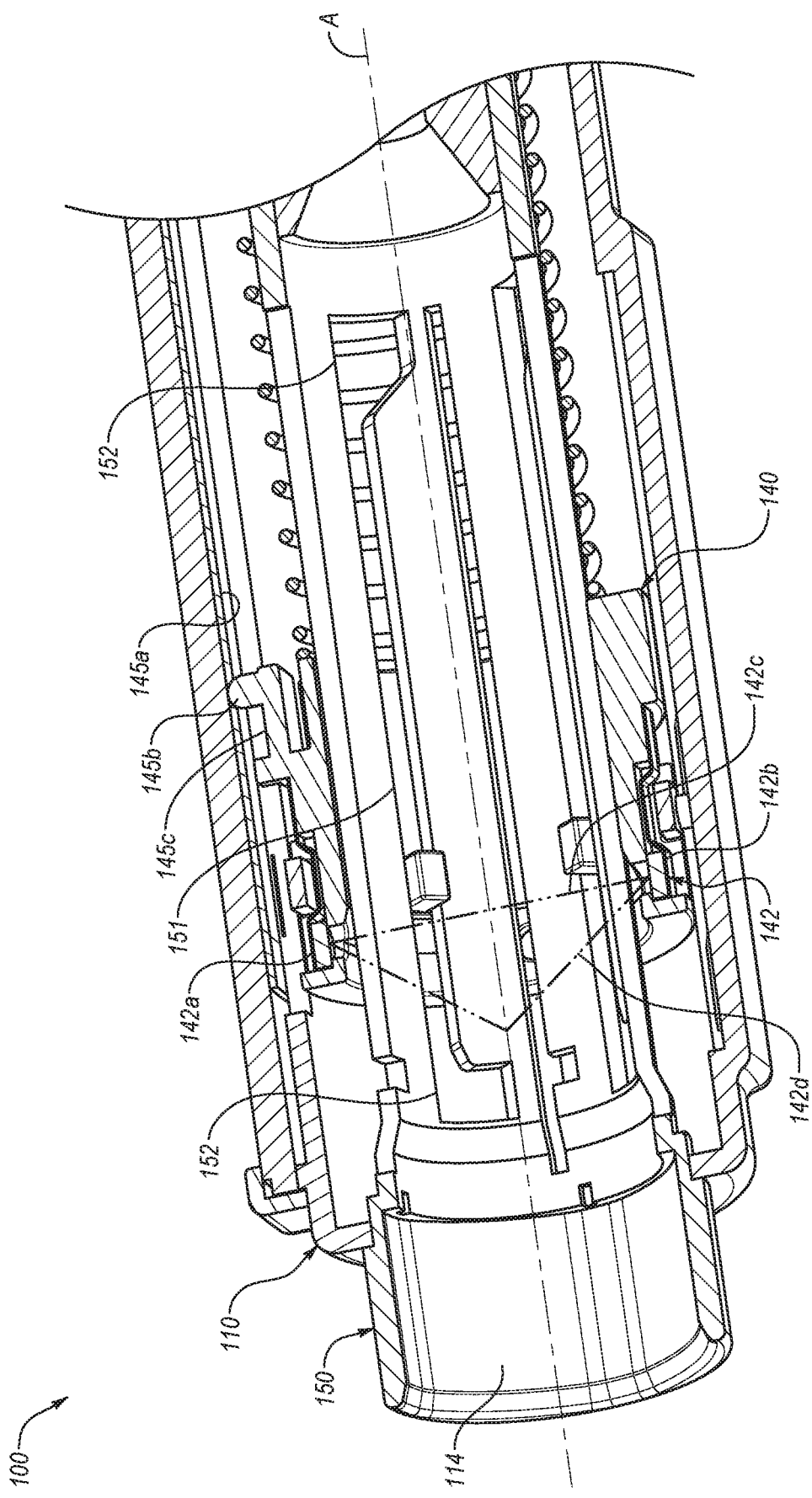
FIG. 3 is a partial cross-sectional view of the example liquid delivery system of FIG. 1, showing a sensor carriage including one or more sensor components.
Figure 4:
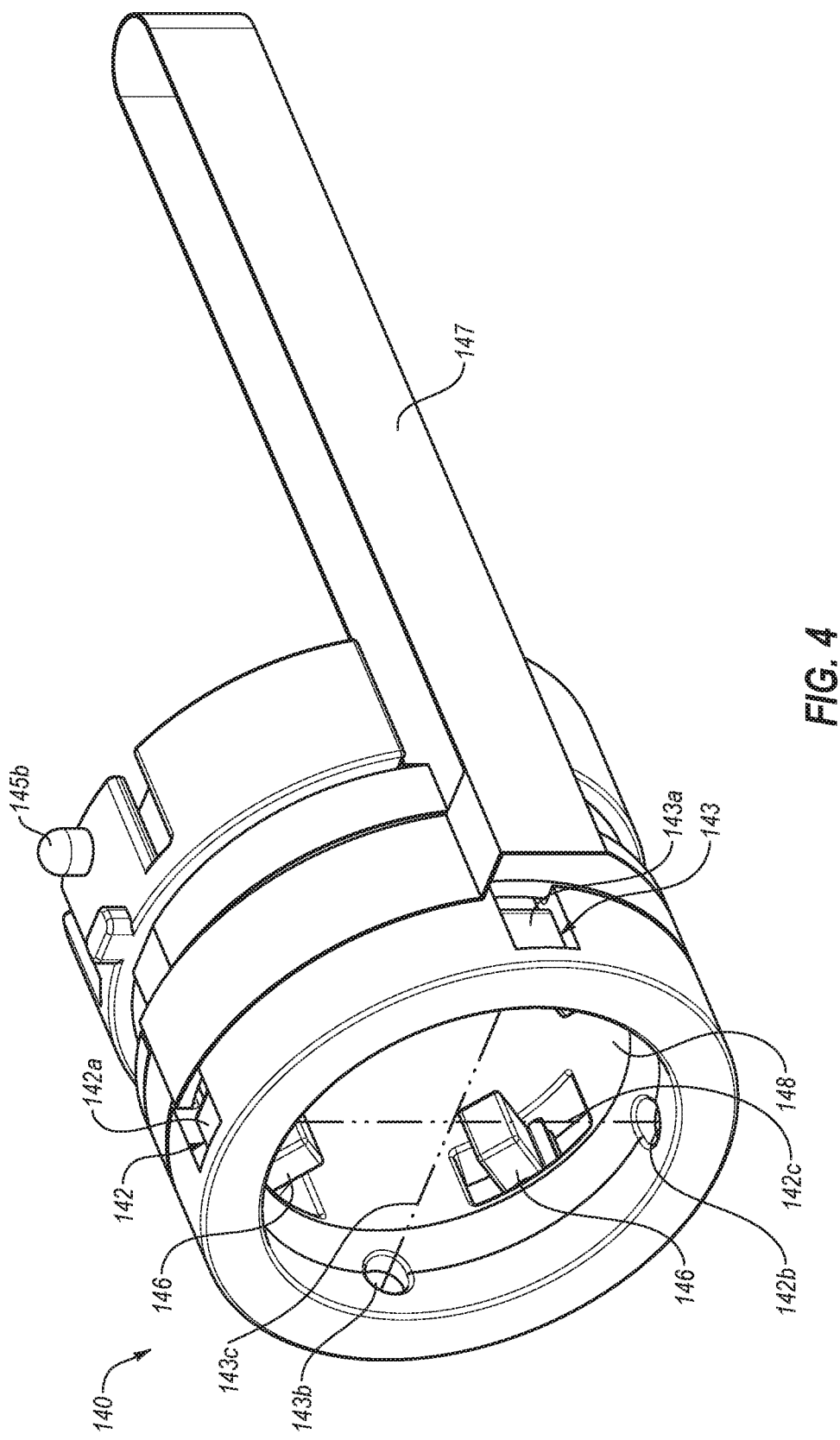
FIG. 4 is a perspective view of the sensor carriage of the example liquid delivery system of FIG. 1.

Referring now to FIGS. 3 and 4, an example sensor carriage 140 is shown that is movable within body 110 of cap device 100. FIG. 3 shows a cross-sectional view of sensor carriage 140 within cap device 100, and FIG. 4 shows a perspective view of sensor carriage 140. Sensor carriage 140 includes one or more sensor components configured to detect a condition of liquid delivery device 200, such as a position of a plunger within liquid delivery device 200. For example, sensor carriage 140 includes a sensor 142 that outputs a sensor signal representative of a characteristic of liquid delivery device 200. The output signal from sensor 142 may vary depending on a physical characteristic of liquid delivery device 200 encountered by sensor 142, and thus the output signal may differ at different positions along a length of liquid delivery device 200. For example, as sensor carriage 140 moves relative to liquid delivery device 200, a change in the output signal of sensor 142 may be evaluated to determine a leading end of reservoir 201 (e.g. at delivery end 202), a leading end of plunger 205, a trailing end of plunger 205, and/or other attributes of liquid delivery device 200. A change in position detected between a series of doses, such as a change in position of plunger 205 before and after a dose has been delivered, may be used to evaluate a volume of a dose delivered by liquid delivery device 200, a remaining total volume of liquid within reservoir 201, a remaining number of doses within reservoir 201, a remaining duration until reservoir 201 is emptied, a time of the previous dose (e.g. a time the cap device 100 was replaced on liquid delivery device 200), an elapsed time since the last dose (e.g. an elapsed time since cap device 100 was replaced on liquid delivery device 200), and/or other information related to liquid delivery device 200. Alternatively or additionally, the relative positions of one or more of these detected characteristics, or a distance between one or more of these detected characteristics, may be used to evaluate dosage information related to liquid delivery device 200.

In an example embodiment, sensor 142 includes an emitter 142a and a receiver 142b, such as an optical emitter 142a and optical emitter 142b. Optical emitter 142a emits radiation that can be detected by optical receiver 142b, and in some embodiments may include an LED or laser diode. Sensor 142 may output a sensor signal related to the amount of radiation received by optical receiver 142b (e.g. an amount of radiation received from optical emitter 142a). The sensor signal may thus depend on the features of liquid delivery device 200 present in path 142c between optical emitter 142a and optical received 142b. The amount of radiation received by optical receiver may thus be relatively lower when a plunger or other solid structure is present in path 142c, and may be relatively higher when only transparent walls of a reservoir and its liquid contents are present in path 142c, for example.

Emitter 142a and receiver 142b may be arranged in alignment with one another such that an optical path 142c between emitter 142a and receiver 142b extends perpendicular (e.g. substantially perpendicular, within 10° of exactly perpendicular) to the central longitudinal axis A of cavity 111. In some embodiments, emitter 142a is configured to generate a narrow beam with limited spread outside of optical path 142c, such as by an emitter 142a that emits a narrow beam and/or by a collimating structure configured to focus the output of emitter 142a along path 142c. In various example embodiments, radiation emitted by emitter 142a may be within visible and/or invisible wavelengths.

In some example embodiments, sensor 142 may be a reflective sensor that detects reflected light. Reflective sensor 142 may detect a color transition indicative of plunger 205, such as transition from a relatively higher transparency and/or light color of liquid and/or reservoir 201 to the relatively lower transparency and/or dark color of plunger 205 (e.g. red, orange, black, etc.).

Sensor carriage 140 may include multiple sensors, such as first and second optical sensors 142, 143 (FIG. 4). First optical sensor 142 includes first emitter 142a and first receiver 142b, and second optical sensor 143 includes second emitter 143a and second receiver 143b. First emitter 142a may be aligned with first receiver 142b and second emitter 143a aligned with second receiver 143b (e.g. such that first receiver 142b receives radiation primarily or exclusively from first emitter 142a and second receiver 143b receives radiation primarily or exclusively from second emitter 143a). For example, first emitter 142a and second receiver 143b, and second emitter 143a and first receiver 142b, are not in alignment and do not define an optical path perpendicular to the longitudinal axis of cavity 111. In an example embodiment, first and second emitters 142a, 142b, and first and second receivers 143a, 143b, are spaced 90° from each other around a perimeter of sensor carriage 140. Accordingly, first sensor 142 and second sensor 143 may define first and second paths 142c, 143c oriented perpendicular to one another. In some embodiments, first path 142c and/or second path 143c do not intersect with a central longitudinal axis (A) of cavity 111 or a central longitudinal axis (B) of liquid delivery device 200. First and/or second paths 142c, 143c that do not intersect the central axis may facilitate detection of trailing surface 205b of plunger 205 by avoiding obstruction by rod 214.

In various example embodiment, the relative locations of sensors 142 and 143 may be selected to promote an appropriate line of sight (e.g. through liquid delivery device 200) by at least one of sensor 142 or sensor 143. The relative locations of sensors 142, 143 may be selected based on the features of liquid delivery device 200, such as the locations of ribs, indicia, and other obstructions that could affect reliable detection of features of liquid delivery device 200, such as plunger 205 or delivery end 202. In some example embodiments, first and second paths 142c, 143c may form an angle between 15° and 90°, 30° and 75°, or about 60°. Alternatively or additionally, first and second sensors 142, 143 may be spaced along sensor carriage 140 in a longitudinal direction.

The paths of sensors 142, 143, may be angled relative to central longitudinal axes (A), (B) of cavity 111 and liquid delivery device 200. Angled sensor paths may facilitate detection of a plunger at a location within an opaque region of liquid delivery device 200, such as during initial usage of liquid delivery device 200 while reservoir 201 remains full or nearly full. For example, angled sensor paths may allow detection of the plunger without sensor carriage 140 itself traveling to a longitudinal position of plunger 205. In this way, sensors 142 may detect characteristics of liquid delivery device 200 along a length greater than a length that sensor carriage 140 travels along liquid delivery device 200 between the first and second positions. Sensors 142 may be configured to detect a magnitude of radiation reflected on leading surface 205a of plunger 205. In various example embodiments, plunger 205 may be detected by angled sensor paths 142d, 143d, until between about 10 units and 60 units, 20 units and 40 units, or about 30 units have been dispensed from liquid delivery device 200, for example.

In some embodiments in which multiple optical sensors 142, 143 are present, distinct wavelengths may be emitted by each emitter 142a, 143a, and receivers 142b, 143b may likewise be wavelength-specific, for example, by including a bandpass filter. Alternatively or additionally, each sensor may emit and detect pulses of radiation in distinct time periods of a cycle (e.g. using time-division multiplexing). In some embodiments, sampling rates may be greater than 100 Hz, greater than 1000 Hz, or higher.

Alternatively or additionally to sensors 142, 143, sensor carriage 140 may include a position sensor 145 configured to output a sensor signal indicative of a position or distance. In an example embodiment, cap device 100 includes a position sensor 145 that outputs a sensor signal indicative of a position of the sensor carriage and/or distance the sensor carriage traveled between a first position and a second position (e.g. as sensor carriage 140 moves along liquid delivery device 200 or between subsequent doses of liquid delivery device 200). In an example embodiment, position sensor 145 includes a linear potentiometer. A resistive element 145a is located at least partially along a length of cavity 111, such as side wall 113 of body 110 or track 150. A wiper 145b is located on sensor carriage 140. Wiper 145b may be biased towards resistive element 145a by an elastic element 145c, such as a spring arm or spring (FIG. 3) to promote continuous contact between resistive element 145a and wiper 145b. In some embodiments, the elastic element 145c provides a relatively low bias such that wiper 145b remains in contact with resistive element 145a while frictional resistance or wear of resistive element 145a is reduced.

Sensor 145 may output a sensor signal (e.g a voltage) that varies depending on the position of wiper 145b along resistive element 145a (e.g. and a position of sensor carriage 140 along cavity 111). For example, a particular voltage may be associated with a particular location along resistive element 145a, and the voltage may be consistent and repeatable each time wiper 145b travels along resistive element 145a. Sensor 145 may have a unique signature of voltage outputs for each location of wiper 145b, and can be calibrated to achieve highly precise and repeatable measurements. In some example embodiments, the resolution of sensor 145 may be between 1 μm and 30 μm, 2 μm and 15 μm, 3 μm and 10 μm, or about 6 μm, and the resolution of liquid delivery device 200 may be about 130 μm. The resolution of sensor 145 of cap device 100 may thus be between about 10 to 20 times the resolution of liquid delivery device 200. Such resolutions of sensor 145 facilitate a highly accurate determination of a position of plunger 205, with a level of error contributed by the sensor that is an order of magnitude smaller than variation in dose delivery by liquid delivery device 200, for example.

In some embodiments, the precision and repeatability of sensor 145 may be further enhanced by accounting for variation that may occur due to ambient temperature changes. For example, cap device 100 may include a temperature sensor 129 (FIG. 1) that detects a temperature and outputs a temperature signal to processor 125. Processor 125 may account for a change in temperature when evaluating sensor signals received from sensor 145 based on a predetermined relationship between temperature and sensor signals from sensors 142, 143, 145, etc.

Alternatively or additionally to a linear potentiometer, position sensor 145 may include one or more other sensor types that provide an indication of position that can be correlated with an sensor signal output by sensor 142. For example, position sensor 145 may include a linear encoder, rotary encoder, magnetic potentiometer, membrane potentiometer, load cell, etc., for example.

In an example embodiment, processor 125 is configured to evaluate sensor signals from sensors 142 and/or 143, such as a variation in sensor signals indicative of the plunger, and to determine a corresponding position based on the sensor signal from sensor 145. In some embodiments, the corresponding position may be stored and compared to a corresponding position of plunger 205 during a subsequent measurement. A change in position may then be evaluated to determine the volume of the previously delivered dose (e.g. by evaluating the distance traveled by plunger 205). In some example embodiments, only a change in position of plunger 205 is evaluated, and the position of plunger 205 relative to other components of liquid delivery device 200 and/or cap device 100 is not evaluated.

Alternatively or additionally, the position of plunger 205 relative to a feature of liquid delivery device 200 and/or cap device may be evaluated. For example, processor may be configured to detect a sensor signal output from sensors 142, 143 indicative of a leading end of reservoir 201, and to determine a corresponding position based on the output signal from sensor 145. The relative positions of such features may be evaluated to determine a distance between the leading end of reservoir 201 and plunger 205, which in turn may facilitate calculation of a remaining total volume of liquid within reservoir 201, a remaining number of doses within reservoir 201, a remaining duration until reservoir 201 is emptied, and/or other information related to liquid delivery device 200.

Sensor carriage 140 may be electrically connected with processor 125 to facilitate electrical communication of sensor signals. In some embodiments, a flexible electrical connector 147 provides electrical connection at least partially between sensor carriage 140 and circuit board 127 that supports processor 125. Flexible electrical connector may include conductive electrical structures on a thin, flexible substrate. For example, the flexible electrical connector may include one or more layers of PEEK, polyester, or polyamide having printed or laminated electrical structures. The flexible electrical connector thus may have a thin profile that facilitates bending to a small radius of curvature. The flexible electrical connector may bend and flex while the sensor carriage 140 travels along track 150, while maintaining electrical connection with circuit board 127 and/or processor 125.

Alternatively or additionally, track 150 may include one or more electrical conductors that provide electrical communication between sensor carriage 140 and circuit board 127 while sensor carriage 140 travels along track 150. For example, sensor carriage 140 may have a fixed electrical contact biased towards sliding engagement with a complementary electrically conductive surface of track 150.

In some embodiments, sensor carriage 140 is not in continuous electrical connection with circuit board 127 and/or processor 125. For example, sensor carriage 140 may operate to detect a condition of liquid delivery device 200 while not in electrical communication with circuit board 127 and/or processor 125. Sensor carriage 140 may include a power source that can deliver power to one or more sensors carried by sensor carriage 140, and a sensor carriage memory to store sensor signal information. The sensor carriage 130 may store sensor information collected as it travels between the first and second positions, and may be brought into electrical communication with circuit board 127 and/or processor 125 when stopped at the first and/or second positions to upload the collected information to memory 124.

Still referring to FIGS. 3 and 4, sensor carriage 140 includes engagement features configured to interact with track 150 and/or liquid delivery device 200. In some optional embodiments, arms 146 of sensor carriage 140 may guide sensor carriage 140 along slots 151. Arms 146 extend at least partially into slots 151 so that sensor carriage 146 is limited to movement in a path directed by slots 151, and rotation of sensor carriage 140 is prevented. Slots 151 may include a substantially straight portion parallel to central longitudinal axis A of cavity 111. Alternatively or additionally, slots 151 may include curved or helical portions that cause sensor carriage 140 and/or track 150 to rotate relative to one another and/or other components of cap device 140 as sensor carriage 140 travels along cavity 111.

Figure 5A:
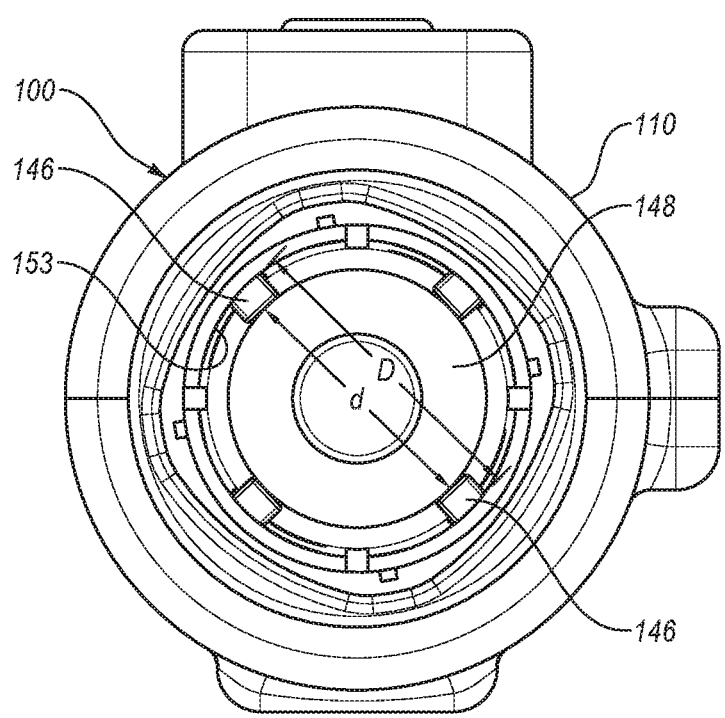
FIG. 5A is an end view of the cap device of the example liquid delivery system shown in FIG. 1.
Figure 5B:
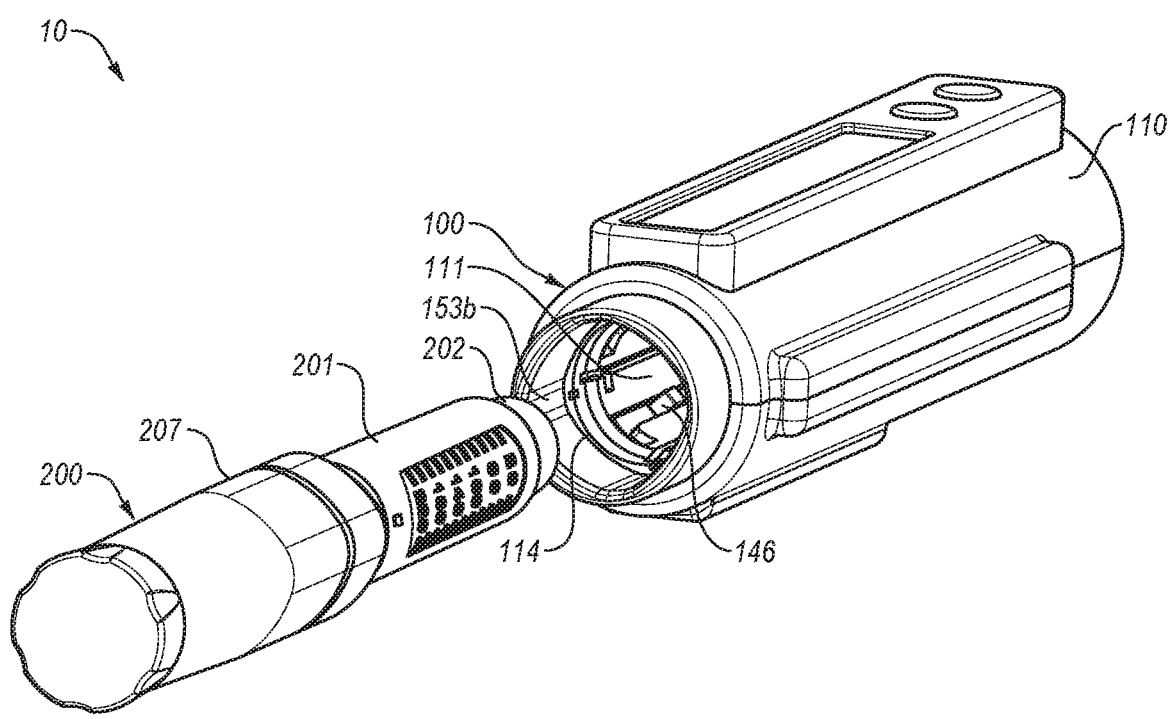
FIG. 5B is a perspective view of the liquid delivery system of FIG. 1.
Figure 5C:
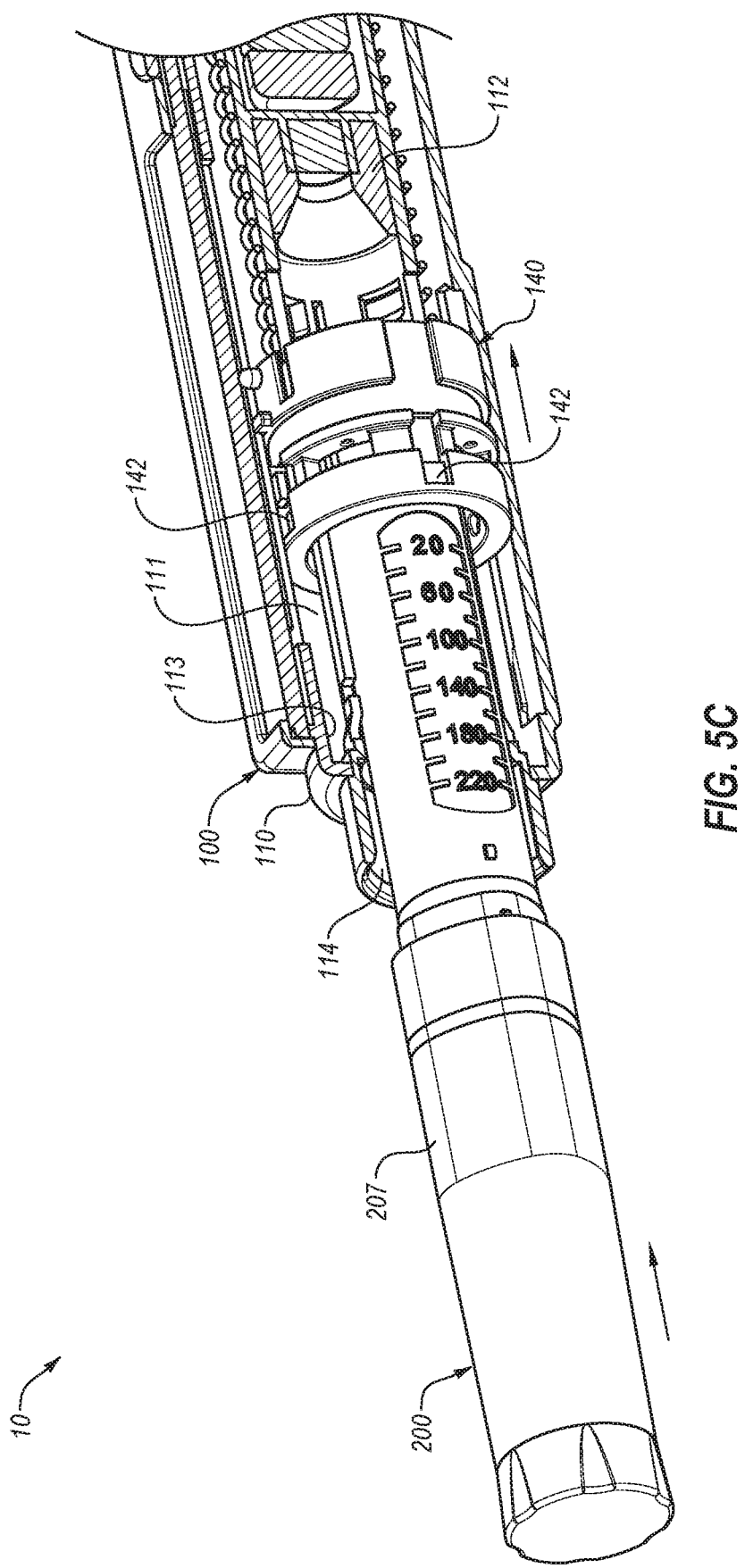
FIG. 5C is a partial cross-sectional view of the example liquid delivery system of FIG. 1, showing movement of the sensor carriage as the liquid delivery device is received in the cavity of the cap device.

Referring now to FIGS. 5A, 5B, and 5C, sensor carriage 140 includes one or more engagement features configured to interact with liquid delivery device 200. For example, sensor carriage 140 includes arms 146 that can be pushed by liquid delivery device 200 to move sensor carriage 140. When liquid delivery device 100 is inserted into cavity 111, interference between arms 146 and liquid delivery device 200 causes sensor carriage 140 to move with liquid delivery device 200 towards front wall 112 of body 110. Arms 146 may subsequently be moved out of engagement with liquid delivery device 200 (e.g. by retracting, releasing, rotating, etc.) to release sensor carriage 140 to return towards opening 114 of cavity 111 while liquid delivery device 200 remains in a fixed position relative to cavity 111 of cap device 100. In some embodiments, spring 160 may be compressed when liquid delivery device 200 is fully inserted into cavity 110, and spring 160 may return sensor carriage 140 towards opening 114 when arms 146 are released from engagement with liquid delivery device 200.

Referring to FIG. 5A, in an example embodiment, sensor carriage includes four arms 146 radially spaced around a circumference of sensor carriage 140. Arms 146 are movably between an extended position in which arms 146 extend into a bore 148 defined by sensor carriage 140 (e.g. extending inwardly away from an interior wall of sensor carriage 140), and a retracted position. For example, track 150 includes a major diameter (D) between opposing interior surfaces 153, and a minor diameter (d) between opposing arms 146 in the extended position. Major diameter (D) may be slightly larger than an outer diameter of liquid delivery device 200 such that sensor carriage 140 can travel along the liquid delivery device 200. Minor diameter (d) may be slightly smaller than an outer diameter of liquid delivery device 200, such that sensor carriage 140 can be pushed by liquid delivery device 200 via extended arms 146. When arms 146 are in the retracted position, diameter (d) between opposing arms 146 may be greater than major diameter (D) such that sensor carriage 140 can travel along the liquid delivery device 200 without interference with arms 146.

Referring to FIGS. 5B and 5C, cap device 100 is engageable with liquid delivery device 200 by insertion of delivery end 202 through opening 114 of body 110 and into cavity 111. As liquid delivery device 200 is inserted through opening 114, delivery end 202 encounters engagement features of sensor carriage 140, such as arms 146 in an extended position. As shown in FIG. 5C, relative movement between cap device 100 and liquid delivery device 200 (e.g. as cap device 100 and liquid delivery device 200 are brought together) results in liquid delivery device 200 pushing sensor carriage 140 into cavity 111. For example, liquid delivery device 200 pushes sensor carriage 140 along track 150 from a position proximate opening 114 to a position proximate front wall 112, compressing spring 160.

Body 110 and liquid delivery device 200 may include one or more features that orient and align liquid delivery device 200 to body 110. In an example embodiment, at least a portion of liquid delivery device 200 includes a non-circular and/or asymmetric cross-section that can be accommodated in cavity 111 in a discrete number of orientations. Liquid delivery device 200 includes a non-circular body portion 207 having a generally square or rectangular cross-section such that liquid delivery device 200 is position able within cavity 111 in one of four orientations. In other example embodiments, non-circular body portion 207 may have a triangular, pentagonal, polygonal, or other shape. Alternatively or additionally, liquid delivery device 200 may include one or more protrusions or recesses that interact with complementary recesses or protrusions of cap device 100 to dictate a predetermined angular orientation between liquid delivery device 200 and cap device 100 when engaged. The cross-sectional shape, protrusions, and/or recesses may promote a predetermined angular orientation during engagement, and maintain the predetermined angular orientation while cap device 100 is engaged with liquid delivery device 200. The locations and relative angular orientations of sensors 142, 143 in cap device 100 may be selected to facilitate a predetermined path between sensor emitters and receivers (e.g. that reduces obstruction by ribs, indicia, or other features of liquid delivery device 200) based on the predetermined angular orientation of liquid delivery device 200.

Track 150 and/or side walls 113 of cap device 100 may include one or more rotational alignment features 153b that guide liquid delivery device 200 towards the predetermined angular orientation. For example, features of liquid delivery device 200 may be guided towards the predetermined angular position relative to cap device 100 and its sensors. Alignment features 153b may interact with body portion 207 after delivery end 202 has been inserted into cavity 111, and may guide liquid delivery device 200 into the predetermined angular orientation.

Figure 6A:
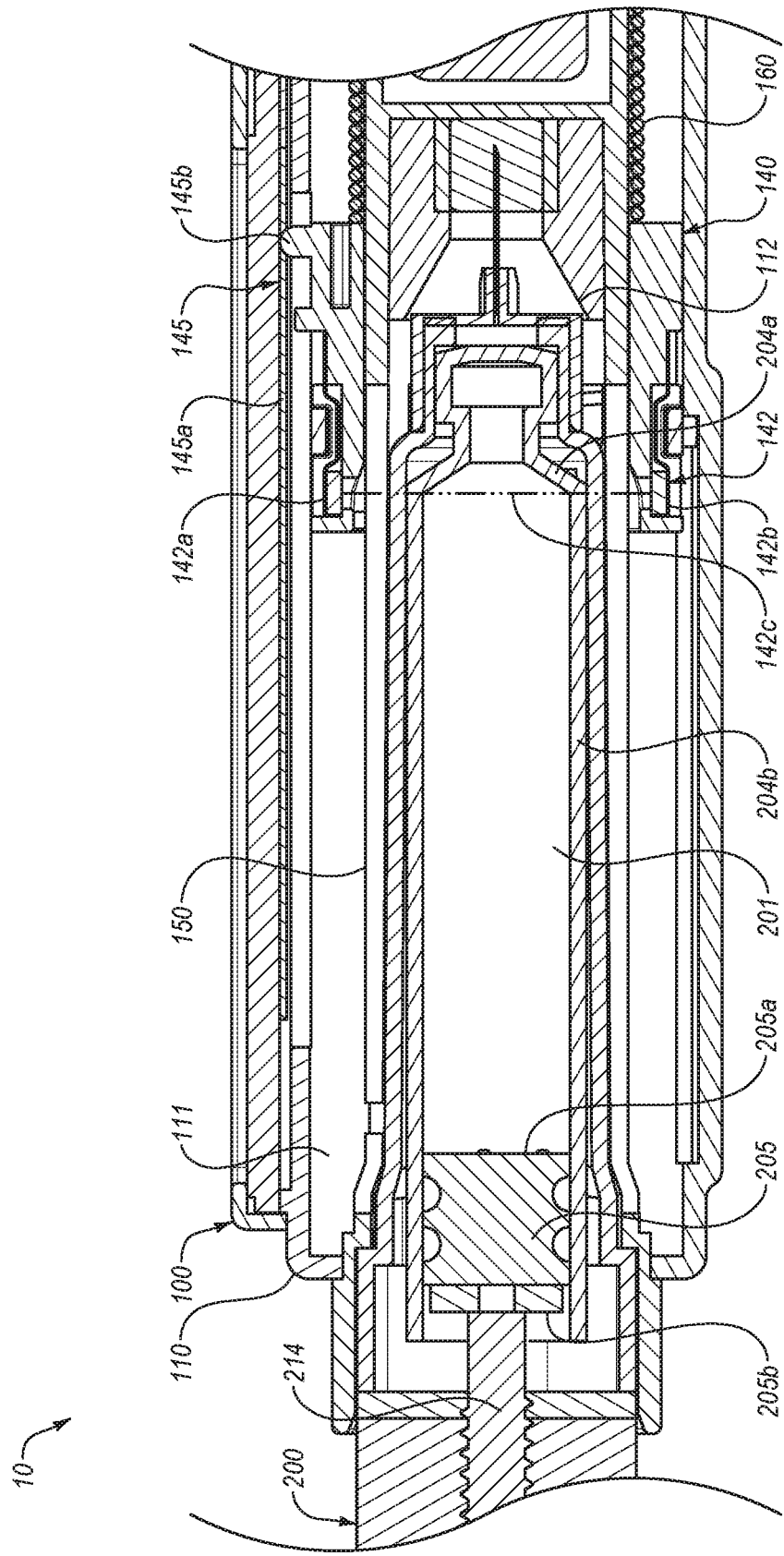
FIGS. 6A-6C show a sensor carriage of the example liquid delivery system of FIG. 1 in a first position, intermediate position, and second position.
Figure 6B:
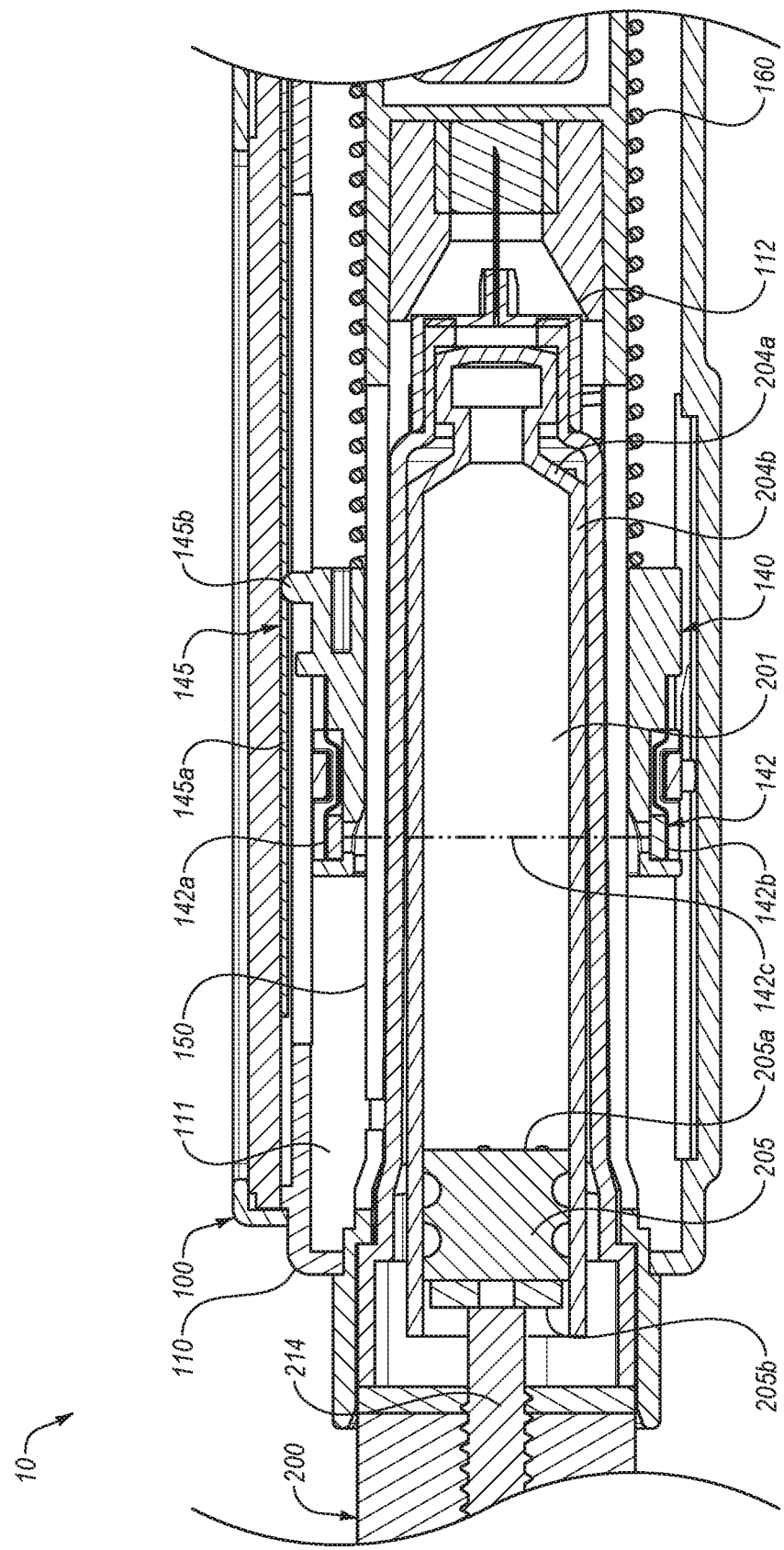
Figure 6C:
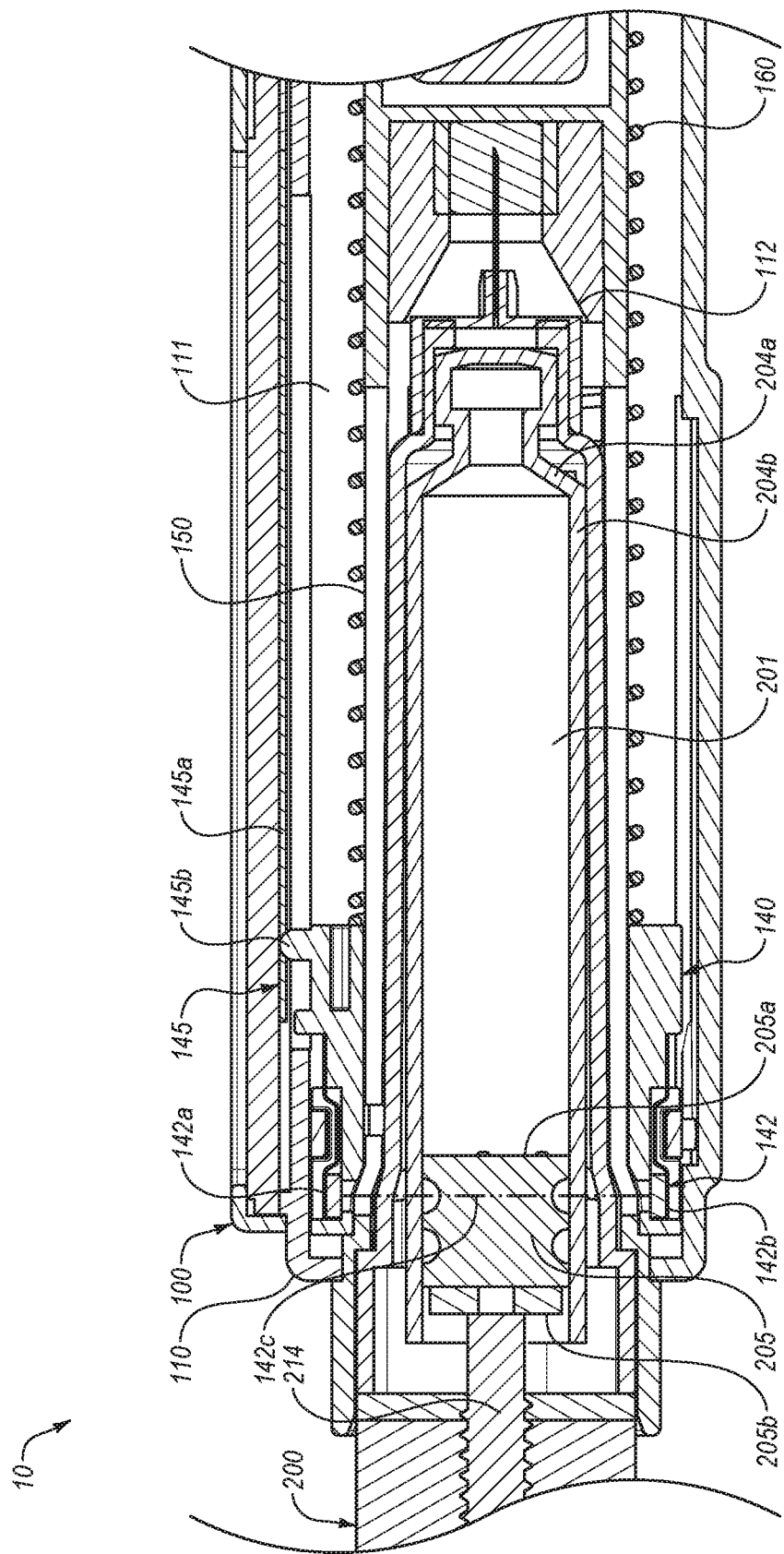

Referring now to FIGS. 6A, 6B, and 6C, movable sensor carriage 140 is shown in a first position (FIG. 6A), intermediate position (FIG. 6B), and second position (FIG. 6C). Sensor carriage 140 is movable between the first, intermediate, and second positions while liquid delivery device 200 remains fixedly positioned relative to body 110 and cavity 111. Movement of sensor carriage 140 between the first and second positions facilitates detection of characteristics of liquid delivery device 200 at multiple locations of liquid delivery device 200. Sensor 142 may generate output signals continuously or at a relatively high frequency (e.g. between 0.1 and 100 kHz, between 5 and 50 kHz, or about 30 kHz) while sensor carriage 140 moves between the first and second positions. In some embodiments, operation of sensor 142 as sensor carriage 140 travels between the first and second positions can be described as generating a scan of a portion of liquid delivery device 200, and the output signals from sensors 142 (e.g. alone or in conjunction with one or more sensors, such as sensor 145) can be evaluated to determine a position of plunger 205 within reservoir 201, a change in position of plunger 205 within reservoir 201, and/or other conditions of liquid delivery device 200.

In the first position shown in FIG. 6A, sensor carriage 140 is located proximate front wall 112 of body 110. Sensor carriage 140 may be brought into the first position by the operation of inserting liquid delivery device 200 within cavity 111. In an example embodiment, spring 160 is in a compressed configuration when sensor carriage 140 is in the first position. Movement of sensor carriage 140 from the first position may be initiated by the release of sensor carriage 140 and/or spring 160. For example, one or more engagement features of sensor carriage 140, such as arms 146, may interact with liquid delivery device 200. Upon reaching the first position, the engagement features may be moved or released such that sensor carriage 140 and liquid delivery device 200 are no longer maintained in a fixed position relative to one another. Sensor carriage 140 may be released upon reaching the first position without additional manual operation. In other example embodiments, sensor carriage 140 may be retained in the first position until released by manual operation (e.g. by manual movement or release of arms 146).

Sensor carriage 140 is movable from the first position towards the second position by spring 160. Spring 160 is biased towards an uncompressed or less compressed configuration in which sensor carriage 140 is located in a second position proximate opening 114 of cavity 111. Spring 160 may be characterized by a spring constant that provides sufficient force to overcome frictional resistance between resistive element 145a and wiper 145b, and between sensor carriage 140, track 150, and/or other components of cap device 100, so that sensor carriage 140 is movable between the first and second positions in a smooth and controlled manner (e.g. with predictable velocity and acceleration). For example, a minimum force of spring 160 (e.g. when extended by sensor carriage 140 in a second position) may be greater than 1N, greater than 1.5N or about 2N. The force of spring 160 is sufficiently low to facilitate robust retention of cap 100 on liquid delivery device 200. For example, a maximum force of spring 160 (e.g. when compressed by sensor carriage 140 in a first position) may be less than about 5N, less than about 4.5N, or about 4N, or lower. Alternatively or additionally, cap device 110 may include a damper configured to provide smooth and consistent motion of sensor carriage 140. For example, sensor carriage 140 may include a rotary damper that interacts with a complementary feature (e.g. a rack) on a component of cap device 140.

Sensor 142 of sensor carriage 140 may output sensor signals as sensor carriage 140 travels between the first and second positions along liquid delivery device 200. In a first position shown in FIG. 6A, path 142c between emitter 142a and receiver 142*b* intersects delivery end 202 of liquid delivery device 200. The sensor signals may be evaluated (e.g. by processor 125) to detect the presence of a leading end of reservoir 201, such as a location immediately reward of tapered walls 204*a*. For example, a magnitude of radiation received by receiver 142*b* may increase or step up between a location at which optical path 142*c* passes through tapered walls 204*a* and a location at which optical path 142*c* passes through walls 204*b* oriented substantially parallel to a longitudinal axis of reservoir 201. In some embodiments, a particular magnitude of the sensor signal, or an increase in the magnitude of the sensor signal, may thus provide an indication of the leading end of reservoir 201.

FIG. 6B shows sensor carriage 140 in an intermediate position between the first and second positions. Optical path 142*c* between emitter 142*a* and receiver 142*b* passes through an intermediate location of reservoir 201. The walls 204*b* of reservoir 201, and the liquid within reservoir 201, may provide relatively lower opacity to transmission of radiation between emitter 142*a* and receiver 142*b*, such that the sensor signals are relatively higher in the intermediate position.

FIG. 6C shows sensor carriage 140 in a second position in which sensor carriage 140 is located proximate opening 114 of cavity 111. In the second position, sensor carriage 140 has traveled beyond leading surface 205*a* of plunger 205 such that path 142*c* intersects plunger 205. The presence of leading surface 205*a* may be detected by a change in the sensor signal at the location path 142*c* encounters leading surface 205*a*. For example, a magnitude of radiation received by receiver 142*b* may be reduced or stepped down due to the presence of plunger 205 in path 142*c*.

Sensor 142 may continue to detect characteristics of liquid delivery device 200 after traveling beyond leading surface 205*a* of plunger 205. For example, a trailing surface 205*b* may be detected based on a change in the sensor output at a location that trailing surface 205*b* intersects path 142*c*. For example, a magnitude of radiation received by receive 142*b* may be increased or stepped up due to the absence of plunger 205 intersecting path 142*c*. The length of plunger 205 between leading surface 205*a* and trailing surface 205*b* is fixed and thus either the leading surface 205*a* or the trailing surface 205*b* may be used to evaluate a position of plunger 205. Detecting both the leading and trailing surfaces 205*a*, 205*b* of plunger 205 may improve the accuracy in evaluating plunger 205. For example, the position of plunger 205 may be accurately located even if a leading or trailing surface 205*a*, 205*b*, is obstructed by another feature of liquid delivery device 200, such as a rib, indicia, etc.

The position of plunger 205 or a change in position of plunger 205 may be evaluated in conjunction with sensor signal output by position sensor 145. In an example embodiment, sensor signals generated by position sensor 145 vary in a predictable manner as sensor carriage 140 moves between the first position and the second position. For example, a sensor signal of position sensor 145 for a particular location may be associated with a sensor signal from sensor 142 at the particular location. A change in position of plunger 205 before and after a dose has been delivered may be detected, and the volume of the delivered dose calculated based on the change in position. Alternatively or additionally, a distance between locations associated with various output signals from sensor 142 may be evaluated, such as a distance between a leading end of reservoir 201 and a leading surface 205*a* of plunger 205, and the remaining volume with reservoir 201 calculated based on the distance.

Figure 7A:
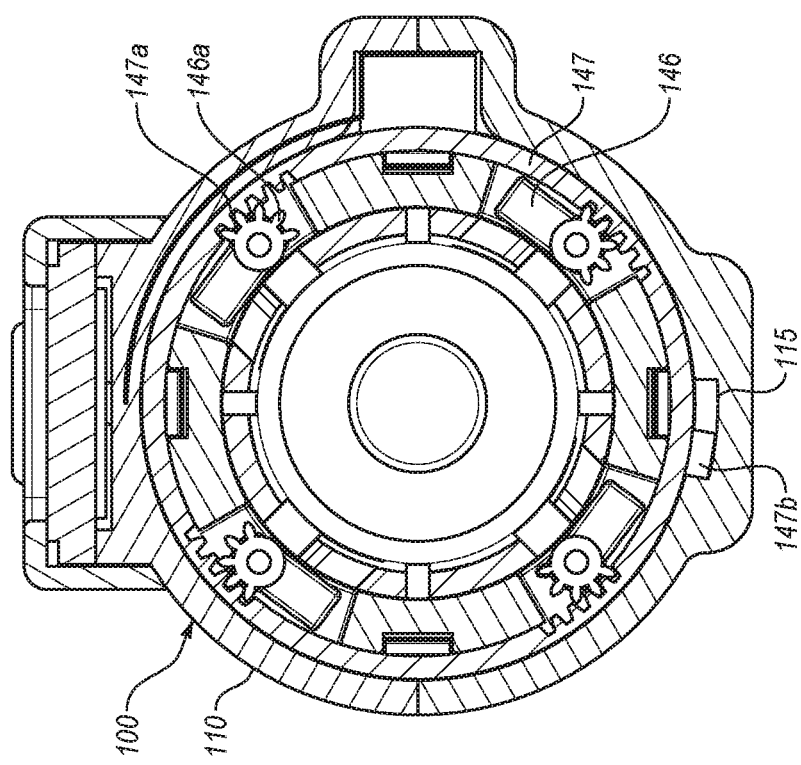
FIG. 7A is a cross-sectional view of the example liquid delivery system of FIG. 1 showing engagement features of the sensor carriage in an extended position.
Figure 7B:
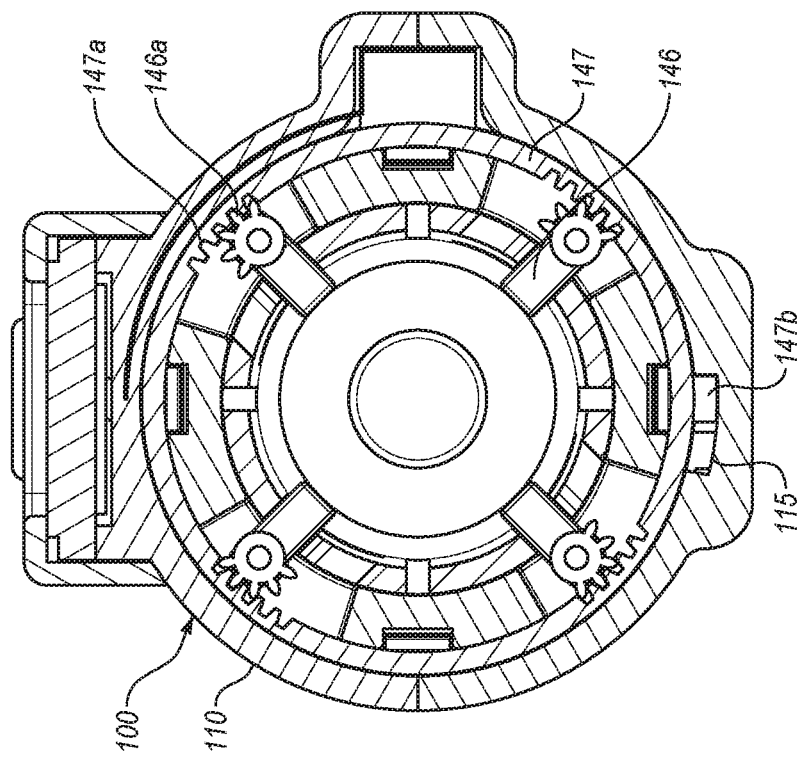
FIG. 7B is a cross-sectional view of the example liquid delivery system of FIG. 1 showing engagement features of the sensor carriage in a retracted position.

Referring now to FIGS. 7A and 7B, engagement features of sensor carriage 140 are shown in an extended or engaged configuration (FIG. 7A) and in a retracted or disengaged configuration (FIG. 7B). In an example embodiment, sensor carriage 140 includes a rotatable ring 147 associated with arms 146. Ring 147 may be rotatable to cause arms 146 to move between the extended and retracted configurations. For example, arms 146 and ring 147 may include complementary features that interact when ring 147 is rotated relative to other components of sensor carriage 140. In some example embodiments, arm 146 and ring 147 include complementary teeth 146*a*, 147*a* that interact similar to a rack and pinion. Rotation of ring 147 in a first direction moves arms 146 from the extended configuration to the retracted configuration, and rotation of ring 147 in a second direction moves arms 146 from the retracted configuration to the extended configuration. In this way, arms 146 are movable between an engaged configuration that facilitates interference with liquid delivery device 200 (e.g. during insertion of liquid delivery device 200 into cavity 111) and a retracted configuration that avoids interference with liquid delivery device 200 (e.g. such that sensor carriage 140 may travel along a portion of liquid delivery device 200 during a plunger detection operation).

Cap device 100 may include features that cause arms 146 to move between the extended and retracted positions when sensor carriage 140 reaches the first and second positions, respectively. For example, in some embodiments, arms 146 are configured to move between extended and retracted positions without additional manual operation beyond insertion of liquid delivery device 200 into cavity 111. Body 110 may include a recess 115 having an angled or ramped surface. Ring 147 includes a protrusion 147*b* engageable with the ramped surface of recess 115. When the protrusion 147*b* encounters the ramped surface (e.g. due to the force of inserting liquid delivery device 200 into cavity 111), ring 147 is caused to rotate in a first direction relative to other portions of sensor carriage 140. Arms 146 in turn are moved to the retracted position shown in FIG. 7B. Movement of arms 146 to the retracted position (e.g. when cap device 100 is engaged on liquid delivery device 200 and sensor carriage 140 is in the first position proximate front wall 112) may release sensor carriage 140 such that spring 160 causes sensor carriage 140 to travel along liquid delivery device 200 from the first position to the second position. Alternatively or additionally, rotation and or movement may occur in part due to interaction with a spring, spring arm, etc.

Slots 151 of track 150 may include widened end regions 152 (FIG. 3) that facilitate or direct movement of arms 146 between extended and retracted positions. For example, widened end regions may provide additional clearance for rotation of arms 146. Alternatively or additionally, widened end regions 152 may include a ramped surface or other feature engageable with sensor carriage 140 that causes arms 146 to move between engaged and retracted configurations. Slots 151 may be configured to prevent or limit rotation or disengagement of arms 146 while the sensor carriage 140 moves between first and second positions.

Figure 8:
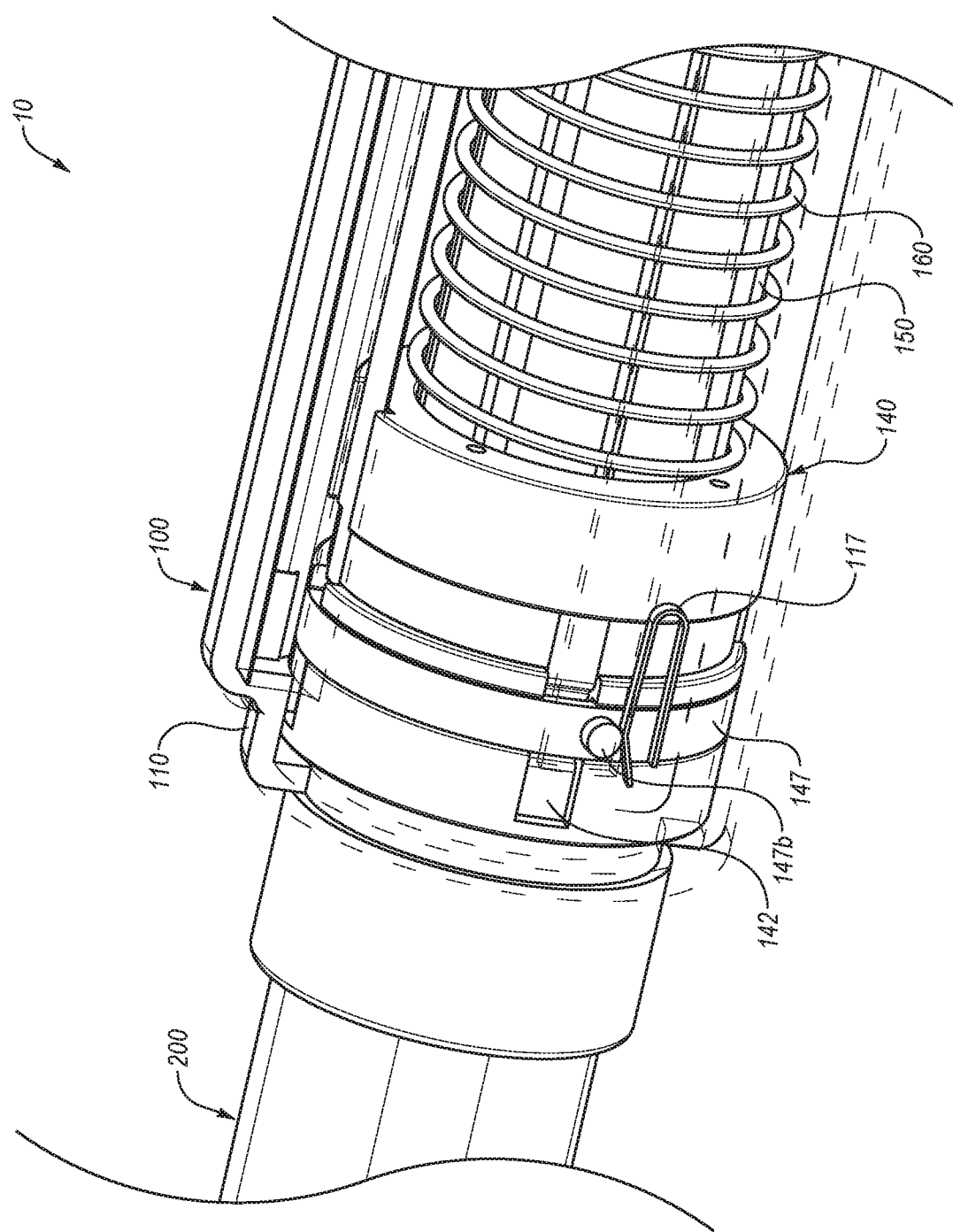
FIG. 8 is a partial cross-sectional view of the example liquid delivery system of FIG. 1, including a rotation feature of the cap device.

In some example embodiments, body 110 may include one or more features that cause ring 147 to rotate in a second direction relative to other portions of sensor carriage 140 when sensor carriage 140 reaches a second position proximate opening 114 (e.g. reaches the second position due to movement caused by spring 160). Referring now to FIG. 8, cap device 100 may include a spring 117 that interacts with ring 147 when sensor carriage 140 is in the second position. Spring 117 is biased to cause ring 147 to rotate in the second direction and, in turn, cause arms 146 to return to the extended configuration. The presence of liquid delivery device 200 within cavity 111 prevents arms 146 from moving to the extended position, and thus ring 147 may be forced to rotate by spring 117 only upon removal of liquid delivery device 200.

In an example embodiment, rotation of ring 147 and/or movement of engagement features such as arms 146 between extended and retracted positions may occur without manual operation beyond insertion and removal of liquid delivery device 200. For example, insertion of liquid delivery device 200 moves sensor carriage 140 into the first position and subsequently releases sensor carriage 140 to scan liquid delivery device 200 while traveling from the first position to a second position. Removal of liquid delivery device 200 from cavity 111 allows arms 146 to return to an extended position in which cap device 100 is ready to again receive liquid delivery device 200. Accordingly, in various example embodiments, cap device 100 is configured to repeatedly and reliably scan liquid delivery device 200 to determine the location of plunger 205, and evaluate subsequent plunger positions to determine various characteristics of liquid delivery device 200 and its use.

Figure 9B:
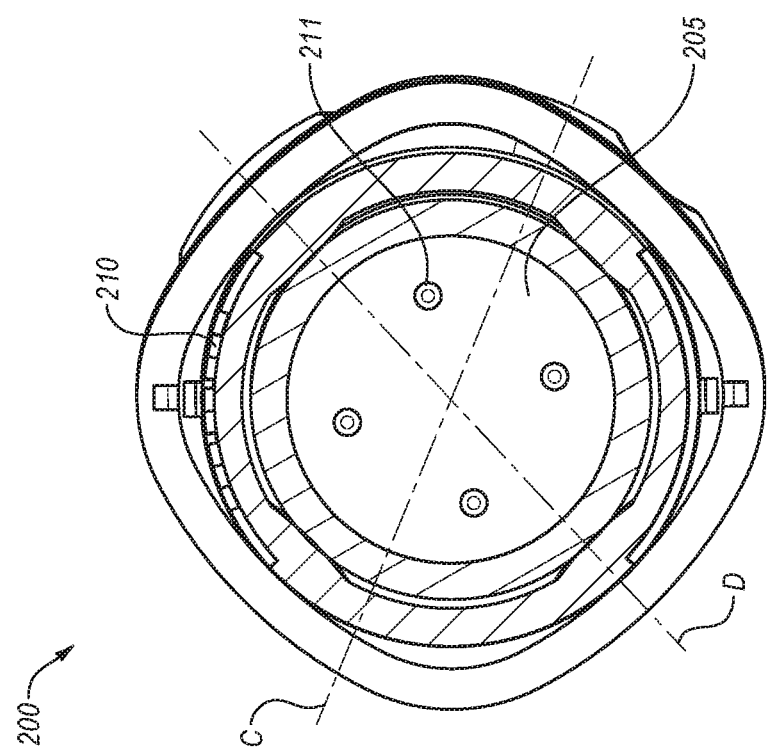
FIG. 9B is a cross-sectional view of the example liquid delivery device of FIG. 9A.
Figure 9A:
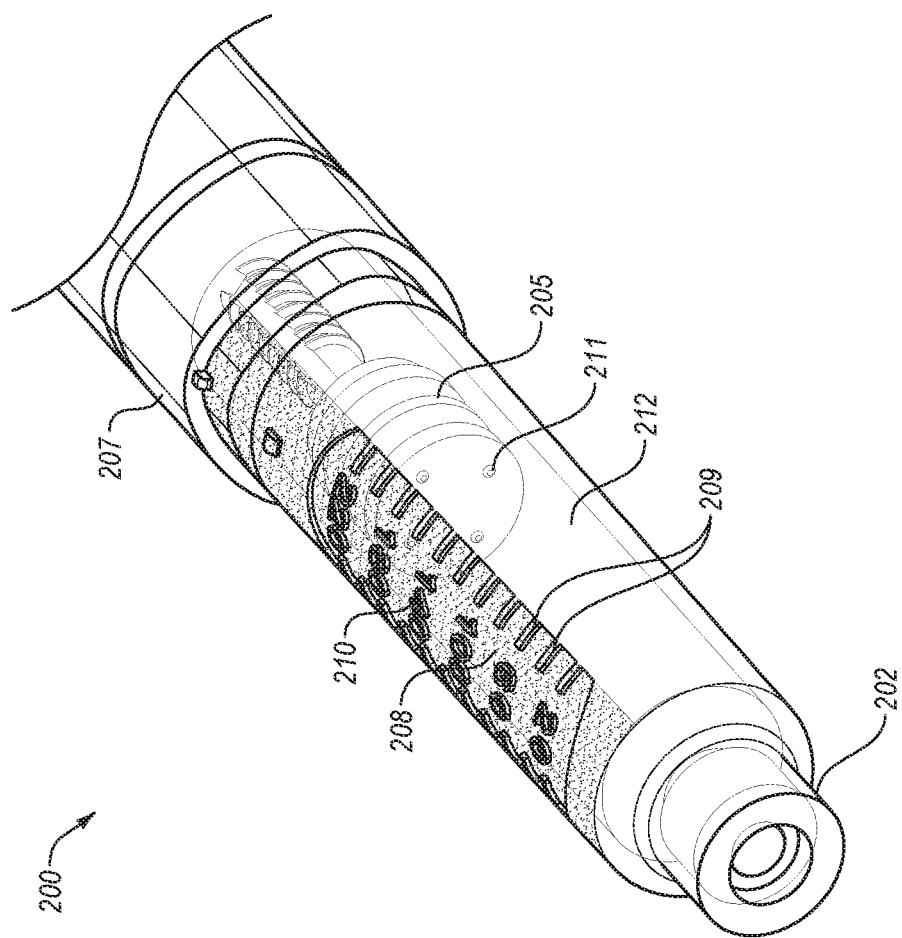
FIG. 9A is a partial perspective view of an example liquid delivery device.

Referring now to FIGS. 9A and 9B, a partial perspective view and a cross-sectional view of an example liquid delivery device 200 are shown. Liquid delivery device 200 includes various features that may affect the sensor signal of a sensor, such as sensor 142. For example, liquid delivery device 200 may include a region 208 having relatively higher opacity, ribs 209, indicia 210, and/or other features that allow relatively lower transmission of radiation utilized by sensors 142, and a region 212 having relatively lower opacity. Such features may act as an obstruction, and/or result in a sensor signal that is similar to a sensor signal generated when plunger 205 is encountered, or a signal that is not otherwise usable for an accurate measurement. Similarly, plunger 205 may include bumps or protrusions 211 on its leading surface.

In various example embodiments, such features can be avoided and/or accounted for by a predetermined angular orientation of cap device 100 and liquid delivery device 200. As shown in FIG. 9B, liquid delivery device 200 includes paths (C), (D) through region 212 having relatively lower opacity. Alternatively or additionally, paths (C), (D) avoid intersection with one or more of region 208 having higher opacity, ribs 209, and/or indicia 210. In an example embodiment, cap device 100 may be configured to orient liquid delivery device 200 such that a sensor path of at least one sensor, such as path 142c of sensor 142, is aligned similar to paths (C) or (D) to avoid intersection with such features. For example, sensor carriage 140 having two sensors 142, 143 offset from one another (e.g. in the configuration shown in FIG. 4) facilitates alignment of at least one sensor path through region 212. The sensor signals output by sensors 142, 143 can be processed to reliably distinguish plunger 205 from one or more other features of liquid delivery device 200. Alternatively or additionally, sensor signals output by sensors 142, 143 can be processed to account for the presence of bumps or protrusions 211 (e.g. by evaluating a series of sensor signals from each of sensors 142, 143). Accordingly, reliable and repeatable detection of plunger 205 may be achieved by accounting for one or more other features of liquid delivery device 200, and/or maintaining liquid delivery device 200 in a fixed longitudinal and angular position relative to cap device 100 during operation.

Referring now to FIGS. 10-11, an example liquid delivery system 50 is shown that can be used to store and deliver a liquid. Liquid delivery system 50 includes cap device 700 and liquid delivery device 900. Liquid delivery device 900 includes a reservoir 901, delivery end 902, and a plunger 905 that can be operated to deliver a dose of the liquid within reservoir 901 through delivery end 902. Cap device 700 is positionable over delivery end 902 of liquid delivery device 900 for storage of liquid delivery device 900 between uses. In an example embodiment, cap device 700 includes one or more sensors that may be configured to detect a condition of liquid delivery device 900, such as a position of its plunger, and one or more output devices, such as a display, communication system, etc., configured to output information related to the condition of liquid delivery device 900. In some example embodiments, liquid delivery system 50 includes features and characteristics similar to features and characteristics of liquid delivery system 10 described above with reference to FIGS. 1 through 9.

Cap device 700 may include one or more sensors configured to detect a condition of liquid delivery device 900. In an example embodiment, cap device 700 includes sensors that output sensor signals that may be evaluated to detect a plunger, a position of the plunger, a change in position of the plunger between successive engagements with cap device 700 (e.g. a change in position after delivery of a dose), and/or other conditions of liquid delivery device 900. The position of the plunger, and/or a change in the position of the plunger, may be used to monitor a volume of a dose delivered by liquid delivery device 900, a remaining total volume of liquid within reservoir 902, a remaining number of doses within reservoir 902, a remaining duration until reservoir 902 is emptied, and/or other information related to liquid delivery device 900.

In some embodiments, cap device 700 includes a sensor carriage 740 that is movable within body 710 (e.g. movable within cavity 711 between walls of body 710 and bore 748 where a liquid delivery device is positioned). Sensor carriage 740 is configured to travel along at least a portion of liquid delivery device 900 within cavity 711, and cavity 711 is sized to accommodate the dimensions of liquid delivery device 900 and a path for sensor carriage 740. Sensor carriage 740 facilitates detection of characteristics of liquid delivery device 900 by carrying one or more sensors along liquid delivery device between a first position and a second position. Sensor carriage 740 is optionally movable between the first position and the second position relative to the cavity 711 while liquid delivery device 900 remains in a fixed position relative to the cavity 711 (e.g. the sensor carriage 740 is movable while the liquid delivery device 900 is fixedly engaged with cap device 700).

In an example embodiment, cap device 700 includes a spring 760 configured to move sensor carriage 740 from a first position to a second position. For example, spring 760 may be manually compressed to move sensor carriage 740 to a first position proximate the front wall 712 of body 710, such as by insertion of liquid delivery device 900 into cavity 711, and may be biased to return sensor carriage to a second position proximate opening 714 of body 710 when released.

Sensor carriage 740 includes one or more sensor components configured to detect a condition of liquid delivery device 900 as the sensor carriage moves between a first position and a second position. In various example embodiments, sensor carriage 740 includes components of a plunger sensor configured to detect information that can be used to evaluate a condition of liquid delivery device 900. Alternatively, sensor carriage 740 may include only components of a position sensor (e.g. and not a plunger sensor).

In some embodiments, one or more optical sensors 744 may be fixedly positioned on body 710 of cap device 700.

Referring now to FIGS. 10A-10D, sensor carriage 740 includes one or more engagement features configured to interact with liquid delivery device 900. For example, sensor carriage 740 includes arms 746 that can be pushed by liquid delivery device 900 to move sensor carriage 740. When liquid delivery device 900 is inserted into cavity 711, interference between arms 746 and liquid delivery device 900 causes sensor carriage 740 to move with liquid delivery device 900 towards front wall 712 of body 710. Arms 746 may subsequently be moved out of engagement with liquid delivery device 900 to release sensor carriage 740 to return towards opening 714 of cavity 711 while liquid delivery device 900 remains in a fixed position relative to cavity 711 of cap device 700. For example, arms 746 may be flexible arms that may be movable between an engaged and disengaged configurations by interaction with one or more other components of sensor carriage 740 and/or cap 700. In some embodiments, spring 760 may be compressed when liquid delivery device 900 is fully inserted into cavity 711 (e.g. bore 748), and spring 760 may return sensor carriage 740 towards opening 714 when arms 746 are released from engagement with liquid delivery device 900.

In an example embodiment, sensor carriage 740 includes two arms 746 spaced around a circumference of sensor carriage 740. Arms 746 are movably between an extended position in which arms 746 extend into a bore 748 defined by sensor carriage 740 (e.g. extending inwardly away from an interior wall of sensor carriage 740), and a retracted position. Arms 746 may be movable relative to one or more components of sensor carriage 740, such as a sensor carriage ring 749a including cam surfaces 749b. In a first relative position (FIGS. 10A-10B), arms 746 are maintained in a flexed or engaged configuration by cam surfaces 749b. The arms 746 extend into bore 748 and are positioned to interfere with a liquid delivery device inserted into cap device 700. In a second relative position (FIGS. 10C-10D), arms 746 are out of contact with cam surfaces 749b and are in an unflexed or disengaged configuration (e.g. arms 746 are not forced into the engaged position by cam surfaces 749b). Arms 746 are positioned such that sensor carriage 740 can move relative to bore 748 and/or liquid delivery device 900 positioned within bore 748 without interference that prevents movement.

Relative movement between arms 746 and cam surface 749b may occur due to interaction between sensor carriage 740 and one or more features of cap device 700. For example, body 710 may include one or more ribs 718 that prevent further longitudinal movement of sensor carriage ring 749a during insertion of liquid delivery device 900. Continued movement of arms 746 may move arms 746 out of contact with cam surface 749b such that the arms can flex to a retracted or disengaged configuration (FIGS. 10C-10D). When the sensor carriage 740 is returned to a position proximate opening 714 (e.g. by spring 760), ribs 719 may prevent further longitudinal movement of sensor carriage ring 749a while spring 760 continues to push arms 746. Arms 746 may thus be forced into contact with cam surface 749b and moved to the extended or engaged configuration.

Figure 11A:
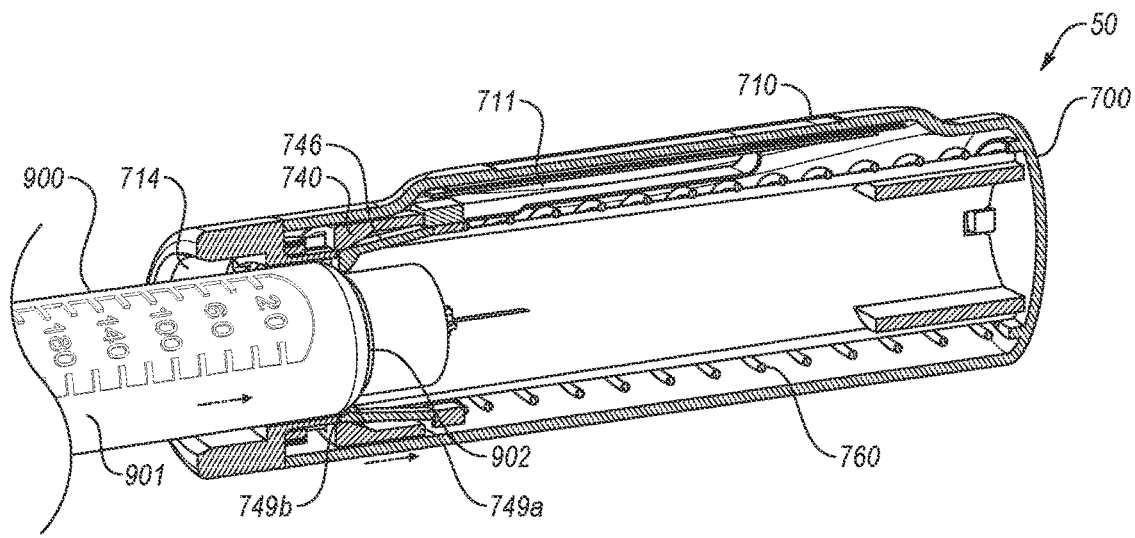
FIGS. 11A-11F show an example sensor carriage in multiple positions within a cap device.
Figure 11B:
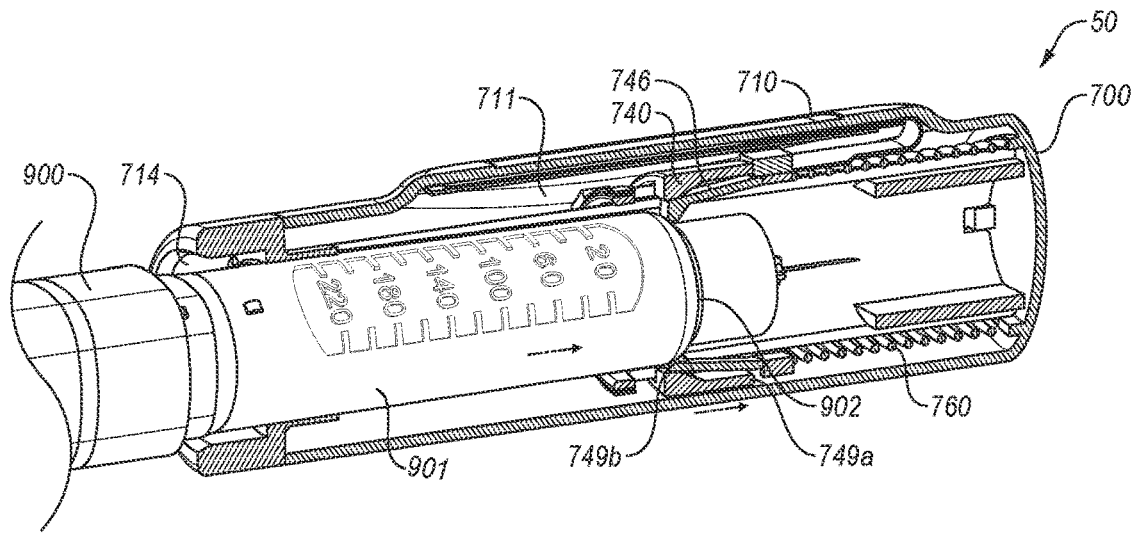
Figure 11C:
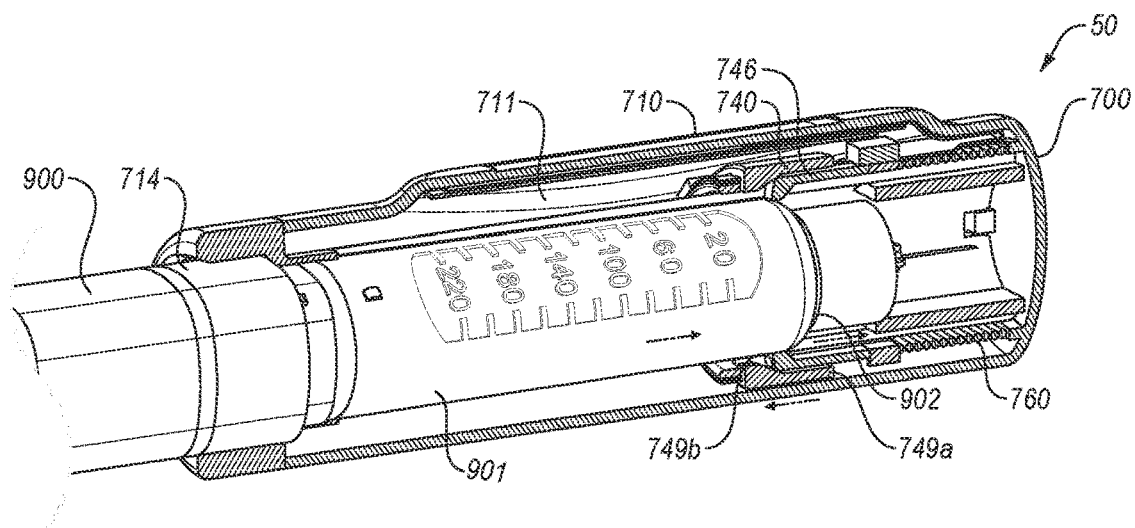
Figure 11D:
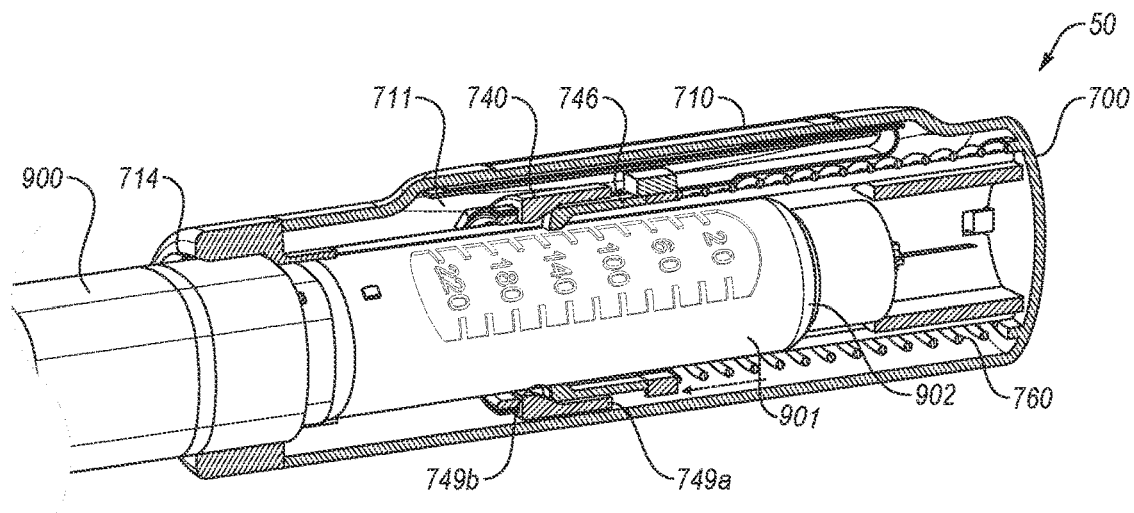
Figure 11E:
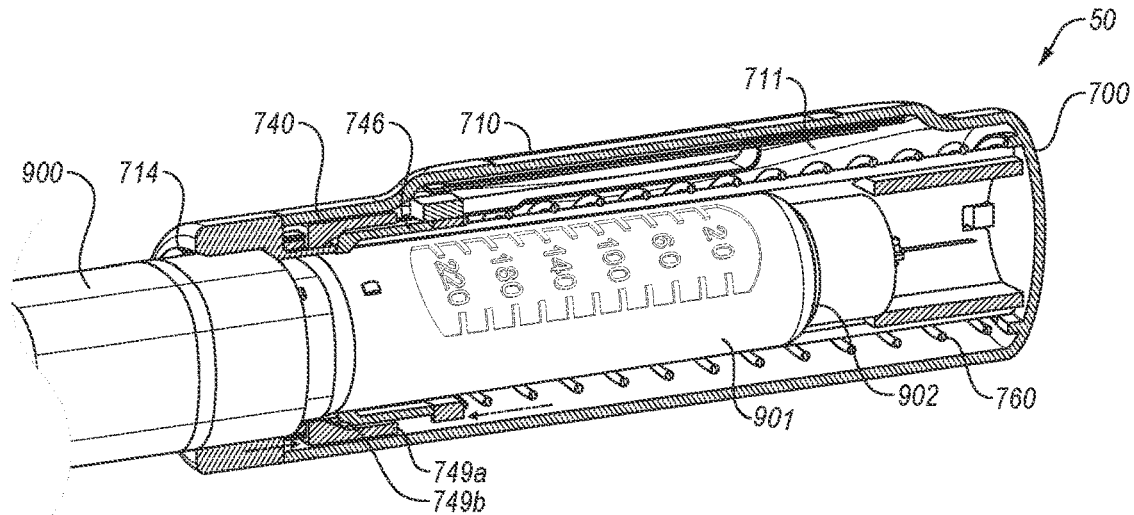
Figure 11F:
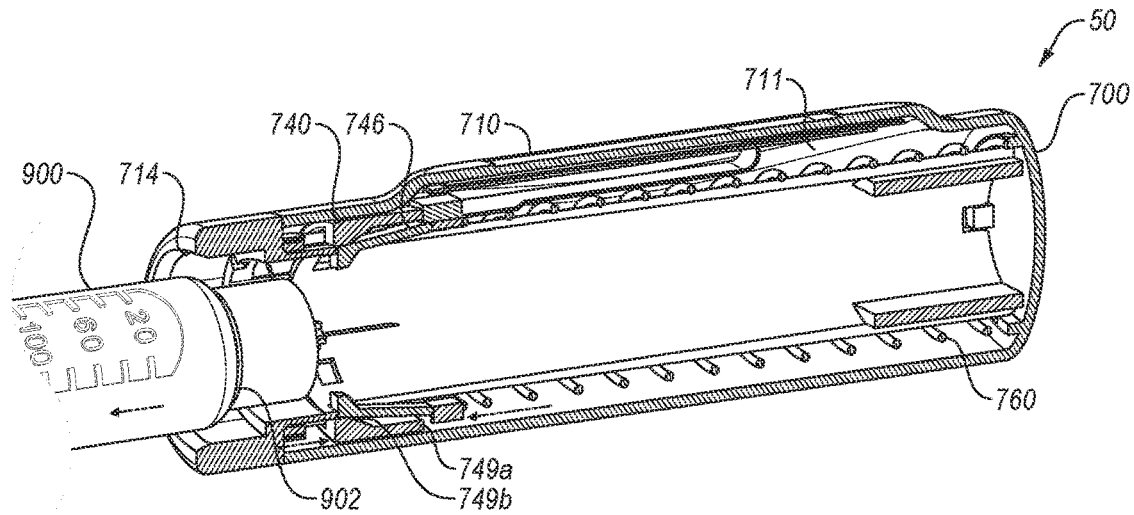

Referring to FIGS. 11A-F, cap device 700 is engageable with liquid delivery device 900 by insertion of delivery end 902 through opening 714 of body 710 and into cavity 711. As liquid delivery device 900 is inserted through opening 714 (FIG. 11A), delivery end 902 encounters engagement features of sensor carriage 740, such as arms 746 in an extended position. Relative movement between cap device 700 and liquid delivery device 900 (e.g. as cap device 700 and liquid delivery device 900 are brought together) results in liquid delivery device 900 pushing sensor carriage 740 into cavity 711 (FIG. 11B). When sensor carriage 740 reaches a position proximate front wall 712 of body 710, for example, longitudinal movement of sensor carriage ring 749a is stopped by ribs 718 while arms 746 may move relative to sensor carriage ring 749a (e.g. by force from insertion of liquid delivery device 900). Such relative movement results in arms 746 moving out of contact with cam surface 749b and into a disengaged configuration (FIG. 11C). Movement of arms 746 to the disengaged configuration moves arms 746, and sensor carriage 740, out of interference with liquid delivery device 900 such that the sensor carriage may be moved by spring 760 (e.g. towards opening 714) (FIG. 11D). When sensor carriage 740 reaches a position proximate opening 714 of body 710, for example, movement of sensor carriage ring 749a is stopped by ribs 719 while arms 746 may move relative to sensor carriage ring 749a (e.g. by force from spring 760) (FIG. 11E). Such relative movement results in arms 746 moving into contact with cam surface 749b and into a flexed or engaged configuration (FIG. 11F). With the sensor carriage 740 located proximate opening 714, and arms 746 in the engaged configuration, liquid delivery device 900 may again be received and the process repeated, for example.

Figure 12:
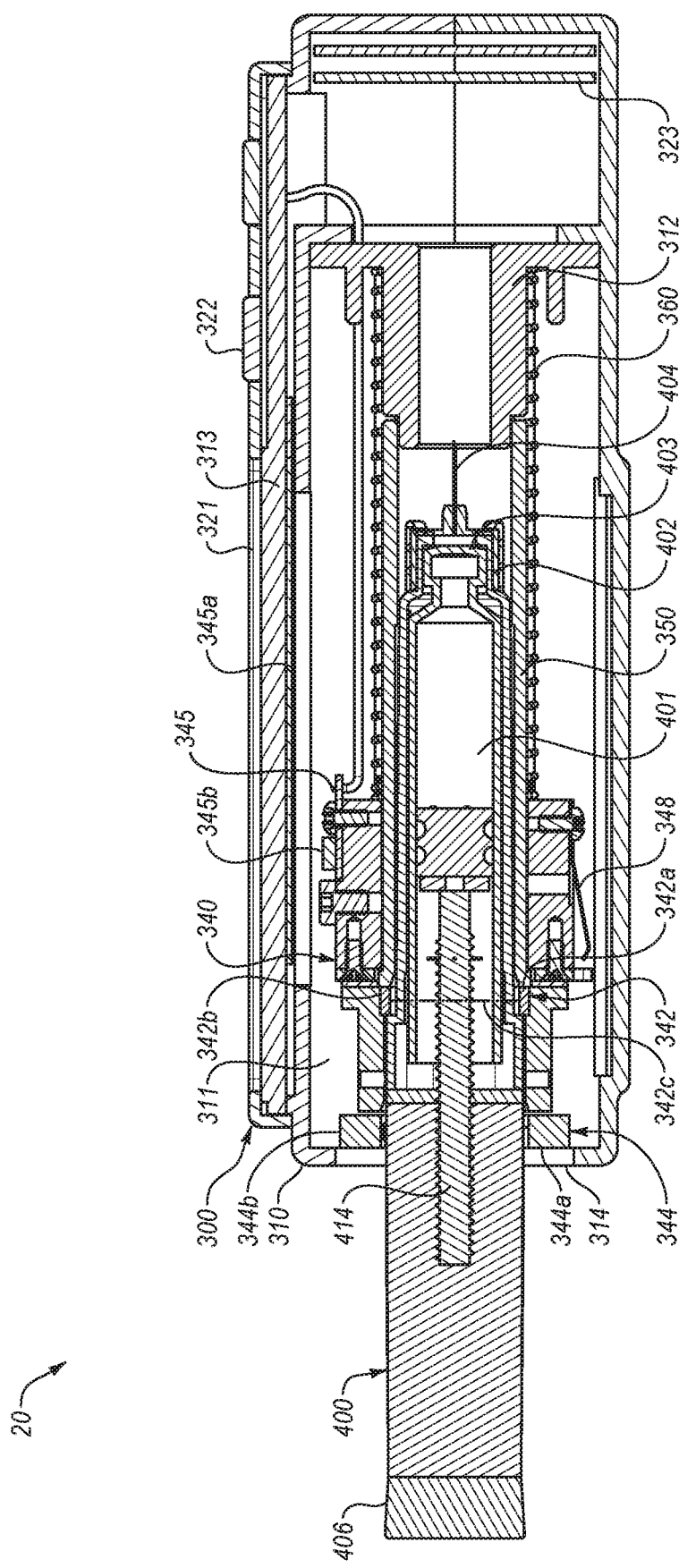
FIG. 12 is a cross-sectional view of an example liquid delivery device including a linear encoder.

Referring now to FIG. 12, an example liquid delivery system 20 is shown that can be used to store and deliver a liquid. Liquid delivery system 20 includes cap device 300 and liquid delivery device 400. Liquid delivery device 400 includes a reservoir 401, delivery end 402, and a plunger 405 that can be operated to deliver a dose of the liquid within reservoir 401 through delivery end 402. Cap device 300 is positionable over delivery end 402 of liquid delivery device 400 for storage of liquid delivery device 400 between uses. In an example embodiment, cap device 300 includes one or more sensors, including a linear encoder. The cap device is configured to detect a condition of liquid delivery device 400, such as a position of its plunger, and one or more output devices, such as a display, communication system, etc., configured to output information related to the condition of liquid delivery device 400. In some example embodiments, liquid delivery system 20 includes features and characteristics similar to features and characteristics of liquid delivery system 10 described above with reference to FIGS. 1 through 11.

Liquid delivery device 400 may be configured to deliver a measured dose of a liquid to a subject for the treatment of a medical condition. For example, liquid delivery device 400 may be a pen injector for delivering a liquid, such as insulin, to manage diabetes. In an example embodiment, delivery end 402 of liquid delivery device 400 includes a septum 403 and an injection needle 404. A desired dosage may be measured by operation of dial 406 (e.g. by manually rotating dial 406), and operating liquid delivery device 400 to advance the plunger. Advancement of plunger 405 via rod 414 pushes the measured dosage of liquid from reservoir 401, through delivery end 402, and into the subject. In an example embodiment, advancement of plunger 405 a particular distance results in a corresponding volume of liquid dispensed from liquid delivery device 400.

Cap device 300 may include one or more sensors configured to detect a condition of liquid delivery device 400. In an example embodiment, cap device 300 includes sensors that output sensor signals that may be evaluated to detect a plunger, a position of the plunger, a change in position of the plunger between successive engagements with cap device 300 (e.g. a change in position after delivery of a dose), and/or other conditions of liquid delivery device 400. The position of the plunger, and/or a change in the position of the plunger, may be used to monitor a volume of a dose delivered by liquid delivery device 400, a remaining total volume of liquid within reservoir 402, a remaining number of doses within reservoir 402, a remaining duration until reservoir 402 is emptied, and/or other information related to liquid delivery device 400.

Cap device 300 optionally includes user inputs 322 that facilitate user interaction with cap device 100. In an example embodiment, user inputs 322 include first and second buttons that may be operated to control cap device 300. For example, user inputs 322 may be operated by a user to activate cap device 300 and/or select information for display by display 321. Alternatively or additionally, user inputs 322 may be operated to reset settings and/or memory of cap device 300, such as when cap device 300 is engaged with a new liquid delivery device 400. In some example embodiments, cap device 300 does not include manually-operable user inputs. Cap device 300 that does not include buttons or other user inputs may improve ease of operability and promote the perception of a fully automated cap device 300.

Cap device 300 may communicate with one or more other components of a liquid delivery system to deliver and/or receive information related to a condition of cap device 100 and/or liquid delivery device 400. For example, cap device 300 includes a communication device 323 configured to communicate with one or more components remote from cap device 300. Communication device 323 may include a wireless communication printed circuit assembly configured for wireless communication, such as via short-wavelength UHF radio frequency, RF communication, WI-FI, BLUETOOTH, ZIGBEE, etc. Alternatively or additionally, communication device 323 may include an electrical port for wired communication with another electronic device. In various example embodiments, communication device 323 is configured for two-way communication, such as two-way communication with a mobile device having software configured to deliver and receive communications with cap device 300. Alternatively, cap device 300 may be configured for one-way communication, such as only to upload information to the mobile device, or only to receive information from the mobile device.

Communication device 323 may be configured to communicate with an electronic device configured with diabetes management software. For example, communication device 323 may transmit information related to liquid delivery device 400 that may be further processed by the electronic device. In this way, cap device 300 may facilitate remote review of information collected by its sensors by a remote user or healthcare provider, provide alerts related to liquid delivery system 400 by the electronic device (e.g. related to a scheduled time for an injection, a nearly empty liquid delivery device, etc.), and/or facilitate additional processing of the information collected by cap device 300.

In some embodiments, cap device 300 optionally includes a sensor carriage 340 that is movable within body 310 (e.g. movable within cavity 311). Sensor carriage 340 is configured to travel along at least a portion of liquid delivery device 400 within cavity 311, and cavity 311 is sized to accommodate the dimensions of liquid delivery device 400 and a path for sensor carriage 340. Sensor carriage 340 facilitates detection of characteristics of liquid delivery device 400 by carrying one or more sensors along liquid delivery device between a first position and a second position. Sensor carriage 340 is optionally movable between the first position and the second position relative to the cavity 311 while liquid delivery device 400 remains in a fixed position relative to the cavity 311 (e.g. the sensor carriage 340 is movable while the liquid delivery device 400 is fixedly engaged with cap device 300).

Cap device 300 may include a track 350. Sensor carriage 340 may travel along track 350, and track 350 may include one or more features that guide and/or limit the movement of sensor carriage 340. In an example embodiment, cap device 300 includes a spring 360 configured to move sensor carriage 340 from a first position to a second position. For example, spring 360 may be manually compressed to move sensor carriage 340 to a first position proximate the front wall 312 of body 310, such as by insertion of liquid delivery device 400 into cavity 311, and may be biased to return sensor carriage to a second position proximate opening 314 of body 310 when released.

Sensor carriage 340 includes one or more sensor components configured to detect a condition of liquid delivery device 400 as the sensor carriage moves between a first position and a second position. In various example embodiments, sensor carriage 340 includes components of a plunger sensor, such as an optical sensor, and a position sensor, such as linear encoder, configured to detect information that can be used to evaluate a condition of liquid delivery device 400. Alternatively, sensor carriage 340 may include only components of a position sensor (e.g. and not a plunger sensor). In some embodiments, one or more optical sensors 344 may be fixedly positioned on body 310 of cap device 300.

In some embodiments, sensor carriage 340 has a sensor 342 (e.g. a plunger sensor) that includes an emitter 342a and a receiver 342b, such as an optical emitter 342a and optical emitter 342b. Optical emitter 342a emits radiation that can be detected by optical receiver 342b, and in some embodiments may include an LED or laser diode. Optical receiver 342b may output a signal related to the amount of radiation received from optical emitter 342a, which may be dependent on the portion of liquid delivery device 400 present in path 342c between optical emitter 342a and optical received 342b. The amount of radiation received by optical receiver may thus be relatively lower when path 342c intersects plunger or other solid structure, and may be relatively higher when path 342c intersects transparent walls of a reservoir and its liquid contents.

Alternatively or additionally to sensor 342, sensor carriage 340 may include a position sensor 345 configured to output a sensor signal indicative of a position or distance. In an example embodiment, cap device 300 includes a position sensor 345 that outputs a sensor signal indicative of a position of sensor carriage 340 and/or distance sensor carriage 340 traveled between a first position and a second position (e.g. as sensor carriage 340 moves along liquid delivery device 400 or between subsequent doses of liquid delivery device 400). In an example embodiment, position sensor 345 includes a linear encoder, such as a reflective linear encoder or a transmissive linear encoder. An encoder codestrip 345a is located at least partially along a length of cavity 311, such as side wall 313 of body 310 or track 350. An encoder 345b, such as an optical encoder, is located on sensor carriage 340. In some example embodiments, encoder 345b may be positioned in close proximity to codestrip 345a but out of contact with codestrip 345a.

Linear encoder 345 may output a sensor signal (e.g. a count) that varies depending on the position of encoder 345b along codestrip 345a (e.g. and a position of sensor carriage 340 along cavity 311). In various example embodiments, codestrip 345a includes an optical pattern, such as a series of alternating dark and white lines. The linear encoder 345 may output a sensor signal indicative of a position of encoder 345b along codestrip 345a. For example, a particular count may be associated with a particular location along codestrip 345a, and the count may be consistent and repeatable each time encoder 345b travels along codestrip 345a.

The resolution of the encoder may be enhanced to a resolution finer than the thickness of the alternating lines of codestrip 345a by detecting a transition at the leading edge of each line and/or velocity-based interpolation techniques. In various example embodiments, linear encoder 345 may provide a highly accurate and reliable measurement having a resolution of less than 25 µm, less than 15 µm, less than 10 µm, between about 5 µm and 10 µm, or about 7.5 µm. The resolution of liquid delivery device 400 may be about 130 µm. The resolution of sensor 345 of cap device 300 may thus be between about 10 to 20 times the resolution of liquid delivery device 400. Such resolutions of sensor 345 facilitates a highly accurate determination of a position of plunger 405 with a significantly smaller error than the variation in dose delivery by liquid delivery device 400. In various example embodiments, high resolution may be achieved with little or no calibration of sensor 345 during assembly of cap device 300.

In an example embodiment, cap device 300 includes a processor configured to evaluate sensor signals from sensors 342 and/or 344, such as a variation in sensor signals indicative of the plunger, and to determine a corresponding position based on the sensor signal from sensor 345. In some embodiments, the corresponding position may be stored and compared to a corresponding position of the plunger during a subsequent measurement. A change in position may be evaluated to determine the volume of the previously delivered dose (e.g. by evaluating the distance traveled by the plunger). In some example embodiments, only a change in position of the plunger is evaluated, and the position of the plunger relative to other components of liquid delivery device 400 and/or cap device 300 is not evaluated.

Alternatively or additionally, the position of the plunger relative to a feature of liquid delivery device 400 and/or cap device 300 may be evaluated. For example, the processor may be configured to detect an output signal from one or more sensors 342 and/or 344 indicative of a leading end of reservoir 403, and to determine a corresponding position based on the output signal from sensor 345. The relative positions of such features may be evaluated to determine a distance between the leading end of reservoir 403 and plunger 405, which in turn facilitate calculation of a remaining total volume of liquid within reservoir 401, a remaining number of doses within reservoir 401, a remaining duration until reservoir 401 is emptied, and/or other information related to liquid delivery device 400.

Encoder 345b is out of contact during operation of sensor 345 such that encoder 345b is separated from codestrip 345a by a space. Encoder 345b thus does not create frictional resistance by contact with codestrip 345a, and frictional wear does not occur. Encoder 345b can repeatedly travel along codestrip 345a without wearing or otherwise affecting codestrip 345a. in some example embodiments, an optional spring 348 may be included to provide controlled drag against the motion of sensor carriage 340 propelled by spring 360. Controlled movement of sensor carriage 340 may be facilitated without causing frictional engagement or wear on components of sensors 342, 344, or 345, for example.

Alternatively or in addition to sensor 342, a sensor 344 fixedly positioned on body 310 of cap device 300 may be used to detect the plunger and/or other features of liquid delivery device 400. Sensors 344 may output sensor signals as liquid delivery device 400 is inserted into cavity 311 and brought into engagement with cap device 300. Spring 360 may promote controlled manual insertion of liquid delivery device 400 into cavity 311 (e.g. within a bore that receives liquid delivery device 400) of cap device 300.

Figure 13:
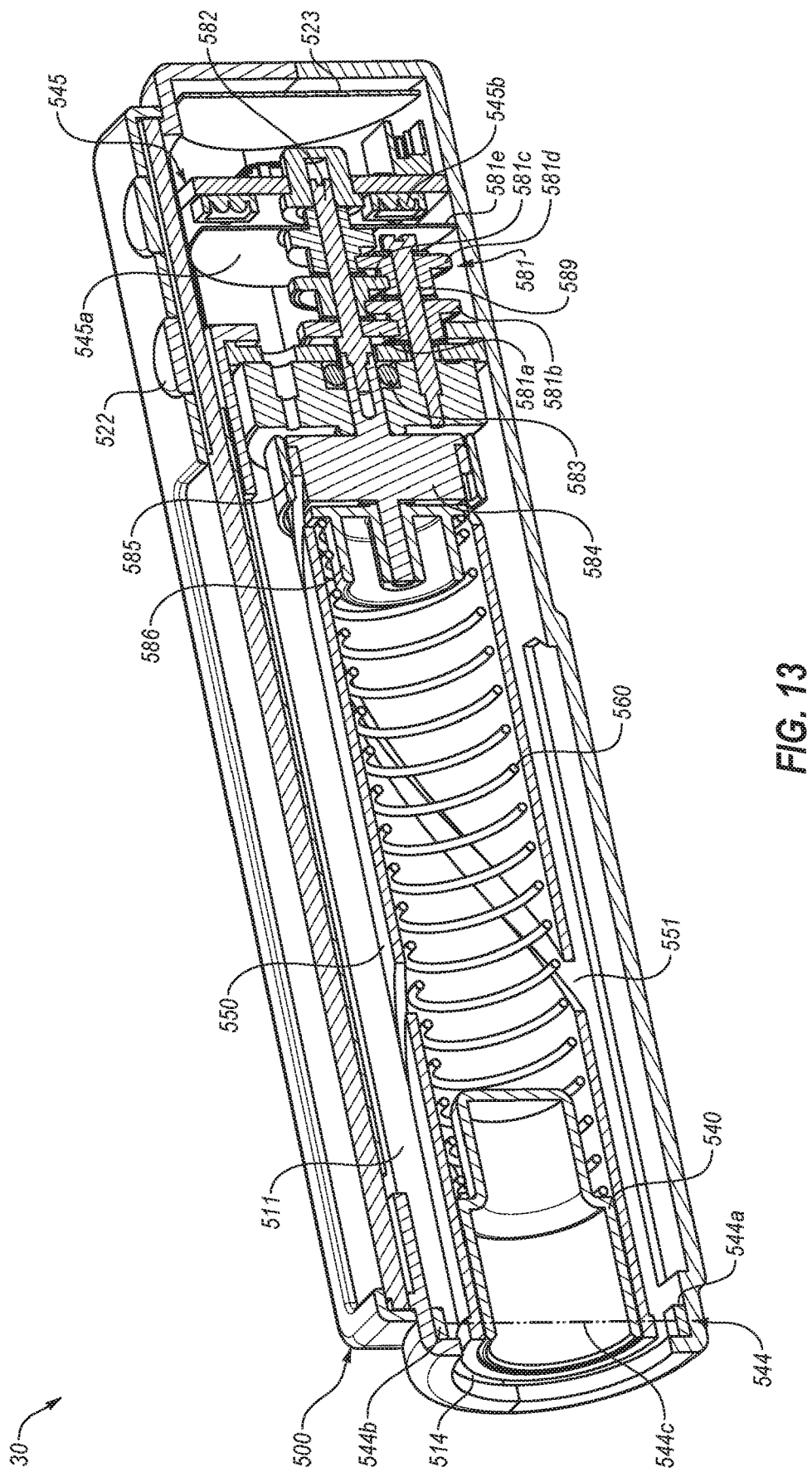
FIG. 13 is a cross-sectional view of an example liquid delivery device including a rotary encoder.

Referring now to FIG. 13, an example liquid delivery system 30 is shown that includes a rotary encoder position sensor. Liquid delivery system 30 includes cap device 500 that is positionable over a delivery end of a liquid delivery device for storage of the liquid delivery device between uses. In an example embodiment, cap device 500 includes one or more sensors configured to detect a condition of the liquid delivery device, such as a position of its plunger, and one or more output devices, such as a display, communication system, etc., configured to output information related to the condition of the liquid delivery device. In some example embodiments, liquid delivery system 30 includes features similar to features of liquid delivery systems 10 and 20 described above with reference to FIGS. 1 through 12.

Cap device 500 may include one or more sensors configured to detect a condition of the liquid delivery device. In an example embodiment, cap device 500 includes sensors that output sensor signals that may be evaluated to detect a plunger, a position of the plunger, a change in position of the plunger between successive engagements with cap device 500 (e.g. a change in position after delivery of a dose), and/or other conditions of the liquid delivery device. The position of the plunger, and/or a change in the position of the plunger, may be used to monitor a volume of a dose delivered by the liquid delivery device, a remaining total volume of liquid, a remaining number of doses, a remaining duration until the liquid delivery device is emptied, and/or other information related to the liquid delivery device.

Cap device 500 optionally includes user inputs 522 that facilitate user interaction with cap device 500. In an example embodiment, user inputs 522 include first and second buttons that may be operated to control cap device 500. For example, user inputs 522 may be operated by a user to activate cap device 500 and/or select information for display by display 521. Alternatively or additionally, user inputs 522 may be operated to reset settings and/or memory of cap device 500, such as when cap device 500 is engaged with a new liquid delivery device. In some example embodiments, cap device 500 does not include manually-operable user inputs. Cap device 500 that does not include buttons or other user inputs may improve ease of operability and promote the perception of a fully automated cap device 500.

Cap device 500 may communicate with one or more other components of a liquid delivery system to deliver and/or receive information related to a condition of cap device 500 and/or a liquid delivery device. For example, cap device 500 includes a communication device 523 configured to communicate with one or more components remote from cap device 500. Communication device 523 may include a wireless communication printed circuit assembly configured for wireless communication, such as via short-wavelength UHF radio frequency, RF communication, WI-FI, BLUETOOTH, ZIGBEE, etc. Alternatively or additionally, communication device 523 may include an electrical port for wired communication with another electronic device. In various example embodiments, communication device 523 is configured for two-way communication, such as two-way communication with a mobile device having software configured to deliver and receive communications with cap device 500. Alternatively, cap device 500 may be configured for one-way communication, such as only to upload information to the mobile device, or only to receive information from the mobile device.

Communication device 523 may be configured to communicate with an electronic device configured with diabetes management software. For example, communication device 523 may transmit information related to a liquid delivery device that may be further processed by the electronic device. In this way, cap device 500 may facilitate remote review of information collected by its sensors by a remote user or healthcare provider, provide alerts related to the liquid delivery system by the electronic device (e.g. related to a scheduled time for an injection, a nearly empty liquid delivery device, etc.), and/or facilitate additional processing of the information collected by cap device 500.

In some embodiments, cap device 500 optionally includes carriage 540 configured to receive at least a portion of a liquid delivery device. For example, carriage 540 may be configured to receive a delivery end of a liquid delivery device, and/or move together with the liquid delivery device as the liquid delivery device is engaged with cap device 500. Cap device includes a track 550 that carriage 540 is movable along (e.g. that guides and or limits carriage 540 as it travels within cavity 511).

In an example embodiment, cap device 500 includes a spring 560 configured to move carriage 540 from a first position to a second position. For example, spring 560 may be manually compressed when carriage 540 is moved towards front wall 512 of cavity 511, such as by insertion of a liquid delivery device 500 into cavity 511. Spring 560 may be biased to return carriage 540 to a second position proximate opening 514 of body 510 when released (e.g. when the liquid delivery device is removed from engagement with cap device 500). In an example embodiment, spring 560 is seated around spring hat 586.

Cap device 500 includes one or more sensor components configured to detect a condition of the liquid delivery device as the liquid delivery device is brought into engagement with cap device 500. In an example embodiment, cap device 500 includes a plunger sensor and/or a rotary encoder, configured to detect information that can be used to evaluate a condition of a liquid delivery device. For example, cap device 500 includes one or more sensors 544 fixedly positioned proximate opening 514 of cavity 511. Sensors 544 may include an emitter 542a and a receiver 542b, such as an optical emitter 542a and optical emitter 542b. Optical emitter 542a emits radiation that can be detected by optical receiver 542b, and in some embodiments may include an LED or laser diode. Optical receiver 542b may output a signal related to the amount of radiation received from optical emitter 542a, which may be dependent on the portion of the liquid delivery device present in path 542c between optical emitter 542a and optical receiver 542b. The amount of radiation received by optical receiver may thus be relatively lower when a plunger or other solid structure is present in path 542c, and may be relatively higher when transparent walls of a reservoir and its liquid contents are present in path 542c.

Alternatively or additionally to sensor 544, cap device 500 may include components of a position sensor configured to output a sensor signal indicative of a position or distance. In an example embodiment, cap device 500 includes a rotary encoder 570 that outputs a sensor signal indicative of a position of carriage 540 and/or distance carriage 540 traveled between a first position and a second position (e.g. as carriage 540 is pushed along cavity 511 during engagement of cap device 500 with a liquid delivery device).

Cap device 500 includes a track 550 having a helical slot 551. An end of track 550 is retained between track ring 585 and helical track base 584 such that track 550 is rotatable relative to carriage 540, body 510, and/or other components of cap device 500. Movement of carriage 540 along cavity 511 causes rotation of track 550 (e.g. rotation relative to carriage 540, body 510, and/or other components of cap device 500.

In an example embodiment, position sensor 545 includes an encoder codewheel 545a, and an encoder 545b, such as an optical encoder. Encoder 545b may be located in close proximity to codewheel 545a, but out of contact with codewheel 545a. The rotation of track 550 is translated to codewheel 545a and/or encoder 545b. The corresponding rotation is detected by encoder 545b. The rotary encoder 545 may generate a sensor signal (e.g. a count) that varies depending on the relative rotation of codewheel 545a and encoder 545b. In an example embodiment, codewheel 545a includes an optical pattern, such as a series of alternating dark and white lines. The rotary encoder 545 may output a sensor signal indicative of the rotation detected by encoder 545b. For example, a particular count may be associated with a particular rotation of codewheel 545a, and thus a particular rotation of track 550, and the count may be consistent and repeatable each time carriage 540 travels along track 550.

The resolution of the encoder can be enhanced to a finer resolution than the thickness of the alternating lines of codewheel 545a by detecting a transition at the leading edge of each line and/or velocity-based interpolation. In various example embodiments, linear encoder 345 may provide a highly accurate and reliable measurement having a resolution of less than 25 µm, less than 15 µm, less than 10 µm, between about 5 µm and 10 µm, or about 7.5 µm.

The resolution of rotary encoder 345 may be further enhanced by a gear train 581 between track 550 and codewheel 345a. For example, gear train may include gears 581a, 581b, 581c, 581d, 581e, that provide a gear ratio between 2 and 100, 4 and 50, 8 and 25, or of about 16. Gears 581a, 581c, 581e, may be rotatable on main shaft 582 supported by a bearing 583, for example, and gears 581b, 581d, rotatable on gear post 589. Accordingly, in some embodiments, each rotation of track 150 may produce multiple rotations of codewheel 545a.

In some embodiments, encoder 545b may be out of contact with codewheel 545a during operation of rotary encoder 545 such that encoder 545b is separated from codewheel 545a by a space. Encoder 545b thus does not create frictional resistance by contact with codewheel 545a, and frictional wear of codewheel 545a due to contact by encoder 545b does not occur. Encoder 345b can repeatedly detect codewheel 345a without wearing or otherwise affecting codewheel 345a.

Figure 14:
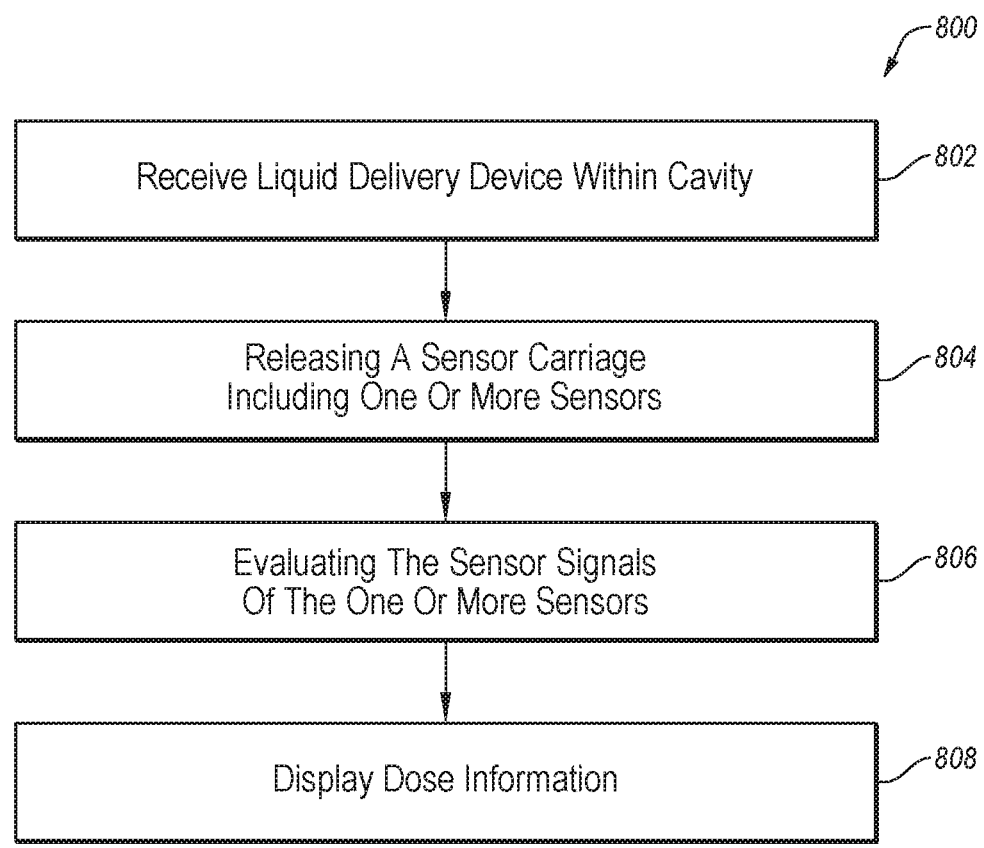
FIG. 14 is a flow diagram of an example method of evaluating the condition of a liquid delivery device.

Various example cap devices described herein facilitate effective, repeatable techniques of evaluating a condition of a liquid delivery device. Referring to FIG. 14, a flow diagram of an example method 800 of evaluating the condition of a liquid device is shown. Method 800 includes operation 802 of receiving at least a portion of a liquid delivery device within a cavity of a cap device. In various example embodiments, the liquid delivery device may have features and characteristics similar to liquid delivery devices 200, 400, 600, described herein, and may be a pen-injector device for administering a dose of insulin.

Operation 802 may include aligning the liquid delivery device with the cavity of the cap device, such as aligning a central longitudinal axis of the liquid delivery device with a central longitudinal axis of the cavity of the cap device. Alternatively or additionally, operation 802 may include aligning the liquid delivery device into one or more discrete alignment positions with the cap device. For example, liquid delivery device and/or cap device may have an asymmetrical feature and/or non-circular shape that facilitates receiving the liquid delivery device in one or more discrete positions selected based on locations of one or more sensors within the cap device. Operation 802 including aligning the liquid delivery device with the cap device in a particular orientation facilitates desired interaction between one or more sensors of the cap device and the liquid delivery device by reducing interference or obstruction by ribs, indicia, opaque regions, and/or other features.

In an example embodiment, operation 802 of receiving the liquid delivery device with the cavity of the cap device may include fixedly engaging the cap device with the liquid delivery device. For example, after operation 802, relative motion between the liquid delivery device and the cap device may be limited such that the liquid delivery device is not rotatable within the cavity and/or the liquid delivery device is not movable longitudinally within the cavity.

Method 800 may include operation 804 of releasing a sensor carriage including one or more sensors. When the sensor carriage is released, the sensor carriage may move from a first position to the second position while the liquid delivery device remains in a fixed position within the cavity. For example, the sensor carriage may move from a first position proximate a front wall that partially defines the cavity to a second position proximate an opening of the cavity. One or more sensors located on the sensor carriage operate while the sensor carriage moves between the first and second positions to output sensor signals indicative of one or more features of the liquid delivery device.

In some example embodiments, operation 804 of releasing the sensor carriage may be initiated without additional manual operation. For example, when the liquid delivery device is engaged with the cap device, the sensor carriage may be released without manual operation. One or more engagement features of the sensor carriage that interact with liquid delivery device may be moved or released such that the sensor carriage and liquid delivery device are not restricted to a fixed position relative to one another.

Method 800 may further include operation 806 of evaluating an output of the one or more sensors indicative of the presence of a feature of the liquid delivery device. For example, the cap device may include a processor configured to evaluate sensor signals from one or more of the sensors, such as a variation in sensor signals indicative of the plunger, and to determine a corresponding position. In some embodiments, operation 806 may include storing the corresponding position and comparing the corresponding position during subsequent capping events. Evaluating the sensor signals may including evaluating a change in position to determine the volume of the previous dose delivery (e.g. by evaluating the distance traveled by plunger 205), a remaining volume within the liquid delivery device, or other characteristics of the liquid delivery device.

In some embodiments, method 800 may include operation 808 of displaying an output related to the position of the plunger. For example, operation 808 may include displaying the previously delivered dose. Alternatively or additionally, operation 808 may include displaying dose information related to a remaining total volume of liquid within the reservoir of the liquid delivery device, a remaining number of doses within the reservoir of the liquid delivery device, a remaining duration until the reservoir of the liquid delivery device is emptied, a time of the previous dose (e.g. a time of operation 802 of receiving the liquid delivery device within the cavity), an elapsed time since the last dose (e.g. an elapsed time since operation 802 of receiving the liquid delivery device within the cavity), and/or other information related to the liquid delivery device.

Figure 15:
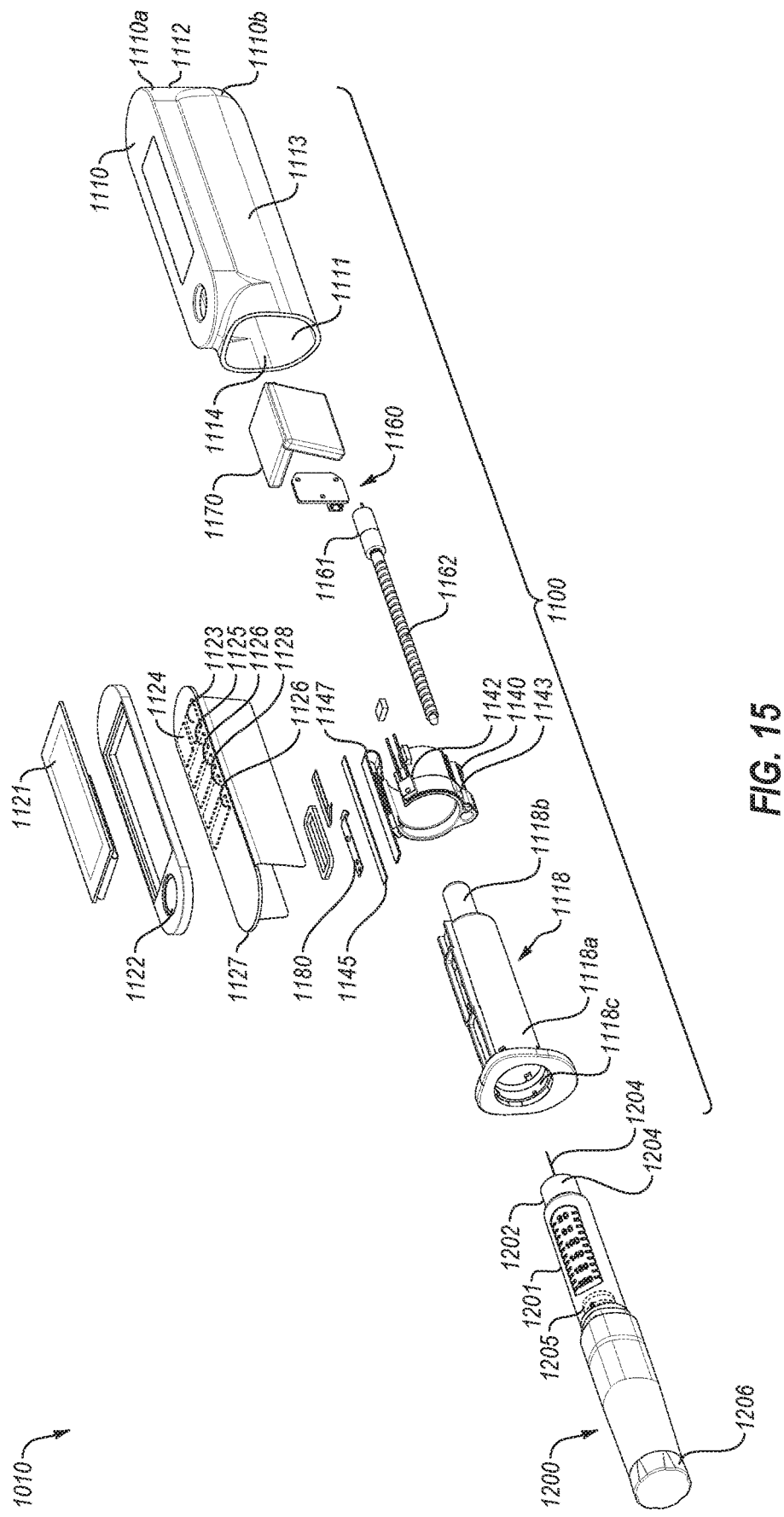
FIG. 15 is an exploded perspective view of an example liquid delivery system including a motorized cap device.
Figure 16:
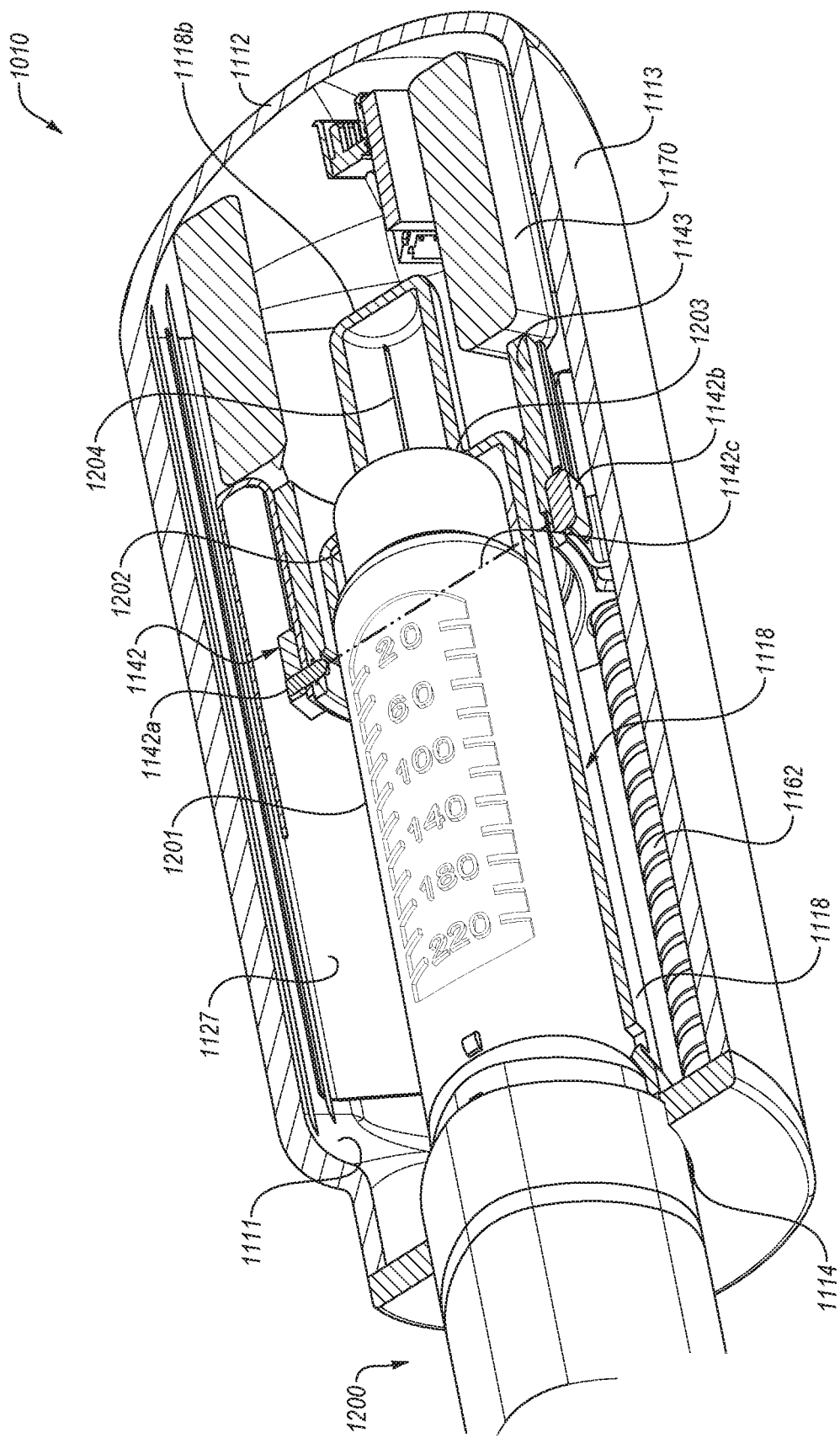
FIG. 16 is a partial cross-sectional view of the example liquid delivery system of FIG. 15.

Referring to FIGS. 15-17, an example liquid delivery system 1010 that includes a motorized cap device 1100 and liquid delivery device 1200 is shown. Liquid delivery system 1010 can be used to store and deliver a liquid, and output dosage information to a user, and in some example embodiments, liquid delivery system 1010 includes one or more features similar to features of liquid delivery systems 10, 20, and 30 described above with reference to FIGS. 1 through 14.

Liquid delivery device 1200 includes a reservoir 1201, delivery end 1202, and a plunger 1205 that can be operated to deliver a dose of the liquid within reservoir 1201 through delivery end 1202. Cap device 1100 is positionable over delivery end 1202 of liquid delivery device 1200 for storage of liquid delivery device 1200 between uses. In an example embodiment, cap device 1100 includes one or more sensors configured to detect a condition of liquid delivery device 1200, such as a position of its plunger, and one or more output devices, such as a display, communication system, etc., configured to output information related to the condition of liquid delivery device 1200.

Liquid delivery device 1200 may be configured to deliver a measured dose of a liquid to a subject for the treatment of a medical condition. For example, liquid delivery device 1200 may be a pen injector for delivering a liquid, such as insulin, to manage diabetes. In an example embodiment, delivery end 1202 of liquid delivery device 1200 includes a septum 1203 and an injection needle 1204. A desired dosage may be measured by operation of dial 1206 (e.g. by manually rotating dial 1206), and delivered by advancing plunger 1205. Advancement of plunger 1205 via rod 1214 pushes the measured dosage of liquid from reservoir 1201, through delivery end 1202, and into the subject. In an example embodiment, advancement of plunger 1205 a particular distance causes a corresponding volume of liquid to be dispensed from liquid delivery device 1200.

Cap device 1100 includes a body 1110 that defines a cavity 1111 configured to receive at least a portion of liquid delivery device 1200, such as at least a portion of delivery end 1202 and/or reservoir 1201. Cap device 1100 is positionable over delivery end 1202 and may retain liquid delivery device 1200 (e.g. between periods of use). Cap device 1100 may protect delivery end 1202 from damage or contaminants of the external environment, and contain injection needle 1204. Liquid delivery device 1200 may be removed from cavity 1111 of cap device 1100 before each use, and subsequently engaged with cap device 1100 after a dose has been delivered. Cap device 1100 may thus be removed from and replaced onto liquid delivery device 1200 over multiple uses. After the contents of a particular liquid delivery device 1200 has been exhausted, the liquid delivery device 1200 may be discarded, and cap device 1100 used with a new liquid delivery device. In some example embodiments, liquid delivery device 1200 is disposable when its usable contents are exhausted, and cap device 1100 may be reusable with multiple liquid delivery devices 1200. In other example embodiments, cap device 1100 may be associated with a particular liquid delivery device 1200, and both the cap device 1100 and the liquid delivery device 1200 may be disposed when the contents of reservoir 1201 are exhausted.

Cap device 1100 may include one or more sensors configured to detect a condition of liquid delivery device 1200. In an example embodiment, cap device 1100 includes sensors that output sensor signals that may be evaluated to detect plunger 1205, a position of plunger 1205, a change in position of plunger 1205 between successive engagements with cap device 1100 (e.g. a change in position after delivery of a dose), and/or other conditions of liquid delivery device 1200. The position of plunger 1205, and/or the change in the position of plunger 1205, may be used to monitor a volume of a dose delivered by liquid delivery device 1200, a remaining total volume of liquid within reservoir 1201, a remaining number of doses within reservoir 1201, a remaining duration until reservoir 1201 is emptied, and/or other information related to liquid delivery device 1200.

Cap device 1100 may include various components that facilitate calculation, display, storage, and/or communication of sensor signals that may be output by the one or more sensors. In an example embodiment, cap device 1100 includes a display 1121, user inputs 1122, communication device 1123, memory 1124, processor 1125, speaker 1126, and circuit board 1127. One or more components may be in electrical communication with one or more other components via circuit board 1127, and processor 1125 may be configured with logic to control operation of one or more of display 1121, user inputs 1122, communication device 1123, memory 1124, and speaker 1126, and to process sensor signals received from one or more sensors of cap device 1100.

Display 1121 provides a visual output to a user related to a condition of cap device 1100 and/or liquid delivery device 1200. Display 1121 may be an LED, LCD, electronic ink, or e-paper display, for example. In some embodiments, display 1121 may provide a visual indication related to a volume of a dose delivered by liquid delivery device 1200, a remaining total volume of liquid within reservoir 1201, a remaining number of doses within reservoir 1201, a remaining duration until reservoir 1201 is emptied, a time of the previous dose (e.g. a time the cap device 1100 was replaced on liquid delivery device 1200), an elapsed time since the last dose (e.g. an elapsed time since cap device 1100 was replaced on liquid delivery device 1200), and/or other information related to liquid delivery device 1200.

Alternatively or additionally, cap device 1100 may include audio and/or vibratory alerts related to a condition of cap device 1100 and/or liquid delivery device 1200. Processor 1125 may control audio output of speaker 1126 to output an audible alert, or vibrator 1128 to output a vibratory alert, which may be perceived as an indication of a volume of a dose delivered by liquid delivery device 1200, a remaining total volume of liquid within reservoir 1201, a remaining number of doses within reservoir 1201, a remaining duration until reservoir 1201 is emptied, a time of the previous dose (e.g. a time the cap device 1100 was replaced onto liquid delivery device 1200), an elapsed time since the last dose (e.g. an elapsed time since cap device 1100 was replaced onto liquid delivery device 1200), and/or other information related to liquid delivery device 1200. Alternatively or additionally, vibrator 1128 may deliver vibrations to liquid delivery device 1200. Vibrator 1128 may be activated to facilitate mixing of the contents of liquid delivery device 1200 and/or to reduce the formation or buildup of precipitates (e.g. on the leading surface of plunger and/or surfaces of reservoir 1201).

Cap device 1100 optionally includes one or more user inputs 1122 that facilitate user interaction with cap device 1100. In an example embodiment, user inputs 1122 include first and second buttons that may be operated to control cap device 1100. For example, user inputs 1122 may be operated by a user to activate cap device 1100 and/or select information to be displayed by display 1121. Alternatively or additionally, user inputs 1122 may be operated to reset settings and/or memory 1124 of cap device 1100, such as when cap device 1100 is engaged with a new liquid delivery device 1200. In some example embodiments, cap device 1100 does not include user inputs 1122, such as buttons. Cap device 1100 that does not include buttons or other user inputs may promote the perception of a fully automated cap device 1100 and/or improve user operability.

Cap device 1100 may communicate with one or more other components of a liquid delivery system to deliver and/or receive information related to a condition of cap device 1100 and/or liquid delivery device 1200. For example, cap device 1100 includes a communication device 1123 configured to communicate with one or more components remote from cap device 1100. Communication device 1123 may include a wireless communication printed circuit assembly configured for wireless communication, such as via short-wavelength UHF radio frequency, RF communication, WI-FI, BLUETOOTH, ZIGBEE, etc. Alternatively or additionally, communication device 1123 may include an electrical port for wired communication with another electronic device. In various example embodiments, communication device 1123 is configured for two-way communication, such as two-way communication with a mobile device having software configured to deliver and receive communications with cap device 1100. Alternatively, cap device 1100 may be configured for one-way communication, such as only to upload information to the mobile device, or only to receive information from the mobile device.

Communication device 1123 may be configured to communicate with an electronic device configured with diabetes management software. For example, communication device 1123 may transmit information related to liquid delivery device 1200 that may be further processed by the electronic device. In this way, cap device 1100 may facilitate review of information collected by its sensors by a remote user or healthcare provider, provide alerts related to liquid delivery system 1010 by the electronic device (e.g. related to a scheduled time for an injection, a nearly empty liquid delivery device, etc.), and/or facilitate additional processing and analysis of the information collected by cap device 1100.

Cap device 1100 includes a power source 1170. In an example embodiment, power source 1170 comprises one or more batteries, such as alkaline batteries, nickel cadmium batteries, lithium ion batteries, lithium polymer batteries, etc. In one example embodiment, power source 1170 may include a rechargeable 3.7 V lithium polymer battery to power a motor of a motorized drive mechanism, communication device 1123, and/or one or more other components of cap device 1100. Such power sources 1170 may provide an extended period of time before recharging, such as longer than five days of normal use, longer than 7 days of normal use, or longer. Power source 1170 may be associated with a micro-switch configured to switch cap device between an inactive or low power state to an active or operational state in which sensors of cap device 1100 are active. Alternatively or additionally, a sensor signal from one or more sensors of cap device 1100, such as one or more position sensors, may provide an alert to processor 1125 to switch cap device to the active or operational state.

Still referring to FIGS. 15 and 16, body 1110 of cap device 1100 defines cavity 1111 configured to receive at least a portion of liquid delivery device 1200 (e.g. within a bore of cavity 1111). For example, body 1110 may include a front wall 1112, side walls 1113, and an opening 1114. Body 1110 may be configured to house various components of cap device 1100, such as display 1121, user inputs 1122, communication device 1123, memory 1124, processor 1125, speaker 1126, and circuit board 1127. In various example embodiments, body 1110 is a molded body, such as a molded plastic. Body 1110 may include multiple body portions that are assembled to form body 1110, such as a first body portion 1110*a* and a second body portion 1110*b* that may be joined to define cavity 1111 and/or other spaces to accommodate components of cap device 1100. A body 1110 that includes first and second body portions 1110*a*, 1110*b* may facilitate efficient manufacturing of body 1110 and/or efficient assembly with other components of cap device 1100. In other example embodiments, the portion of body 1110 that defines cavity 1111 may be integrally formed as a unitary component (e.g. such that multiple components do not need to be joined in order to define cavity 1111).

In an example embodiment, cap device 1100 includes a sleeve 1118 (e.g. body 1110 includes a sleeve 1118) configured to receive at least a portion of liquid delivery device 1200. Sleeve 1118 may includes side walls 1118*a* and a front wall 1118*b* configured to receive delivery end 1202 and/or injection needle 1204 of liquid delivery device 1200. The sleeve at least at least partially surrounds injection needle 1204 (e.g. proximate a front of cap device 1100) and reservoir 1201 between injection needle 1204 and opening 1114. Alternatively or additionally, sleeve 1118 may include one or more retention features that engage with liquid delivery device 1200 and limit relative movement between liquid delivery device 1200 and body 1110 of cap device 1100.

Motorized cap device 1100 includes sensor carriage 1140 that is movable within body 1110 (e.g. movable within cavity 1111 between walls 1113 and sleeve 118). Sensor carriage 1140 is configured to travel along at least a portion of liquid delivery device 200 within cavity 111, and cavity 1111 is sized to accommodate the dimensions of liquid delivery device 1200 and a path for sensor carriage 1140. Sensor carriage 1140 facilitates detection of characteristics of liquid delivery device 1200 by carrying one or more sensors along liquid delivery device. In an example embodiment, sensor carriage 1140 is movable between the first position and the second position relative to cavity 1111 while liquid delivery device 1200 remains in a fixed position relative to sleeve 1118/cavity 1111 (e.g. sensor carriage 1140 is movable while the liquid delivery device 1200 is fixedly engaged with cap device 1100).

Sensor carriage 1140 may travel along sleeve 1118, and sleeve 1118 may include one or more features that guide and/or limit the movement of sensor carriage 1140. In an example embodiment, sensor carriage 1140 defines an opening having a shape complementary to the shape of sleeve 1118 (e.g. sensor carriage 1140 defines a circular opening sized similarly to a circular cross-section of sleeve 1118). Alternatively or additionally, sleeve 1118 may include one or more ribs or other features that interact with a complementary feature of sensor carriage 1140 and that define a path that sensor carriage 1140 travels along (e.g. in a longitudinal direction between a first position relatively closer to front wall 1112 and a second position relatively closer to opening 1114. In some embodiments, sensor carriage 1140 is located entirely outside of sleeve 1118 (e.g. such that no part of sensor carriage 1140 extends into sleeve 1118). Sleeve 1118 may thus protect sensor carriage 1140 from the external environment and/or the contents of liquid delivery device 1200.

In some embodiments, sleeve 1118 includes one more features configured to interact with features of liquid delivery device 1200. For example, interior surfaces 1118*c* of sleeve 1118 may include features that orient and/or retain liquid delivery device 1200 within cap device 1100. Sleeve 1118 may at least partially surround reservoir 1201 of liquid delivery device 1200, and sensor carriage 1140 may be movable between sleeve 1118 and side walls 1113 that define cavity 1111 of cap device 1100. Thus, in an example embodiment, sleeve 1118 is positioned between liquid delivery device 1200 and sensor carriage 1140 during operation of sensor carriage 140. Sleeve 1118 may be at least partially constructed from an optically clear material, for example, or other material that allows operation of the sensors associated with sensor carriage 1140.

In some embodiments, sleeve 1118 may be integrally formed with body 1110 of cap device 1100. For example, sleeve 1118 may be integrally formed with body 1110 as a unitary component. Alternatively, sleeve 1118 may be formed as a component separate from other components of body 1110 and subsequently assembled with the other components of body 1110. For example, sleeve 1118 may be sealing joined to other components of body 1110 proximate opening 1114 and/or other locations of body 1110. A separately formed sleeve 1118 may facilitate manufacture of sleeve 1118 (e.g. which may optionally have tighter manufacturing tolerances and/or include features otherwise difficult to form within cavity 1111 of body 1110).

Sleeve 1118 may protect electronic and other components within body 1110 from liquid, debris, and environmental contaminants. In an example embodiment, sleeve 1118 is sealed with other components of body 1110 and/or does not define openings into cavity 1111. Cavity 1111 may thus define a hermetically sealed cavity. Sensor carriage 1140 driven by motorized drive system 1160 (e.g. exclusively driven by motorized drive system 1160) may facilitate a sleeve 1118 that does not include openings. Such a construction may provide a robust liquid delivery system 1010 in which mechanical and electronic components are protected.

Cap device 1100 includes a motorized drive system 1160 configured to drive sensor carriage 1140 along a longitudinal axis of cap device 100 (e.g. along a longitudinal axis extending centrally through front wall 112 and opening 114). For example, motorized drive system 1160 may include a motor 1161 and leadscrew 1162 connected, directly or indirectly, to a drive shaft of motor 1161. Rotation of the leadscrew 1162 caused be operation of motor 1161 results in movement of sensor carriage. Rotation of motor 1161 in a first direction results in movement of sensor carriage 1140 towards opening 1114 of cavity 1111 and rotation of motor 1161 in a second direction results in movement of sensor carriage 1140 towards front wall 1112 of body 1110. In an example embodiment, motorized drive system 1160 can thus drive sensor carriage 1140 between any number of discrete points along leadscrew 1162.

In various example embodiments, liquid delivery device 1200 remains in a fixed position relative to cavity 1111 and body 1110 of cap device 1100 while sensor carriage 1140 travels along liquid delivery device 1200. Liquid delivery device 1200 is constrained against twisting or rotation about longitudinal axis A of cavity 1111, and/or may be constrained from longitudinal movement along longitudinal axis A. Limited or no relative movement between liquid delivery device 1200 and body 1110 facilitates accurate and repeatable detection of plunger 1205 by sensors of sensor carriage 1140, and provides a predictable line of sight for the sensors of sensor carriage 1140.

In some example embodiments, sensor carriage 1140 includes one or more sensor components configured to detect a condition of liquid delivery device 1200 (e.g. similar to sensor carriage 140, in some embodiments). Sensor carriage 1140 may include components of a plunger detection sensor, such as a reflective optical sensor or a transmissive optical sensor, and/or a position sensor, such as a load sensor, linear potentiometer, linear encoder, rotary encoder, magnetic potentiometer, or membrane potentiometer, for example, configured to detect information that can be used to evaluate a condition of liquid delivery device 1200.

Sensor carriage 1140 includes one or more sensor components configured to detect a condition of liquid delivery device 1200, such as a position of a plunger within liquid delivery device 1200. For example, sensor carriage 1140 includes a sensor 1142 that outputs a sensor signal representative of a characteristic of liquid delivery device 1200. The output signal from sensor 1142 may vary depending on a physical characteristic of liquid delivery device 1200 encountered by sensor 1142, and thus the output signal may differ at different positions along a length of liquid delivery device 1200. For example, as sensor carriage 1140 moves relative to liquid delivery device 1200, a change in the output signal of sensor 1142 may be evaluated to determine a leading end of reservoir 1201 (e.g. at delivery end 1202), a leading end of plunger 1205, a trailing end of plunger 1205, and/or other attributes of liquid delivery device 1200. A change in position detected between a series of doses, such as a change in position of plunger 1205 before and after a dose has been delivered, may be used to evaluate a volume of a dose delivered by liquid delivery device 1200, a remaining total volume of liquid within reservoir 1201, a remaining number of doses within reservoir 1201, a remaining duration until reservoir 1201 is emptied, a time of the previous dose (e.g. a time the cap device 1100 was replaced on liquid delivery device 1200), an elapsed time since the last dose (e.g. an elapsed time since cap device 1100 was replaced on liquid delivery device 1200), and/or other information related to liquid delivery device 1200. Alternatively or additionally, the relative positions of one or more of these detected characteristics, or a distance between one or more of these detected characteristics, may be used to evaluate dosage information related to liquid delivery device 1200.

In an example embodiment, sensor 1142 includes an emitter 1142a and a receiver 1142b (FIG. 16), such as an optical emitter 1142a and optical receiver 1142b (e.g. and in some embodiments may have one or more features of sensors 142 described herein). Emitter 1142a and receiver 1142b may be arranged in alignment with one another such that an optical path 1142c between emitter 1142a and receiver 1142b extends perpendicular (e.g. substantially perpendicular, within 10° of exactly perpendicular) to the central longitudinal axis A of cavity 111. Path 1142c passes at least partially through sleeve 1118 between emitter 1142a and receiver 1142b. In some embodiments, emitter 1142a is configured to generate a narrow beam with limited spread outside of optical path 1142c, such as by an emitter 1142a that emits a narrow beam and/or by a collimating structure configured to focus the output of emitter 1142a along path 1142c. In various example embodiments, radiation emitted by emitter 1142a may be within visible and/or invisible wavelengths.

In some example embodiments, sensor 1142 may be a reflective sensor that detects reflected light. Reflective sensor 1142 may detect a color transition indicative of plunger 1205, such as transition from a relatively higher transparency and/or light color of liquid and/or reservoir 1201 to the relatively lower transparency and/or dark color of plunger 1205 (e.g. red, orange, black, etc.).

Sensor carriage 1140 may include multiple sensors, such as first and second optical sensors 1142, 1143, each including an emitter and a receiver, for example. In various example embodiment, the relative locations of first and second sensors may be selected to promote an appropriate line of sight (e.g. through liquid delivery device 1200) by at least one of the first and second sensors.

Alternatively or additionally to sensor 1142, sensor carriage 1140 may include a position sensor 1145 configured to output a sensor signal indicative of a position or distance. In an example embodiment, cap device 1100 includes a position sensor 1145 that outputs a sensor signal indicative of a position of the sensor carriage and/or distance the sensor carriage traveled between a first position and a second position (e.g. as sensor carriage 1140 moves along liquid delivery device 1200 or between subsequent doses of liquid delivery device 1200). In an example embodiment, position sensor 1145 includes a linear potentiometer. A resistive element is located at least partially along a length of cavity 1111, such as side wall 1113 of body 1110 or sleeve 1118. A wiper is located on sensor carriage 1140.

Sensor 1145 may output a sensor signal (e.g. a voltage) that varies depending on the position of the wiper along the resistive element (e.g. and a position of sensor carriage 1140 along cavity 1111). For example, a particular voltage may be associated with a particular location along the resistive element, and the voltage may be consistent and repeatable each time the wiper travels along the resistive element. Sensor 1145 may have a unique signature of voltage outputs for each location of the wiper, and can be calibrated to achieve highly precise and repeatable measurements.

Alternatively or additionally to a linear potentiometer, position sensor 1145 may include one or more other sensor types that provide an indication of position that can be correlated with an sensor signal output by sensor 1142. For example, position sensor 1145 may include a linear encoder, rotary encoder, magnetic potentiometer, membrane potentiometer, load cell, etc., for example.

In an example embodiment, processor 1125 is configured to evaluate sensor signals from sensors 1142 and/or 1143, such as a variation in sensor signals indicative of the plunger, and to determine a corresponding position based on the sensor signal from sensor 1145. In some embodiments, the corresponding position may be stored and compared to a corresponding position of plunger 1205 during a subsequent measurement. A change in position may then be evaluated to determine the volume of the previously delivered dose (e.g. by evaluating the distance traveled by plunger 1205). In some example embodiments, only a change in position of plunger 1205 is evaluated, and the position of plunger 1205 relative to other components of liquid delivery device 1200 and/or cap device 1100 is not evaluated.

Alternatively or additionally, the position of plunger 1205 relative to a feature of liquid delivery device 1200 and/or cap device may be evaluated. For example, processor may be configured to detect a sensor signal output from sensors 1142, 1143 indicative of a leading end of reservoir 1201, and to determine a corresponding position based on the output signal from sensor 1145. The relative positions of such features may be evaluated to determine a distance between the leading end of reservoir 1201 and plunger 1205, which in turn may facilitate calculation of a remaining total volume of liquid within reservoir 1201, a remaining number of doses within reservoir 1201, a remaining duration until reservoir 1201 is emptied, and/or other information related to liquid delivery device 1200.

Sensor carriage 1140 may be electrically connected with processor 1125 to facilitate electrical communication of sensor signals. In some embodiments, a flexible electrical connector 1147 provides electrical connection at least partially between sensor carriage 1140 and circuit board 1127 that supports processor 1125. Flexible electrical connector may include conductive electrical structures on a thin, flexible substrate. For example, the flexible electrical connector may include one or more layers of PEEK, polyester, or polyamide having printed or laminated electrical structures. The flexible electrical connector thus may have a thin profile that facilitates bending to a small radius of curvature. The flexible electrical connector may bend and flex during movement of the sensor carriage 1140, while maintaining electrical connection with circuit board 1127 and/or processor 1125.

In some embodiments, sensor carriage 1140 may be electrically connected with circuit board 1127 via one or more components of motorized drive system 1160, such as leadscrew 1162. Alternatively or additionally, sleeve 1118 may include one or more electrical conductors that provide electrical communication between sensor carriage 1140 and circuit board 1127 while sensor carriage 1140 travels along track 1150. For example, sensor carriage 1140 may have a fixed electrical contact biased towards sliding engagement with a complementary electrically conductive surface of sleeve 1118.

In some embodiments, sensor carriage 1140 is not in continuous electrical connection with circuit board 1127 and/or processor 1125. For example, sensor carriage 1140 may operate to detect a condition of liquid delivery device 1200 while not in electrical communication with circuit board 1127 and/or processor 1125. Sensor carriage 1140 may include a power source that can deliver power to one or more sensors carried by sensor carriage 1140, and a sensor carriage memory to store sensor signal information. The sensor carriage 1140 may store sensor information collected as it travels between the first and second positions, and may be brought into electrical communication with circuit board 1127 and/or processor 1125 when stopped at a particular position. For example, after each operation of sensor carriage 1140, or a series of operations, sensor carriage 1140 may be driven by motorized drive system 1160 to a position in which sensor carriage 1140 is in electrical communication with circuit board 1127 and/or processor 1125 such that the collected information may be communicated.

Figure 17A:
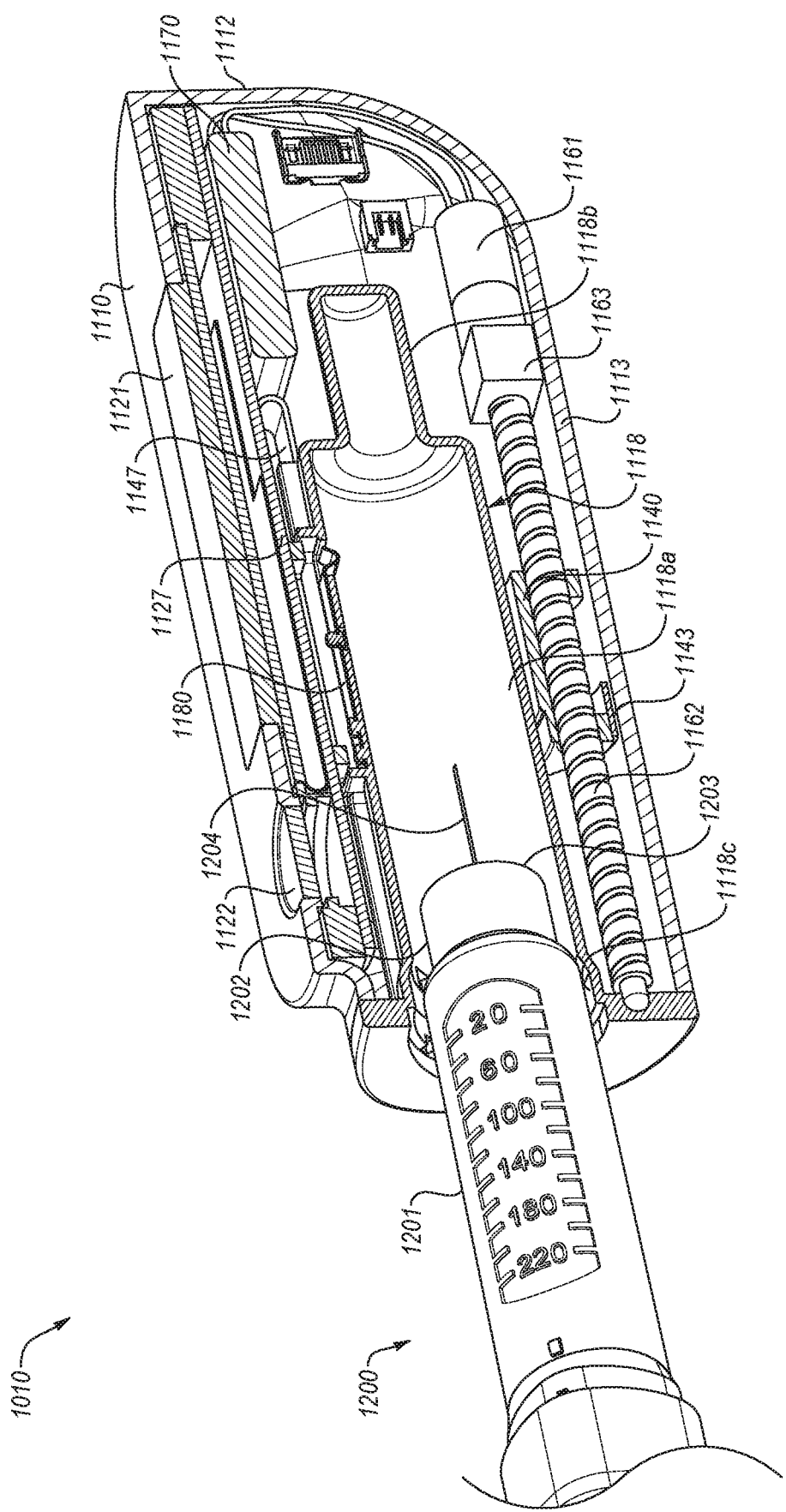
FIG. 17A is a partial cross-sectional view of the example liquid delivery system of FIG. 15.
Figure 17B:
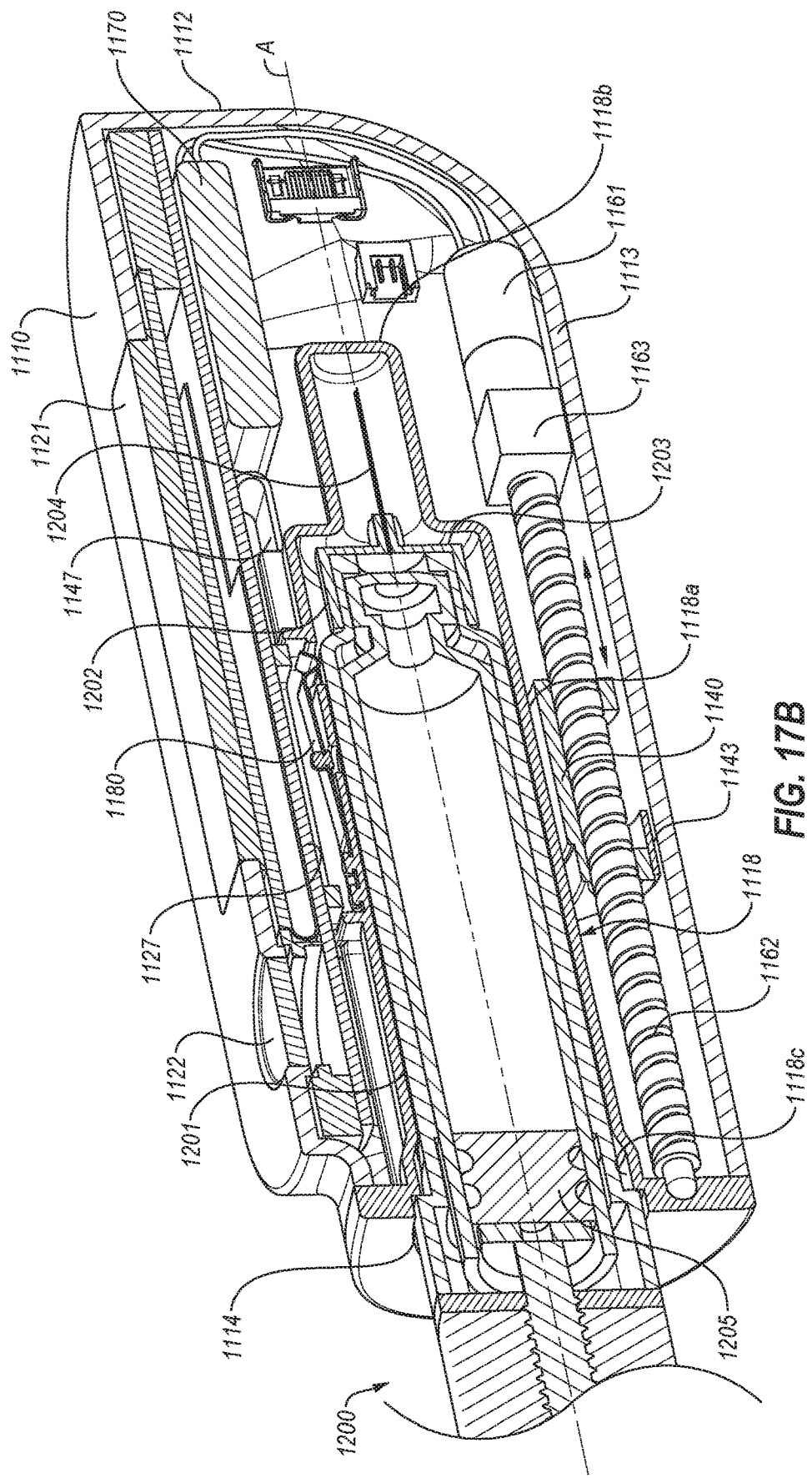
FIG. 17B is a partial cross-sectional view of the example liquid delivery system of FIG. 15.

Referring now to FIGS. 17A and 17B, partial cross-sectional views of liquid delivery system 1010 are shown, including liquid delivery device 1200 being inserted into cap device 1100 (FIG. 17A) and cap device 1100 retained on liquid delivery device 1200 (FIG. 17B). Delivery end 1202 and at least a portion of reservoir 1201 of liquid delivery device 1200 may be positioned within cavity 1111 of cap device 1100. Sensor carriage 1140 may be driven along a portion of liquid delivery device 1200 while liquid delivery device 1200 remains fixedly positioned relative to body 1110 and cavity 1111. Movement of sensor carriage 1140 between the first and second positions facilitates detection of characteristics of liquid delivery device 1200 at multiple locations of liquid delivery device 1200. In some embodiments, operation of sensor 1142 as sensor carriage 1140 travels between the first and second positions can be described as generating a scan of a portion of liquid delivery device 1200, and the output signals from sensors 1142 (e.g. alone or in conjunction with one or more sensors, such as sensor 1145) can be evaluated to determine a position of plunger 1205 within reservoir 1201, a change in position of plunger 1205 within reservoir 1201, and/or other conditions of liquid delivery device 1200.

Motor 1161 is joined to leadscrew 1162, directly or indirectly. In some embodiments, motorized drive system 1160 includes a gear train 1163 between motor 1161 and leadscrew 1162. Gear train 1163 may be configured to provide sufficient torque to leadscrew 1162 to drive sensor carriage 1140, such as a planetary gear train, compound gear train, etc. Gear train 1163 may facilitate a small or relatively low power motor 1161, and a compact motorized drive system 1160, while providing sufficient power to drive sensor carriage 1140. In various example embodiments, motor 1161, leadscrew 1162, and/or gear train 1163 may be arranged coaxially. Alternatively or additionally motor 1161 and leadscrew 1162 may be arranged at an offset or angled relative to each other (e.g. rotate about longitudinal axis that are offset, or perpendicular or otherwise angled to one another). Gear train 1163 may facilitate positioning of 1161 and leadscrew 1162 within body 1110 (e.g. without requiring a drive shaft of motor 1161 in alignment with leadscrew 1162).

Motorized drive system 1160 may drive sensor carriage 1140 along at least a portion of liquid delivery device 1200. In various example embodiments, motorized drive system 1160 may drive sensor carriage 1140 through a selected travel distance (e.g. in a forward or rearward direction between a first position and a second position) or any sequence of travel distances (e.g. in forward and/or rearward direction between first, second, or more positions). Movement of sensor carriage 1140 may thus be independent from manual operation and/or engagement between cap device 1100 and liquid delivery device 1200. In some embodiments, sensor carriage 1140 can be driven along a length of liquid delivery device multiple times (e.g. in back-and-forth movement) while liquid delivery device 1200 remains in a fixed position relative to cap device 1100. Sensor carriage 1140 driven by motorized drive system 1160 may thus promote consistent and reliable detection, and/or facilitate multiple measurements after a single capping event (e.g. multiple measurements without disengaging and reengaging liquid delivery device 1200 with cap device 1100).

Operation of motorized drive system 1160 and movement of sensor carriage 1140 may be controlled according to a selected (e.g. preprogrammed) sequence or to achieve various performance advantages. In various example embodiments, motorized drive system 1160 may drive sensor carriage 1140 between a first position and a second position each time liquid delivery device 1200 is engaged with cap device 1100. The first position and second position may be selected to reduce the travel distance of sensor carriage 1140 required to detect a characteristic of liquid delivery device 1200. For example, sensor carriage 1140 may begin at a first position that is the position of sensor carriage 1140 when liquid delivery device 1200 is engaged with cap device 1100, and the second position may be a position at which plunger 1205 or other feature is detected. The sensor carriage 1140 may thus be incrementally advanced along the length of leadscrew 1162 a distance corresponding to the distance plunger 1205 was moved during the previous dose.

In some embodiments, the sensor carriage 1140 begins at an initial position near front wall 1112 of body 1110 after a new liquid delivery device 1200 is engaged with cap device 1100. After an initial dosing event (e.g. in which the liquid delivery device 1200 is removed, used to administer a dosage, and reengaged with cap device 1100), sensor carriage 1140 is driven by motorized drive system 1160 in a first direction towards opening 1114 until plunger 1205 of liquid delivery device 1200 is encountered. Operation of motorized drive system 1160, and movement of sensor carriage 1140, is then stopped and the sensor carriage 1140 remains at the location where plunger 1205 was detected. After a subsequent dosing event, sensor carriage 1140 is driven by motorized drive system 1160 in the first direction towards opening 1114 until plunger 1205 of liquid delivery device 1200 is encountered, and operation of motorized drive system 1160 and movement of sensor carriage 1140 is again stopped. Intermittent operation of motorized drive system 1160, and corresponding movement of sensor carriage 1140, is repeated until the liquid delivery device 1200 is exhausted or a new liquid delivery device engaged with cap device 1100.

Advancement only between an initial position (e.g. a previous position of plunger 1205) and a second position (e.g. a subsequent position of plunger 1205 after a dosing event) may reduce the cumulative distance traveled by sensor carriage 1140. The sensor carriage 1140 may detect the position of plunger 1205 at multiple locations while moving only in a single direction. Alternatively or additionally, such a configuration may promote efficient operation and increase battery life by reducing the cumulative distance traveled and power consumed by driving sensor carriage 1140. In some example embodiments, a reduced travel distance of sensor carriage 1140 may also promote a reduced scan time (e.g. and a reduced period a user may be required to wait to receive information based on the scan) and reduce noise generated during operation of motorized drive system 1160.

In some example embodiments, sensor carriage 1140 may repeatedly initiate movement from a common starting point each time liquid delivery device 1200 is engaged with cap device 1100. For example, sensor carriage 1140 may begin movement from a position near delivery end 1202 of liquid delivery device 1200 and move in a first direction towards opening 1114. After a dosing event, motorized drive system 1160 may return sensor carriage in a second direction towards front wall 1112 back to the initial position. This process may continue for a series of dosing events. The travel distance of each successive operation from the first or initial position to the second position (e.g. where plunger 1205 is detected) may become successively shorter as plunger 1205 is advanced within liquid delivery device 1200 during each dosing event.

The speed of sensor carriage 1140 may be selected to achieve one or more performance advantages. In an example embodiment, the speed of sensor carriage 1140 may be selected based on one or more parameters including the resolution of sensors 1142 and/or one or more sensors of cap device 1100, duration to perform scan, power consumption, noise generation, etc. In various example embodiments, the speed of sensor carriage 1140 when driven by motorized drive system 1160 may be sufficient to drive sensor carriage 1140 along an entire length of liquid delivery device 1200 within cap device 1100 in a time of between 0.25 seconds and 8 seconds, 0.5 seconds and 4 seconds, or between 1 second and 2 seconds. Such sensor carriage speeds may facilitate a selected scan resolution while reducing power consumption and scan duration, for example.

Motorized drive system 1160 may be configured to vary the speed of sensor carriage 1140. In some embodiments, the speed of sensor carriage 1140 may be varied depending on whether sensor carriage 1140 is operating to detect a characteristic of liquid delivery device 1200. Motorized drive system 1160 may drive sensor carriage 1140 at a first speed during operation of sensor 1142 to detect a characteristic of liquid delivery device 1200, and may drive sensor carriage 1140 at a second speed (e.g. higher than the first speed) when driving sensor carriage 1140 to a position while sensor 1142 is not operating to detect a characteristic of liquid delivery device 1200.

Alternatively or additionally, motorized drive system 1160 may be configured to drive sensor carriage 1140 at two or more speeds based on one or more of the position of sensor carriage 1140, an estimated position of sensor carriage 1140 relative to plunger 1205 or other feature of liquid delivery device 1200 or cap device 1100, or sensor signals output from sensor 1142, position sensor 1145, or other sensors of cap device 1100. In an example embodiment, motorized drive system 1160 may drive sensor carriage 1140 at a first average speed over a length where plunger 1205 is not expected to be present (e.g. based on a previous plunger position, dosage information, etc.) and a second average speed over a length where plunger 1205 is expected to be present. The first average speed may be relatively higher, and the second average speed may be relatively lower. In some embodiments, motorized drive system 1160 may continuously vary the speed of sensor carriage 1140, such as by continuously decreasing the speed between an initial location (e.g. where plunger 1205 is unlikely to be present) and a second location (e.g. where plunger 1205 is located). Such adjustment of the speed of sensor carriage 1140 may promote a selected scan resolution, reliability, and/or precision in detecting the position of plunger 1205, for example, while reducing the scan duration, power consumption noise generation, etc.

Motorized drive system 1160 may be configured to facilitate improved reliability and repeatability in detecting plunger 1205 or another characteristic of liquid delivery system 1000. In an example embodiment, motorized drive system 1160 facilitates multiple measurements at a single position or series of positions while liquid delivery device 1200 remains fixedly engaged with cap device 1100. In an example embodiment, motorized drive system 1160 may drive sensor carriage 1140 in one or more back and forth movements proximate a location of interest to obtain multiple measurements. The measurements may then be averaged or otherwise processed (e.g. by processor 1125) to provide a reliable and repeatable output.

Alternatively or additionally, motorized drive system 1160 may drive sensor carriage 1140 in one or more back and forth movements proximate a location of interest based on a confidence value related to a sensor signal. For example, one or more sensor signals may be evaluated (e.g. in real time) to determine a confidence value indicative of a confidence that the sensor signals accurately correspond to plunger 1205 or another characteristic of liquid delivery system 1010. If the confidence value is below a predetermined threshold, motorized drive system 1160 may drive sensor carriage 1140 along a portion of liquid delivery device 1200 to obtain additional measurements. In some embodiments, cap device 1100 may output an alert to the user of a potential error based on the confidence value and/or request input from the user.

Motorized drive system 1160 may be activated by engagement between cap device 1100 and liquid delivery device 100. For example, cap device 1100 may include a sensor 1180 located to detect the present of liquid delivery device 1200 within sleeve 1118. Sensor 1180 may be a contact switch, optical sensor, etc. When liquid delivery device 1200 is engaged with cap device 1100, sensor 1180 may emit a signal indicative of the presence of liquid delivery device 1200. Motorized drive system 1160 may be activated to drive sensor carriage 140 after sensor 1180 emits a signal indicating that liquid delivery device 1200 has been engaged with cap device 1100. In some example embodiments, motorized drive system 1160 may be activated to drive sensor carriage 140 by the signal emitted by sensor 1180. For example, motorized drive system 1160 may be activated to drive sensor carriage 1140 a predetermined time (e.g. 1 second, 2 seconds, 5 seconds, etc.) after sensor 1180 emits a signal indicating the presence of liquid delivery device 1200. A predetermined period may ensure that liquid delivery device 1200 is fully engaged and in a fixed position relative to cap device 1100, and/or that the contents of reservoir 1204 have settled, before driving sensor carriage 1140 to detect plunger 1205 or other feature of liquid delivery system 1010.

Alternatively or additionally, operation of motorized drive system 1160 may be dependent on signals output by one or more additional sensors of cap device 1100. For example, cap device 1100 may include an accelerometer that outputs a signal related to movement of cap device 1100. Operation of motorized drive system 1160 may be initiated after a period of 1 second, 2 seconds, or more, after the accelerometer outputs a signal indicative that cap device is stationary or not significantly moving. The reliability and repeatability of motorized drive system 1160, sensor carriage 1140, and the sensors carried by sensor carriage 1140 may be promoted by operation when cap device 1100 is stationary or not significantly moving.

Figure 18:
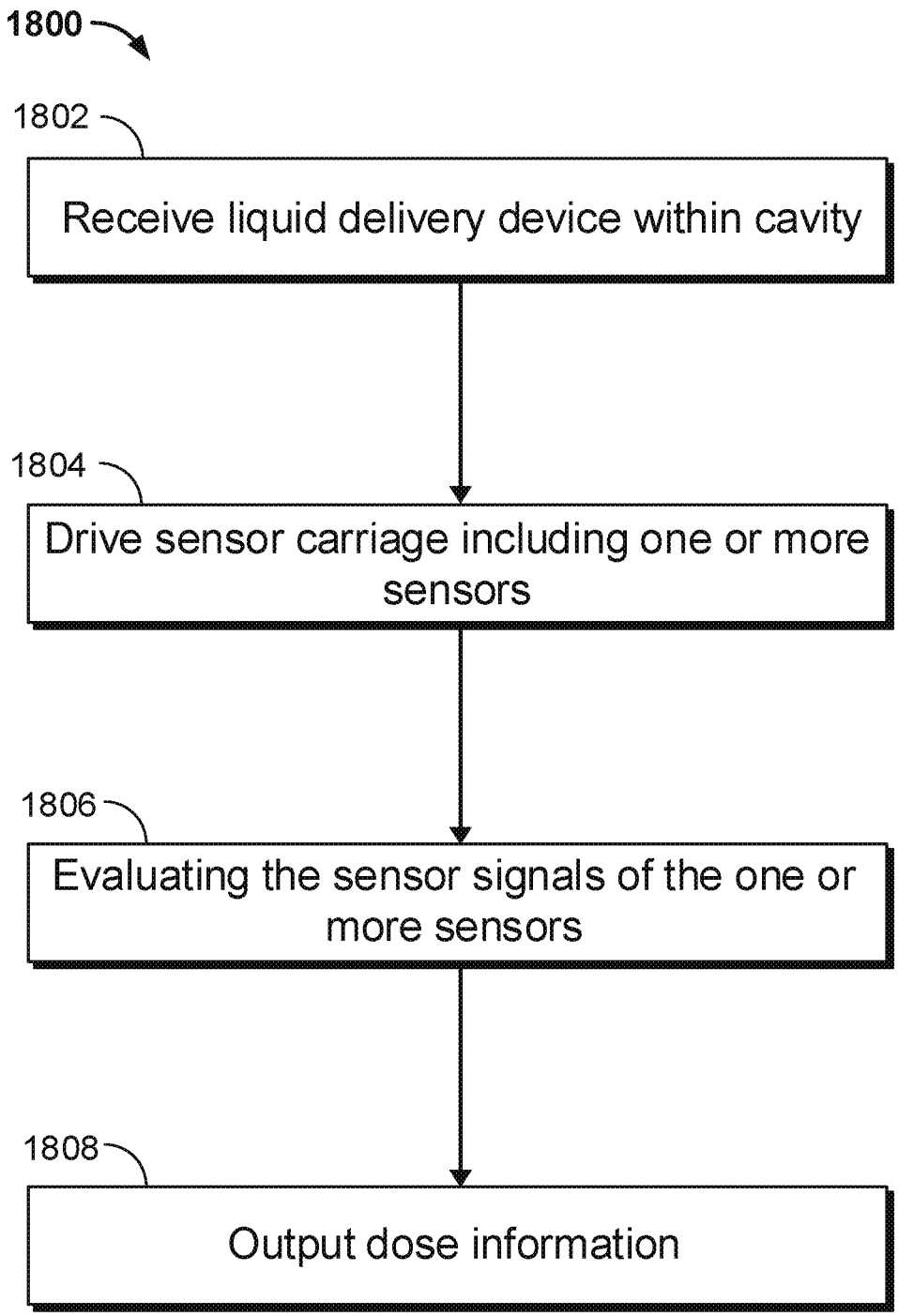
FIG. 18 is a flow diagram of an example method of evaluating the condition of a liquid delivery device.

Various example cap devices described herein facilitate effective, repeatable techniques of evaluating a condition of a liquid delivery device, with little or no dependence on manual user movement of components of the cap devices. Referring to FIG. 18, a flow diagram of an example method 1800 of evaluating the condition of a liquid device is shown. Method 1800 includes operation 1802 of receiving at least a portion of a liquid delivery device within a cavity of a cap device. In various example embodiments, the liquid delivery device may have features and characteristics similar to liquid delivery devices 200, 400, 600, 1200 described herein, and may be a pen-injector device for administering a dose of insulin.

Operation 1802 may include aligning the liquid delivery device with the cavity of the cap device, such as aligning a central longitudinal axis of the liquid delivery device with a central longitudinal axis of the cavity of the cap device. Alternatively or additionally, operation 1802 may include aligning the liquid delivery device into one or more discrete alignment positions with the cap device. For example, liquid delivery device and/or cap device may have an asymmetrical feature and/or non-circular shape that facilitates receiving the liquid delivery device in one or more discrete positions selected based on locations of one or more sensors within the cap device. Operation 1802 including aligning the liquid delivery device with the cap device in a particular orientation facilitates desired interaction between one or more sensors of the cap device and the liquid delivery device by reducing interference or obstruction by ribs, indicia, opaque regions, and/or other features.

In an example embodiment, operation 1802 of receiving the liquid delivery device with the cavity of the cap device may include fixedly engaging the cap device with the liquid delivery device. For example, after operation 1802, relative motion between the liquid delivery device and the cap device may be limited such that the liquid delivery device is not rotatable within the cavity and/or the liquid delivery device is not movable longitudinally within the cavity.

Method 1800 may include operation 1804 of driving a sensor carriage including one or more sensors. Operation 1804 may include driving the sensor carriage by a motorized drive system including an electric motor. For example, motorized drive system may drive the sensor carriage from a first position to a second position. One or more sensor signals located on the sensor carriage operate while the sensor carriage moves between the first and second positions to output sensor signals indicative of one or more features of the liquid delivery device.

In some example embodiments, operation 1804 of driving the sensor carriage may be initiated without additional manual operation. For example, the cap device may detect engagement with the liquid delivery device, such as by a sensor, and initiate operation of the motorized drive system after detecting liquid delivery device.

Operation 1804 may optionally include driving the sensor carriage in multiple directions. For example, the motorized drive system may drive the sensor carriage in one or more back and forth movements, such as to obtain multiple measurements over a particular location or locations. The sensor carriage may be driven by the motorized drive system, including in back and forth directions, while the liquid delivery device remains fixedly positioned relative to the cap device, and/or without additional manual intervention, for example.

Method 1800 may further include operation 1806 of evaluating an output of the one or more sensors indicative of the presence of a feature of the liquid delivery device. For example, the cap device may include a processor configured to evaluate sensor signals from one or more of the sensors, such as a variation in sensor signals indicative of the plunger, and to determine a corresponding position. In some embodiments, operation 1806 may include storing the corresponding position and comparing the corresponding position during subsequent capping events. Evaluating the sensor signals may including evaluating a change in position to determine the volume of the previous dose delivery (e.g. by evaluating the distance traveled by plunger 205), a remaining volume within the liquid delivery device, or other characteristics of the liquid delivery device.

In some embodiments, method 1800 may include operation 1808 of outputting information related to the position of the plunger. Information may be output by the cap device and/or transmitted to one or more remote devices. For example, operation 1808 may include displaying the previously delivered dose. Alternatively or additionally, operation 1808 may include displaying dose information related to a remaining total volume of liquid within the reservoir of the liquid delivery device, a remaining number of doses within the reservoir of the liquid delivery device, a remaining duration until the reservoir of the liquid delivery device is emptied, a time of the previous dose (e.g. a time of operation 1802 of receiving the liquid delivery device within the cavity), an elapsed time since the last dose (e.g. an elapsed time since operation 802 of receiving the liquid delivery device within the cavity), and/or other information related to the liquid delivery device.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A liquid delivery system cap device, the cap device comprising:
   a body defining a cavity configured to receive at least a portion of a liquid delivery device;
   a sensor carriage movable within the cavity and including a first sensor; and
   a motor configured to move the sensor carriage;
   wherein the sensor carriage is movable between a first position and a second position while the liquid delivery device is in a fixed position relative to the cavity.

2. The cap device of claim 1, wherein the motor is configured to drive the sensor carriage along a portion of the liquid delivery device.

3. The cap device of claim 1, wherein the cavity is defined by a front wall and one or more side walls of the body, and the body defines an opening to the cavity.

4. The cap device of claim 1, wherein the first sensor is configured to output a sensor signal indicative of a physical feature of the liquid delivery device.

5. The cap device of claim 1, wherein the first sensor is configured to output a sensor signal indicative of a plunger of the liquid delivery device while the sensor carriage moves between the first position and the second position.

6. The cap device of claim 1, further comprising a sleeve configured to receive at least a portion of the liquid delivery device.

7. The cap device of claim 6, wherein the sensor carriage is configured to move along an outside of the sleeve.

8. The cap device of claim 7, wherein the first sensor comprises an optical path between a first optical emitter and a first optical receiver.

9. The cap device of claim 8, wherein the optical path is perpendicular to a longitudinal axis of the cavity of the cap device.

10. The cap device of claim 8, wherein the optical path passes through a material thickness of the sleeve.

11. The cap device of claim 8, wherein the sensor carriage comprises a second optical sensor having a second optical emitter aligned with a second optical receiver.

12. The cap device of claim 11, wherein the first optical emitter is not aligned with the second optical receiver, and the second optical emitter is not aligned with the first optical receiver.

13. The cap device of claim 1, further comprising a position sensor.

14. The cap device of claim 13, further comprising a processor configured to detect a plunger of the liquid delivery device based on a variation in the sensor signal of the first sensor, and to determine a corresponding position based on a sensor signal output by the position sensor.

15. The cap device of claim 13, wherein the position sensor comprises a linear encoder, the linear encoder including a codestrip and an encoder movable along the codestrip.

16. A liquid delivery system, comprising:
    a liquid delivery device, comprising:
        a reservoir,
        a liquid within the reservoir, and
        a plunger movable within the reservoir to dispense liquid from the reservoir; and
    a cap device, comprising:
        a body defining a cavity configured to receive at least a portion of a liquid delivery device,
        a sensor carriage movable within the cavity and including one or more sensors configured to output a sensor signal indicative of a physical feature of the liquid delivery device,
        a motor configured to move the sensor carriage, and
        a position sensor;
    wherein the sensor carriage is movable between a first position and a second position relative to the cavity while the liquid delivery device is in a fixed position relative to the cavity.

17. The liquid delivery system of claim 16, further comprising a processor configured to detect a plunger of the liquid delivery device based on a variation in the sensor signal, and to determine a corresponding position based on a sensor signal of the position sensor.

18. The liquid delivery system of claim 17, wherein the processor is located in the cap device.

19. The liquid delivery system of claim 18, wherein the one or more sensors located on the sensor carriage comprise first and second optical sensors, the first optical sensor having a first optical emitter aligned with a first optical receiver, and the second optical sensor having a second optical emitter aligned with a second optical receiver.

20. A method of evaluating the condition of a liquid delivery device, comprising:
    receiving at least a portion of a liquid delivery device within a cavity of a cap device;
    driving a sensor carriage including one or more sensors from a first position to a second position while the liquid delivery device remains in a fixed position within the cavity, wherein driving the sensor carriage comprises driving the sensor carriage by an electric motor; and
    evaluating an output of the one or more sensors indicative of the presence of a feature of the liquid delivery device.

21. The method of claim 20, further comprising evaluating by a processor within the cap device an output of a position sensor to evaluate a position of the feature of the liquid delivery device.

22. The method of claim 21, wherein the feature of the liquid delivery device is a plunger.

* * * * *